(12) United States Patent
Benayahu et al.

(10) Patent No.: US 7,919,602 B2
(45) Date of Patent: Apr. 5, 2011

(54) POLYPEPTIDES, POLYNUCLEOTIDES ENCODING SAME, ANTIBODIES THEREAGAINST AND METHODS OF USING SAME FOR DIAGNOSING AND TREATING CANCER AND SKELETAL DISORDERS

(75) Inventors: Dafna Benayahu, Herzlia (IL); Irena Shur, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 199 days.

(21) Appl. No.: 11/508,301

(22) Filed: Aug. 23, 2006

(65) Prior Publication Data

US 2006/0292153 A1 Dec. 28, 2006

Related U.S. Application Data

(63) Continuation-in-part of application No. PCT/IL2005/000225, filed on Feb. 23, 2005.

(60) Provisional application No. 60/546,181, filed on Feb. 23, 2004.

(51) Int. Cl.
*C07H 21/02* (2006.01)
*C12Q 1/68* (2006.01)
(52) U.S. Cl. ............................. 536/23.1; 435/6
(58) Field of Classification Search .................. None
See application file for complete search history.

(56) References Cited

FOREIGN PATENT DOCUMENTS

| WO | WO 02/59315 | 1/2002 |
| WO | WO 02/10388 | 7/2002 |
| WO | WO 03/050253 | 6/2003 |
| WO | WO 2004/003147 | 8/2004 |

OTHER PUBLICATIONS

Huang et al., Tissue Inhibitor of Metalloproteinases-4 (TIMP-4) Gene Expression is Increased in Human Osteoarthritic Femoral Head Cartilage, Journal of Cellular biochemistry, 2002, vol. 85, pp. 295-303/.*
Shur et al., Molecular and Cellular Characterization of SE:-OB/SVEP1 in Osteogenic Cells In Vivo and In Vitro, Journal of Cellular Physiology, 2006, vol. 206, pp. 420-427.*
Abdallah et al., Regulation of Human Skeletal Stem Cells Differentiation by Dlk1/Pref-1, Journal of Bone and Mineral Research, online publication on Jan. 19, 2004, vol. 19, pp. 841-852.*
NCBI Blast (last viewed on Jun. 29, 2010).*
Yanari et al., The reaction of ninhydrin with dipeptides: Differences in reaction rates and theretical yields., 1956, J Biol Chem, vol. 220, pp. 683-689.*
Carnac et al., The retinoblastoma-like protein p130 is involved in the determination of reserve cells in differentiating myoblasts., Current Biology, 2000, vol. 10., pp. 543-546.*
Kay "Human DNA Sequence From Clone RP!!-410K21 on Chromosome 9 Contains the 5' End of the Gene for the Likely Ortholog of Mouse Polydom (POLYDOM), A Novel Gene and A CpG Island", Database EMBL, Database Accession No. AL592463, Jul. 6, 2001.
Gilgés et al. "Polydom: A Secreted Protein With Pentraxin, Complement Control Protein, Epidermal Growth Factor and Von.Willebrand Factor A Domains", Biochemical Journal, 352: 49-59, 2000. P.51, r-h col. § I, P.56, 1-h col. § 2.
Compston "Sex Steroids and Bone", Physiological Reviews, 81(1): 419-447, 2001. p. 428-433.

(Continued)

*Primary Examiner* — Alexander D Kim

(57) ABSTRACT

An isolated polypeptide is provided, comprising an amino acid sequence being at least 88% homologous to SEQ ID NO: 15 (human) as determined by BlastP using default parameters, the isolated polypeptide being capable of promoting cell adhesion and/or cell homing.

4 Claims, 23 Drawing Sheets
(17 of 23 Drawing Sheet(s) Filed in Color)

OTHER PUBLICATIONS

International Preliminary Report on Patentability Dated Sep. 8, 2006 From the International Bureau of WIPO Re.: Application No. PCT/IL2005/000225.

Response dated Oct. 18, 2010 to Official Action of Jul. 16, 2010 From the US Patent and Trademark Office Re.: U.S. Appl. No. 11/508,301.

* cited by examiner

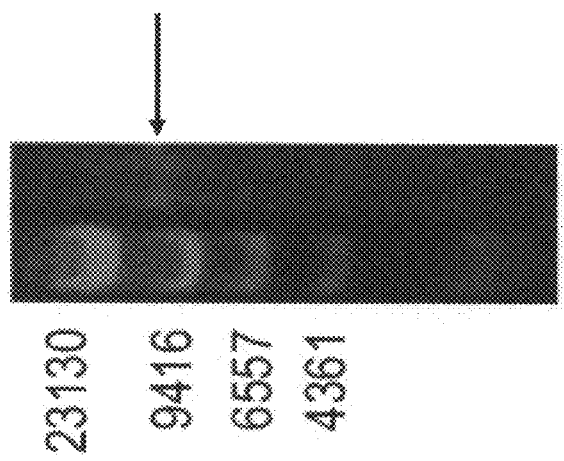

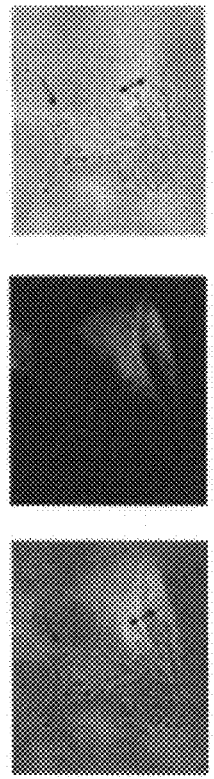
Fig. 5
SEL-OB
CCP 34 domains
EGF Ca 9 domains
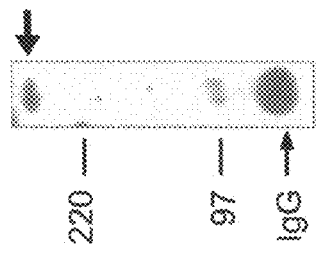
Fig. 7A  Fig. 7B  Fig. 7C
Fig. 7D  Fig. 7E
Fig. 6

Fig. 8B  Blank    SEL-OB

MDA-231          MCF7          T-47D

```
ggattgtgtctgtccccagtgtcagatgaaagggc   aggctcttggccgctgcccgc
 D  C  V  C  P  Q  C  Q  M  K  G  R     G  S  W  L  P  R
gcccagctccggcacgctccctctgcgagtccggccgccagcgcctcttcccgccgag
 A  Q  L  R  A  R  P  S  A  S  P  A  A  Q  L  F  P  P  E
ccgccgcctgcgctccggggcagccgctctgtctccagcgc   tggcctcgcctggcc
 P  P  A  L  R  G  S  R  S  V  S  S  A     W  P  R  L  A
ttttgttgctgggtctggcgctcgtttcgggctgggcgacctttcagcagatgtcccg
 F  C  C  W  G  L  A  L  V  S  G  W  A  T  F  Q  Q  M  S  P
tcgcgcaatttcagcttccgcctcttcccgagaccgcgcccggggcccccgggagtatc
 S  R  N  F  S  F  R  L  F  P  E  T  A  P  G  A  P  G  S  I
cccgcgccgccgctcctggcgacgaagcggcggggagcagagtggagcggctgggccag
 P  A  P  P  A  P  G  D  E  A  A  G  S  R  V  E  R  L  G  Q
gcgttccggcgacgcgtgcggctgctgcgggagctcagcgagcgcctggagcttgtcttc
 A  F  R  R  R  V  R  L  L  R  E  L  S  E  R  L  E  L  V  F
ctggtggatgattcgtccagcgtgggcgaagtcaacttccgcagcgagctcatgttcgtc
 L  V  D  D  S  S  S  V  G  E  V  N  F  R  S  E  L  M  F  V
cgcaagctgctgtccgacttccccgtggtgcccacggccacgcgcgtggccatcgtgacc
 R  K  L  L  S  D  F  P  V  V  P  T  A  T  R  V  A  I  V  T
ttctcgtccaagaactacgtggtgccgcgcgtcgattacatctccacccgcgcgcgcgc
 F  S  S  K  N  Y  V  V  P  R  V  D  Y  I  S  T  R  R  A  R
cagcacaagtgcgcgctgctgctccaagagatccctgccatctcctaccgaggtggcggc
 Q  H  K  C  A  L  L  L  Q  E  I  P  A  I  S  Y  R  G  G  G
acctacaccaagggcgccttccagcaagccgcgcaaattcttcttcatgctagagaaaac
 T  Y  T  K  G  A  F  Q  Q  A  A  Q  I  L  L  H  A  R  E  N
tcaacaaaagttgtatttctcatcactgatggatattccaatggggcagacctagacca
 S  T  K  V  V  F  L  I  T  D  G  Y  S  N  G  G  D  P  R  P
attgcaagcgtcactgcgagattcaggagtggagatcttcactttggcatatggcaaggg
 I  A  A  S  L  R  D  S  G  V  E  I  F  T  F  G  I  W  Q  G
aacattcgagagctgaatgacatggcttccacccccaaggaggagcactgttacctgcta
 N  I  R  E  L  N  D  M  A  S  T  P  K  E  E  H  C  Y  L  L
cacagttttgaagaatttgaggctttagctcgccgggcattgcatgaagatctaccttct
 H  S  F  E  E  F  E  A  L  A  R  R  A  L  H  E  D  L  P  S
gggagttttattcaagatgatatggtccactgctcatatctttgtgatgaaggcaaggac
 G  S  F  I  Q  D  D  M  V  H  C  S  Y  L  C  D  E  G  K  D
tgctgtgaccgaatgggaagctgcaaatgtggacacacacaggccattttgagtgcatc
 C  C  D  R  M  G  S  C  K  C  G  T  H  T  G  H  F  E  C  I
tgtgaaaaggggtattacgggaaaggtctgcagtatgaatgcacagcttgcccatcgggg
 C  E  K  G  Y  Y  G  K  G  L  Q  Y  E  C  T  A  C  P  S  G
acatacaaacctgaaggctcaccaggaggaatcagcagttgcattccatgtcctgatgaa
 T  Y  K  P  E  G  S  P  G  G  I  S  S  C  I  P  C  P  D  E
aatcacacctctccacctggaagcacatcccctgaagactgtgtctgcagagagggatac
 N  H  T  S  P  P  G  S  T  S  P  E  D  C  V  C  R  E  G  Y
agggcatctggccagacctgtgaacttgtccactgccctgccctgaagcctcccgaaaat
 R  A  S  G  Q  T  C  E  L  V  H  C  P  A  L  K  P  P  E  N
ggttactttatccaaaacacttgcaacaaccacttcaatgcagcctgtggggtccgatgt
 G  Y  F  I  Q  N  T  C  N  N  H  F  N  A  A  C  G  V  R  C
cacccctggatttgatcttgtgggaagcagcatcatcttatgtctacccaatggtttgtgg
 H  P  G  F  D  L  V  G  S  S  I  I  L  C  L  P  N  G  L  W
tccggtttagagagctactgcagagtaagaacatgtcctcatctccgccagcgaaacat
 S  G  L  E  S  Y  C  R  V  R  T  C  P  H  L  R  Q  R  K  H
ggccacatcagctgttctacaagggaaatgttatataagacaacatgtttggttgccgt
 G  H  I  S  C  S  T  R  E  M  L  Y  K  T  T  C  L  V  A  C
gatgaagggtacagactagaaggcagtgataagcttacttgtcaaggaaacagccagtgg
 D  E  G  Y  R  L  E  G  S  D  K  L  T  C  Q  G  N  S  Q  W
gatgggccagaacccggtgtgtggagcgccactgttccaccctttcagatgcccaaagat
 D  G  P  E  P  R  C  V  E  R  H  C  S  T  F  Q  M  P  K  D
gtcatcatatccccccacaactgtggcaagcagccagccaaatttgggacgatctgctat
 V  I  I  S  P  H  N  C  G  K  Q  P  A  K  F  G  T  I  C  Y
```

Fig. 13A

```
gtaagttgccgccaagggttcattttatctggagtcaaagaaatgctgagatgtaccact
 V  S  C  R  Q  G  F  I  L  S  G  V  K  E  M  L  R  C  T  T
tctggaaaatggaatgtcggagttcaggcagctgtgtgtaaagacgtggaggctcctcaa
 S  G  K  W  N  V  G  V  Q  A  A  V  C  K  D  V  E  A  P  Q
atcaactgtcctaaggacatagaggctaagactctggaacagcaagattctgccaatgtt
 I  N  C  P  K  D  I  E  A  K  T  L  E  Q  Q  D  S  A  N  V
acctggcagattccaacagctaaagacaactctggtgaaaaggtgtcagtccacgttcat
 T  W  Q  I  P  T  A  K  D  N  S  G  E  K  V  S  V  H  V  H
ccagctttcaccccaccttacctttccccaattggagatgttgctatcgtatacacggca
 P  A  F  T  P  P  Y  L  F  P  I  G  D  V  A  I  V  Y  T  A
actgacctatccggcaaccaggccagctgcattttccatatcaaggttattgatgcagaa
 T  D  L  S  G  N  Q  A  S  C  I  F  H  I  K  V  I  D  A  E
ccacctgtcatagactggtgcagatctccacctcccgtccaggtctcggagaaggtacat
 P  P  V  I  D  W  C  R  S  P  P  P  V  Q  V  S  E  K  V  H
gccgcaagctgggatgagcctcagttctcagacaactcaggggctgaattggtcattacc
 A  A  S  W  D  E  P  Q  F  S  D  N  S  G  A  E  L  V  I  T
agaagtcatacacaaggagacctttcctcaaggggagactatagtacagtatacggcc
 R  S  H  T  Q  G  D  L  F  P  Q  G  E  T  I  V  Q  Y  T  A
actgacccctcaggcaataacaggacatgtgatatccatattgtcataaaaggttctccc
 T  D  P  S  G  N  N  R  T  C  D  I  H  I  V  I  K  G  S  P
tgtgaaattccattcacacctgtaaatggggattttatatgcactccagataatactgga
 C  E  I  P  F  T  P  V  N  G  D  F  I  C  T  P  D  N  T  G
gtcaactgtacattaacttgcttggagggctatgatttcacagaagggtctactgacaag
 V  N  C  T  L  T  C  L  E  G  Y  D  F  T  E  G  S  T  D  K
tattattgtgcttatgaagatggcgtctggaaaccaacatataccactgaatggccagac
 Y  Y  C  A  Y  E  D  G  V  W  K  P  T  Y  T  T  E  W  P  D
tgtgccaaaaaacgttttgcaaaccacgggttcaagtcctttgagatgttctacaaagca
 C  A  K  K  R  F  A  N  H  G  F  K  S  F  E  M  F  Y  K  A
gctcgttgtgatgacacagatctgatgaagaagttttctgaagcatttgagacgaccctg
 A  R  C  D  D  T  D  L  M  K  K  F  S  E  A  F  E  T  T  L
ggaaaaatggtcccatcatttgtagtgatgcagaggacattgactggagactggaggag
 G  K  M  V  P  S  F  C  S  D  A  E  D  I  D  W  R  L  E  E
aacctgaccaaaaaatattgcctagaatataattatgactatgaaaatggctttgcaatt
 N  L  T  K  K  Y  C  L  E  Y  N  Y  D  Y  E  N  G  F  A  I
ggaccaggtggctggggtgcagctaataggctggattactcttacgatgacttcctggac
 G  P  G  G  W  G  A  A  N  R  L  D  Y  S  Y  D  D  F  L  D
actgtgcaagaaacagccacaagcatcggcaatgccaagtcctcacggattaaaagaagt
 T  V  Q  E  T  A  T  S  I  G  N  A  K  S  S  R  I  K  R  S
gccccattatctgactataaaattaagttaatttttaacatcacagctagtgtgccatta
 A  P  L  S  D  Y  K  I  K  L  I  F  N  I  T  A  S  V  P  L
cccgatgaaagaaatgataccccttgaatgggaaaatcagcaacgactccttcagacattg
 P  D  E  R  N  D  T  L  E  W  E  N  Q  Q  R  L  L  Q  T  L
gaaactatcacaaataaactgaaaaggactctcaacaaagaccccatgtattcctttcag
 E  T  I  T  N  K  L  K  R  T  L  N  K  D  P  M  Y  S  F  Q
cttgcatcagaaatacttatagccgacagcaattcattaggaacaaaaaaggcttccccc
 L  A  S  E  I  L  I  A  D  S  N  S  L  G  T  K  K  A  S  P
ttctgcagaccaggctcagtgctgagagggcgtatgtgtgtcaattgccctttgggaacc
 F  C  R  P  G  S  V  L  R  G  R  M  C  V  N  C  P  L  G  T
tattataatctggaacatttcacctgtgaaagctgccggatcggatcctatcaagatgaa
 Y  Y  N  L  E  H  F  T  C  E  S  C  R  I  G  S  Y  Q  D  E
gaagggcaacttgagtgcaagctttgccctctgggatgtacacggaatatatccattca
 E  G  Q  L  E  C  K  L  C  P  S  G  M  Y  T  E  Y  I  H  S
agaaacatctctgattgtaaagctcagtgtaaacaaggcacctactcatgcagtggactt
 R  N  I  S  D  C  K  A  Q  C  K  Q  G  T  Y  S  C  S  G  L
gagacttgtgaatcgtgtccactgggcacttatcagccaaaatttggttcccggagctgc
 E  T  C  E  S  C  P  L  G  T  Y  Q  P  K  F  G  S  R  S  C
ctctcgtgtccagaaaacacctcaactgtgaaaagaggagccgtgaacatttctgcatgt
 L  S  C  P  E  N  T  S  T  V  K  R  G  A  V  N  I  S  A  C
```

Fig. 13A (Cont)

```
ggagttccttgtccagaaggaaaattctcgcgttctgggttaatgccctgtcacccatgt
 G  V  P  C  P  E  G  K  F  S  R  S  G  L  M  P  C  H  P  C
cctcgtgactattaccaacctaatgcagggaaggccttctgcctggcctgtccctttat
 P  R  D  Y  Y  Q  P  N  A  G  K  A  F  C  L  A  C  P  F  Y
ggaactaccccattcgctggttccagatccatcacagaatgttcaagttttagttcaact
 G  T  T  P  F  A  G  S  R  S  I  T  E  C  S  S  F  S  S  T
ttctcagcggcagaggaaagtgtggtgcccctgcctctcttggacatattaaaagagg
 F  S  A  A  E  E  S  V  V  P  P  A  S  L  G  H  I  K  K  R
catgaaatcagcagtcaggttttccatgaatgcttctttaaccttgccacaatagtgga
 H  E  I  S  S  Q  V  F  H  E  C  F  F  N  P  C  H  N  S  G
acctgccagcaacttgggcgtggttatgtttgtctctgtccacttggatatacaggctta
 T  C  Q  Q  L  G  R  G  Y  V  C  L  C  P  L  G  Y  T  G  L
aagtgtgaaacagacatcgatgagtgcagcccactgccttgcctcaacaatggagtttgt
 K  C  E  T  D  I  D  E  C  S  P  L  P  C  L  N  N  G  V  C
aaagacctagttggggaattcatttgtgagtgcccatcaggttacacaggtcagcggtgt
 K  D  L  V  G  E  F  I  C  E  C  P  S  G  Y  T  G  Q  R  C
gaagaaaatataaatgagtgtagctccagtccttgtttaaataaaggaatctgtgttgat
 E  E  N  I  N  E  C  S  S  S  P  C  L  N  K  G  I  C  V  D
ggtgtggctggctatcgttgcacatgtgtgaaaggatttgtaggcctgcattgtgaaaca
 G  V  A  G  Y  R  C  T  C  V  K  G  F  V  G  L  H  C  E  T
gaagtcaatgaatgccagtcaaacccatgcttaaataatgcagtctgtgaagaccaggtt
 E  V  N  E  C  Q  S  N  P  C  L  N  N  A  V  C  E  D  Q  V
gggggattcttgtgcaaatgcccacctggattttttgggtacccgatgtggaaagaacgtc
 G  G  F  L  C  K  C  P  P  G  F  L  G  T  R  C  G  K  N  V
gatgagtgtctcagtcagccatgcaaaaatggagctacctgtaaagacggtgccaatagc
 D  E  C  L  S  Q  P  C  K  N  G  A  T  C  K  D  G  A  N  S
ttcagatgcctgtgtgcagctggcttcacaggatcacactgtgaattgaacatcaatgaa
 F  R  C  L  C  A  A  G  F  T  G  S  H  C  E  L  N  I  N  E
tgtcagtctaatccatgtagaaatcaggccacctgtgtggatgaattaaattcatacagt
 C  Q  S  N  P  C  R  N  Q  A  T  C  V  D  E  L  N  S  Y  S
tgtaaatgtcagccaggattttcaggcaaaaggtgtgaaacagaacagtctacaggcttt
 C  K  C  Q  P  G  F  S  G  K  R  C  E  T  E  Q  S  T  G  F
aacctggatttttgaagtttctggcatctatggatatgtcatgctagttggcatgctccca
 N  L  D  F  E  V  S  G  I  Y  G  Y  V  M  L  V  G  M  L  P
tctctccatgctctaacctgtaccttctggatgaaatcctctgacgacatgaactatgga
 S  L  H  A  L  T  C  T  F  W  M  K  S  S  D  D  M  N  Y  G
acaccaatctcctatgcagttgataacggcagcgacaatacccttgctcctgactgattat
 T  P  I  S  Y  A  V  D  N  G  S  D  N  T  L  L  L  T  D  Y
aacggctgggttctttatgtgaatggcagggaaaagataacaaactgtccctcggtaat
 N  G  W  V  L  Y  V  N  G  R  E  K  I  T  N  C  P  S  V  N
gatggcagatggcatcatattgcaatcacttggacaagtgccaatggcatctggaaagtc
 D  G  R  W  H  H  I  A  I  T  W  T  S  A  N  G  I  W  K  V
tatatcgatgggaaattatctgacggtggtgctggcctctctgttggtttgcccatacct
 Y  I  D  G  K  L  S  D  G  G  A  G  L  S  V  G  L  P  I  P
ggtatgtttggtggtggtgcgttagttctgggcaagagcaagacaaaaaggagaggga
 G  M  F  G  G  G  A  L  V  L  G  Q  E  Q  D  K  K  G  E  G
ttcagcccagctgagtcttttgtgggctccataagccagctcaacctctgggactatgtc
 F  S  P  A  E  S  F  V  G  S  I  S  Q  L  N  L  W  D  Y  V
ctgtctccacagcaggtgaagtcactggctacctcctgcccagaggaactcagtaaagga
 L  S  P  Q  Q  V  K  S  L  A  T  S  C  P  E  E  L  S  K  G
aacgtgttagcatggcctgatttcttgtcaggaattgtggggaaagtgaagatcgattct
 N  V  L  A  W  P  D  F  L  S  G  I  V  G  K  V  K  I  D  S
aagagcatattttgttctgattgcccacgcttaggagggtcagtgcctcatctgagaact
 K  S  I  F  C  S  D  C  P  R  L  G  G  S  V  P  H  L  R  T
gcatctgaagatttaaagccaggttccaaagtcaatctgttctgtgatccaggcttccag
 A  S  E  D  L  K  P  G  S  K  V  N  L  F  C  D  P  G  F  Q
ctggtcgggaaccctgtgcagtactgtctgaatcaaggacagtggacacaaccacttcct
 L  V  G  N  P  V  Q  Y  C  L  N  Q  G  Q  W  T  Q  P  L  P
```

Fig. 13A (Cont)

```
cactgtgaacgcattagctgtggggtgccacctcctttggagaatggcttccattcagcc
 H  C  E  R  I  S  C  G  V  P  P  P  L  E  N  G  F  H  S  A
gatgacttctatgctggcagcacagtaacctaccagtgcaacaatggctactatctattg
 D  D  F  Y  A  G  S  T  V  T  Y  Q  C  N  N  G  Y  Y  L  L
ggtgactcaaggatgttctgtacagataatggagctggaacggcgtttcaccatcctgc
 G  D  S  R  M  F  C  T  D  N  G  S  W  N  G  V  S  P  S  C
cttgatgtcgatgagtgtgcagttggatcagattgtagtgagcatgcttcttgcctgaac
 L  D  V  D  E  C  A  V  G  S  D  C  S  E  H  A  S  C  L  N
gtagatggatcctacatatgttcatgtgtcccctcgtacacaggagatgggaaaaactgt
 V  D  G  S  Y  I  C  S  V  P  S  Y  T  G  D  G  K  N  C
gcagaacctataaaatgtaaggctccaggaaatccggaaaatggccactcctcaggtgag
 A  E  P  I  K  C  K  A  P  G  N  P  E  N  G  H  S  S  G  E
atttatacagtaggtgccgaagtcacattttcgtgtcaggaaggataccagttgatggga
 I  Y  T  V  G  A  E  V  T  F  S  C  Q  E  G  Y  Q  L  M  G
gtaaccaaaatcacatgtttggagtctggagaatggaatcatctaataccatattgtaaa
 V  T  K  I  T  C  L  E  S  G  E  W  N  H  L  I  P  Y  C  K
gctgtttcatgtggtaaaccggctattccagaaaatggttgcattgaggagttagcattt
 A  V  S  C  G  K  P  A  I  P  E  N  G  C  I  E  E  L  A  F
acttttggcagcaaagtgacatataggtgtaataaaggatatactctggccggtgataaa
 T  F  G  S  K  V  T  Y  R  C  N  K  G  Y  T  L  A  G  D  K
gaatcatcctgtcttgctaacagttcttggagtcattcccctcctgtgtgtgaaccagtg
 E  S  S  C  L  A  N  S  S  W  S  H  S  P  P  V  C  E  P  V
aagtgttctagtccggaaaatataaataatggaaaatatatttttgagtgggcttacctac
 K  C  S  S  P  E  N  I  N  N  G  K  Y  I  L  S  G  L  T  Y
ctttctactgcatcatattcatgcgatacaggatacagcttacagggcccttccattatt
 L  S  T  A  S  Y  S  C  D  T  G  Y  S  L  Q  G  P  S  I  I
gaatgcacggcttctggcatctgggacagagcgccacctgcctgtcacctcgtcttctgt
 E  C  T  A  S  G  I  W  D  R  A  P  P  A  C  H  L  V  F  C
ggagaaccacctgccatcaaagatgctgtcattacggggaataacttcactttcaggaac
 G  E  P  P  A  I  K  D  A  V  I  T  G  N  N  F  T  F  R  N
accgtcacttacacttgcaaagaaggctatactcttgctggtcttgacaccattgaatgc
 T  V  T  Y  T  C  K  E  G  Y  T  L  A  G  L  D  T  I  E  C
ctggccgacggcaagtggagtagaagtgaccagcagtgcctggctgtctcctgtgatgag
 L  A  D  G  K  W  S  R  S  D  Q  Q  C  L  A  V  S  C  D  E
ccacccattgtggaccacgcctctccagagactgcccatcggctctttggagacattgca
 P  P  I  V  D  H  A  S  P  E  T  A  H  R  L  F  G  D  I  A
ttctactactgctctgatggttacagcctagcagacaattcccagcttctctgcaatgcc
 F  Y  Y  C  S  D  G  Y  S  L  A  D  N  S  Q  L  L  C  N  A
cagggcaagtgggtaccccagaaggtcaagacatgccccgttgtatagctcatttctgt
 Q  G  K  W  V  P  P  E  G  Q  D  M  P  R  C  I  A  H  F  C
gaaaaacctccatcggtttcctatagcatcttggaatctgtgagcaaagcaaaatttgca
 E  K  P  P  S  V  S  Y  S  I  L  E  S  V  S  K  A  K  F  A
gctggctcagttgtgagctttaaatgcatggaaggctttgtactgaacacctcagcaaag
 A  G  S  V  V  S  F  K  C  M  E  G  F  V  L  N  T  S  A  K
attgaatgtatgagaggtgggcagtggaacccttcccccatgtccatccagtgcatccct
 I  E  C  M  R  G  G  Q  W  N  P  S  P  M  S  I  Q  C  I  P
gtgcggtgtggagagccaccaagcatcatgaatggctatgcaagtggatcaaactacagt
 V  R  C  G  E  P  P  S  I  M  N  G  Y  A  S  G  S  N  Y  S
tttggagccatggtggcttacagctgcaacaaggggttctacatcaaaggggaaaagaag
 F  G  A  M  V  A  Y  S  C  N  K  G  F  Y  I  K  G  E  K  K
agcacctgcgaagccacagggcagtggagtagtcctataccgacgtgccacccggtatct
 S  T  C  E  A  T  G  Q  W  S  S  P  I  P  T  C  H  P  V  S
tgtggtgaaccacctaaggttgagaatggctttctggagcatacaactggcaggatcttt
 C  G  E  P  P  K  V  E  N  G  F  L  E  H  T  T  G  R  I  F
gagagtgaagtgaggtatcagtgtaacccgggctataagtcagtcggaagtcctgtattt
 E  S  E  V  R  Y  Q  C  N  P  G  Y  K  S  V  G  S  P  V  F
gtctgccaagccaatcgccactggcacagtgaatcccctctgatgtgtgttcctctcgac
 V  C  Q  A  N  R  H  W  H  S  E  S  P  L  M  C  V  P  L  D
```

Fig. 13A (Cont)

```
tgtggaaaacctcccccgatccagaatggcttcatgaaaggagaaaactttgaagtaggg
 C  G  K  P  P  P  I  Q  N  G  F  M  K  G  E  N  F  E  V  G
tccaaggttcagttttctgtaatgagggttatgagcttgttggtgacagttcttggaca
 S  K  V  Q  F  F  C  N  E  G  Y  E  L  V  G  D  S  S  W  T
tgtcagaaatctggcaaatggaataagaagtcaaatccaaagtgcatgcctgccaagtgc
 C  Q  K  S  G  K  W  N  K  K  S  N  P  K  C  M  P  A  K  C
ccagagccgcccctcttggaaaaccagctagtattaaaggagttgaccaccgagtagga
 P  E  P  P  L  L  E  N  Q  L  V  L  K  E  L  T  T  E  V  G
gttgtgacattttcctgtaaagaagggcatgtcctgcaaggcccctctgtcctgaaatgc
 V  V  T  F  S  C  K  E  G  H  V  L  Q  G  P  S  V  L  K  C
ttgccatcccagcaatggaatgactctttccctgtttgtaagattgttctttgtaccca
 L  P  S  Q  Q  W  N  D  S  F  P  V  C  K  I  V  L  C  T  P
cctcccctaatttcctttggtgtccccattccttcttctgctcttcattttggaagtact
 P  P  L  I  S  F  G  V  P  I  P  S  S  A  L  H  F  G  S  T
gtcaagtattcttgtgtaggtgggttttcctaagaggaaattctaccaccctctgccaa
 V  K  Y  S  C  V  G  G  F  F  L  R  G  N  S  T  T  L  C  Q
cctgatggcacctggagctctccactgccagaatgtgttccagtagaatgtccccaacct
 P  D  G  T  W  S  S  P  L  P  E  C  V  P  V  E  C  P  Q  P
gaggaaatccccaatggaatcattgatgtgcaaggccttgcctatctcagcacagctctc
 E  E  I  P  N  G  I  I  D  V  Q  G  L  A  Y  L  S  T  A  L
tatacctgcaagccaggctttgaattggtgggaaatactaccacccttgtgggagaaaat
 Y  T  C  K  P  G  F  E  L  V  G  N  T  T  T  L  C  G  E  N
ggtcactggcttggaggaaaaccaacatgtaaagccattgagtgcctgaaacccaaggag
 G  H  W  L  G  G  K  P  T  C  K  A  I  E  C  L  K  P  K  E
attttgaatggcaaattctcttacacggacctacactatggacagaccgttacctactct
 I  L  N  G  K  F  S  Y  T  D  L  H  Y  G  Q  T  V  T  Y  S
tgcaaccgaggctttcggctcgaaggtcccagtgccttgacctgtttagagacaggtgat
 C  N  R  G  F  R  L  E  G  P  S  A  L  T  C  L  E  T  G  D
tgggatgtagatgccccatcttgcaatgccatccactgtgattccccacaacccattgaa
 W  D  V  D  A  P  S  C  N  A  I  H  C  D  S  P  Q  P  I  E
aatggttttgtagaaggtgcagattacagctatggtgccataatcatctacagttgcttc
 N  G  F  V  E  G  A  D  Y  S  Y  G  A  I  I  I  Y  S  C  F
cctgggtttcaggtggctggtcatgccatgcagacctgtgaagagtcaggatggtcaagt
 P  G  F  Q  V  A  G  H  A  M  Q  T  C  E  E  S  G  W  S  S
tccatcccaacatgtatgccaatagactgtggcctccctcctcatatagattttggagac
 S  I  P  T  C  M  P  I  D  C  G  L  P  P  H  I  D  F  G  D
tgtactaaactcaaagatgaccagggatattttgagcaagaagacgacatgatggaagtt
 C  T  K  L  K  D  D  Q  G  Y  F  E  Q  E  D  D  M  M  E  V
ccatatgtgactcctcaccctccttatcatttgggagcagtggctaaaacctgggaaaat
 P  Y  V  T  P  H  P  P  Y  H  L  G  A  V  A  K  T  W  E  N
acaaaggagtctcctgctacacattcatcaaactttctgtatggtaccatggtttcatac
 T  K  E  S  P  A  T  H  S  S  N  F  L  Y  G  T  M  V  S  Y
acctgtaatccaggatatgaacttctggggaaccctgtgctgatctgccaggaagatgga
 T  C  N  P  G  Y  E  L  L  G  N  P  V  L  I  C  Q  E  D  G
acttggaatggcagtgcaccatcctgcatttcaattgaatgtgacttgcctactgctcct
 T  W  N  G  S  A  P  S  C  I  S  I  E  C  D  L  P  T  A  P
gaaaatggcttttgcgttttacagagactagcatgggaagtgctgtgcagtatagctgt
 E  N  G  F  L  R  F  T  E  T  S  M  G  S  A  V  Q  Y  S  C
aaacctggacacattctagcaggctctgacttaaggctttgtctagagaatagaaagtgg
 K  P  G  H  I  L  A  G  S  D  L  R  L  C  L  E  N  R  K  W
agtggtgcctccccacgctgtgaagccatttcatgcaaaaagccaaatccagtcatgaat
 S  G  A  S  P  R  C  E  A  I  S  C  K  K  P  N  P  V  M  N
ggatccatcaaaggaagcaactacacatacctgagcacgttgtactatgagtgtgacccc
 G  S  I  K  G  S  N  Y  T  Y  L  S  T  L  Y  Y  E  C  D  P
ggatatgtgctgaatggcactgagaggagaacatgccaggatgacaaaaactgggatgag
 G  Y  V  L  N  G  T  E  R  R  T  C  Q  D  D  K  N  W  D  E
gatgagcccatttgcattcctgtggactgcagttcaccccagtctcagccaatggccag
 D  E  P  I  C  I  P  V  D  C  S  S  P  P  V  S  A  N  G  Q
```

Fig. 13A (Cont)

```
gtgagaggagacgagtacacattccaaaaagagattgaatacacttgcaatgaagggttc
 V  R  G  D  E  Y  T  F  Q  K  E  I  E  Y  T  C  N  E  G  F
ttgcttgagggagccaggagtcgggtttgtcttgccaatggaagttggagtggagccact
 L  L  E  G  A  R  S  R  V  C  L  A  N  G  S  W  S  G  A  T
cccgactgtgtgcctgtcagatgtgccaccccgccacaactggccaatggggtgacggaa
 P  D  C  V  P  V  R  C  A  T  P  P  Q  L  A  N  G  V  T  E
ggcctggactatggcttcatgaaggaagtaacattccactgtcacgagggctacatcttg
 G  L  D  Y  G  F  M  K  E  V  T  F  H  C  H  E  G  Y  I  L
cacggtgctccaaaactcacctgtcagtcagatggcaactgggatgcagagattcctctc
 H  G  A  P  K  L  T  C  Q  S  D  G  N  W  D  A  E  I  P  L
tgtaaaccagtcaactgtggacctcctgaagatcttgcccatggtttccctaatggtttt
 C  K  P  V  N  C  G  P  P  E  D  L  A  H  G  F  P  N  G  F
tcctttattcatgggggccatatacagtatcagtgctttcctggttataagctccatgga
 S  F  I  H  G  G  H  I  Q  Y  Q  C  F  P  G  Y  K  L  H  G
aattcatcaagaaggtgcctctccaatggctcctggagtggcagctcaccttcctgcctg
 N  S  S  R  R  C  L  S  N  G  S  W  S  G  S  S  P  S  C  L
ccttgcagatgttccacaccagtaattgaatatggaactgtcaatgggacagattttgac
 P  C  R  C  S  T  P  V  I  E  Y  G  T  V  N  G  T  D  F  D
tgtggaaaggcagcccggattcagtgcttcaaaggcttcaagctcctaggactttctgaa
 C  G  K  A  A  R  I  Q  C  F  K  G  F  K  L  L  G  L  S  E
atcacctgtgaagccgatggccagtggagctctgggttcccccactgtgaacacacttct
 I  T  C  E  A  D  G  Q  W  S  S  G  F  P  H  C  E  H  T  S
tgtggttctcttccaatgataccaaatgcgttcatcagtgagaccagctcttggaaggaa
 C  G  S  L  P  M  I  P  N  A  F  I  S  E  T  S  S  W  K  E
aatgtgataacttacagctgcaggtctggatatgtcatacaaggcagttcagatctgatt
 N  V  I  T  Y  S  C  R  S  G  Y  V  I  Q  G  S  S  D  L  I
tgtacagagaaggggtatggagccagccttatccagtctgtgagcccttgtcctgtggg
 C  T  E  K  G  V  W  S  Q  P  Y  P  V  C  E  P  L  S  C  G
tccccaccgtctgtcgccaatgcagtggcaactggagaggcacacacctatgaaagtgaa
 S  P  P  S  V  A  N  A  V  A  T  G  E  A  H  T  Y  E  S  E
gtgaaactcagatgtctggaaggttatacgatggatacagatacagatacattcacctgt
 V  K  L  R  C  L  E  G  Y  T  M  D  T  D  T  D  T  F  T  C
cagaaagatggtcgctggttccctgagagaatctcctgcagtcctaaaaaatgtcctctc
 Q  K  D  G  R  W  F  P  E  R  I  S  C  S  P  K  K  C  P  L
ccggaaaacataacacatatacttgttcatggggacgatttcagtgtgaataggcaagtt
 P  E  N  I  T  H  I  L  V  H  G  D  D  F  S  V  N  R  Q  V
tctgtgtcatgtgcagaagggtatacctttgagggagttaacatatcagtatgtcagctt
 S  V  S  C  A  E  G  Y  T  F  E  G  V  N  I  S  V  C  Q  L
gatggaacctgggagccaccattctccgatgaatcttgcagtccagtttcttgtgggaaa
 D  G  T  W  E  P  P  F  S  D  E  S  C  S  P  V  S  C  G  K
cctgaaagtccagaacatggatttgtggttggcagtaaatacacctttgaaagcacgatt
 P  E  S  P  E  H  G  F  V  V  G  S  K  Y  T  F  E  S  T  I
atttatcagtgtgagcctggctatgaactagaggggaacagggaacgtgtctgccaggag
 I  Y  Q  C  E  P  G  Y  E  L  E  G  N  R  E  R  V  C  Q  E
aacagacagtggagtggaggggtggcaatatgcaaagagaccaggtgtgaaactcaactt
 N  R  Q  W  S  G  G  V  A  I  C  K  E  T  R  C  E  T  Q  L
gaatttctcaatgggaaagctgacattgaaaacaggacgactggacccaacgtggtatat
 E  F  L  N  G  K  A  D  I  E  N  R  T  T  G  P  N  V  V  Y
tcctgcaacagaggctacagtcttgaagggccatctgaggcacactgcacagaaaatgga
 S  C  N  R  G  Y  S  L  E  G  P  S  E  A  H  C  T  E  N  G
acctggagccacccagtccctctctgcaaaccaaatccatgccctgttccttttgtgatt
 T  W  S  H  P  V  P  L  C  K  P  N  P  C  P  V  P  F  V  I
cccgagaatgctctgctgtctgaaaaggagttttatgttgatcagaatgtgtccatcaaa
 P  E  N  A  L  L  S  E  K  E  F  Y  V  D  Q  N  V  S  I  K
tgtagggaaggttttctgctgcagggccacggcatcattacctacaaccccgacgagacg
 C  R  E  G  F  L  L  Q  G  H  G  I  I  T  Y  N  P  D  E  T
tggacacagacaagcgccaaatgtgaaaaaatctcatgtggtccaccggctcacgtagaa
 W  T  Q  T  S  A  K  C  E  K  I  S  C  G  P  P  A  H  V  E
```

Fig. 13A(Cont)

```
aatgcaattgctcgaggcgtacattatcaatatggagacatgatcacctactcatgttac
 N  A  I  A  R  G  V  H  Y  Q  Y  G  D  M  I  T  Y  S  C  Y
agtggatacatgttggagggtttcctgaggagtgtttgtttagaaaatggaacatggaca
 S  G  Y  M  L  E  G  F  L  R  S  V  C  L  E  N  G  T  W  T
tcacctcctatttgcagagctgtctgtcgatttccatgtcagaatgggggcatctgccaa
 S  P  P  I  C  R  A  V  C  R  F  P  C  Q  N  G  G  I  C  Q
cgcccaaatgcttgttcctgtccagagggctggatggggcgcctctgtgaagaaccaatc
 R  P  N  A  C  S  P  E  G  W  M  G  R  L  C  E  E  P  I
tgcattcttccctgtctgaacggaggtcgctgtgtggccccttaccagtgtgactgcccg
 C  I  L  P  C  L  N  G  G  R  C  V  A  P  Y  Q  C  D  C  P
cctggctggacggggtctcgctgtcatacagctgtttgccagtctccctgcttaaatggt
 P  G  W  T  G  S  R  C  H  T  A  V  C  Q  S  P  C  L  N  G
ggaaaatgtgtaagaccaaaccgatgtcactgtctttcttcttggacgggacataactgt
 G  K  C  V  R  P  N  R  C  H  C  L  S  S  W  T  G  H  N  C
tccaggaaaaggaggactgggttttaaccactgcacgaccatctggctctcccaaaagca
 S  R  K  R  R  T  G  F  -  P  L  H  D  H  L  A  L  P  K  A
ggatcatctctcctcggtagtgcctgggcatcctggaacttatgcaagaaagtccaaca
 G  S  S  L  L  G  S  A  W  A  S  W  N  L  C  K  E  S  P  T
tggtgctgggtcttgtttagtaaacttgttacttggggttacttttttatttgtgata
 W  C  W  V  L  F  S  K  L  V  T  W  G  Y  F  F  Y  F  V  I
tattttgttattccttgtgacatactttcttacatgtttccattttaaatatgcctgta
 Y  F  V  I  P  C  D  I  L  S  Y  M  F  P  F  L  N  M  P  V
ttttctatataaaaattatattaaatagatgctgctac
 F  S  I  -  K  L  Y  -  I  D  A  A
```

Predicted promoter of SEL-OB:
21001-23500bp of human genomic contig 16889828
in rev/compl orientation.
1 promoter(s) was predicted Pos.:   1302 LDF-   5.36 TATA box predicted at 1269

SEQ ID NO: 35

```
AGACGGAGTTAATCATTCATTATTACAACAGCAAACTGAGATGACT
GAATCATCAATGAATAGATGATCTGACGCAAGATTGGAAGTGAGTGA
CTCAGTTCAGTGTTACATACGTAGCTACACGTTACAGGTGTCCT
GACTCCAGCACTGGATCTTTACCAAGCCCACCTACGCCATGCAAGTG
CACTTTCTTTACAGTGGGCTCCCCCTTGAGTCTGCTTTGAA
AAACCCACCCAGCTAGCAGTTTGAAGCCAATATATCAGGTAC
ACTAAGCCAGCTGGGACTACGGATCGTAATGAATGAGAGAGAGTGA
CTGTCCTCAGAAGCCTTCCTGCCCTACTGTACCTGCTGTCTAG
CTAAGCCTCCTATTACGCCTTAATGTCACCTTCTTAATTTGT
ATGTTATATCGTTATGTCACCTTTCTTTATTTGCGTCCCA
TGGAAGAATCCCGTCGTATTTGTTCTTAATTGTAGTCCA
CATAGTCCTGCTACACATCGTATTCGGTATTCCACGCTGAGTACC
GAACAATGAATGCAGAACAACAATGAATTAATGCACGACTGAGTACGAT
```

US 7,919,602 B2

SEQUENCE LISTING

<160> NUMBER OF SEQ ID NOS: 35

<210> SEQ ID NO 1
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 1
ggattgtgtc tgtccccagt                                            20

<210> SEQ ID NO 2
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 2
ggcactaccg aggagagatg                                            20

<210> SEQ ID NO 3
<211> LENGTH: 24
<212> TYPE: DNA
<213> ORGANISM: Artificial sequence
<220> FEATURE:
<223> OTHER INFORMATION: Single strand DNA oligonucleotide

```
<400> SEQUENCE: 3
ttctcttaca cggacctaca ctat                                              24

<210> SEQ ID NO 4
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 4
tgggatggaa cttgaccat                                                    19

<210> SEQ ID NO 5
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 5
aaaccaatgt gcaaacccat                                                   20

<210> SEQ ID NO 6
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 6
ggatccatat cccagtcacc                                                   20

<210> SEQ ID NO 7
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 7
tctcttccgt gagctttcag                                                   20

<210> SEQ ID NO 8
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 8
gctggagctt gaccaccc                                                     18

<210> SEQ ID NO 9
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 9
accacagtcc atgccatcac                                                   20

<210> SEQ ID NO 10
<211> LENGTH: 20
```

```
<212> TYPE: DNA
<213> ORGANISM: Artificial sequence
<220> FEATURE:
<223> OTHER INFORMATION: Single strand DNA oligonucleotide

<400> SEQUENCE: 10
tccaccaccc tgttgctgta                                              20

<210> SEQ ID NO 11
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 11
aattactgtg gcactctcgg t                                            21

<210> SEQ ID NO 12
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 12
attccatgac accagaaccc                                              20

<210> SEQ ID NO 13
<211> LENGTH: 17
<212> TYPE: PRT
<213> ORGANISM: Artificial sequence
<220> FEATURE:
<223> OTHER INFORMATION: Synthetic peptide

<400> SEQUENCE: 13

Asp Val Asp Ala Pro Ser Cys Asn Ala Ile His Cys Asp Ser Pro Gln
1               5                   10                  15

Pro

<210> SEQ ID NO 14
<211> LENGTH: 12535
<212> TYPE: DNA
<213> ORGANISM: Homo sapiens

<400> SEQUENCE: 14
agacggagtt aaatcattca ctattagaaa cagaggaaac tgagatcact gaattccatc    60
atgaaataga tactgatgct gagccaagga ttggaagtga ctcagttcag gtggtttaca   120
taaccgtagg cttacctaca cggtgttcct gactcccagc tggaatcttt taaccaaagg   180
ccccaccctc atgcaaagtg cacctttttct ttacacgtgc gctctcccct ttggaggtct   240
tgctttggaa aaaccacccc aggtagcaac ttgtttcaaa gcagatatat gccaggtacc   300
acttaaagcc aggtggatct tatctgttga aatagatcaa gaacacatga aagggggactg   360 gggaccccct acttacactt cagacttcag cacaaacttt ctgtcctcag agaaggcttc   420
tctggcctct ccaaggtcaa gtctgtctac ctaagctctc ctttatttag catggtcact   480
tgtaattaca tatattttgt atgttaatat ctggttaatg gtcacctcac ttgttaccct   540
ttaagttcat tgaggataga atccctgtca attttttgttc cttatatttg cagtgcctca   600
catagttcct ggcacacaat gggtattcaa aaaatatttg ttaaaatcag gaaagaatga   660
acaaacagat gaatgaataa atgcacgact gaagtaccat gacaaatcat tcctgtggaa   720
```

```
cgcataaggt tagatgcaac tcctttatgg tgtgatctga gggggcccctt aagggcttaa    780
tctgcacgct cacacacacc actgattaga aatccccatc aggaaaattg tacaatcatc    840
tatttggcga gggctttggg acactgaatg ggggaaaaga aacacaaaag gtgagcaagc    900
agttttcaaa ggatgctttc aactcccctgg ccagtccgcg tgtatgtttt cgtctacaaa    960
gtgtttccaa ttactgtggc actctcggta tctggatcca tctccagtga attcctctgc   1020
agctcctgcc agacatatgg gatcaatcag ggcttcggcg ctggtgcgct tgctgcggga   1080
atgttgacag cctgacagac gcggggttct ggtgtcatgg aatctccgag cctttggctt   1140
gatcccggga ggagaatgag aggggagga gggagataga gtcacagata cagaaagtag   1200
acaggagcgg ggagagggag agagggagag aaggagggaa gcgggagatt tttcttgact   1260
gccccctttc cttcaaacat tttataggct tcagggagag agaggaggag gagagaggga   1320
agaaaaaaag aggagagcga gaggggtaga gagcgcgcgc cgttccctcc ggagttcccg   1380
agctgctgag gagtctggat tgtgtctgtc cccagtgtca gatgaaaggg cgctgaggct   1440
cttggccgct gccccgcgcc cagctccgcg cacgcccctc tgcgagtccg gccgcccagc   1500
gcctcttccc gcccgagccg ccgcctgcgc tccggggcag ccgctctgtc tccagcgcga   1560
tgtggcctcg cctggccttt tgttgctggg gtctggcgct cgtttcgggc tgggcgacct   1620
ttcagcagat gtccccgtcg cgcaatttca gcttccgcct cttccccgag accgcgcccg   1680
ggcccccggg gagtatcccc gcgccgcccg ctcctggcga cgaagcggcg gggagcagag   1740
tggagcggct gggccaggcg ttccggcgac gcgtgcggct gctgcgggag ctcagcgagc   1800
gcctggagct tgtcttcctg gtggatgatt cgtccagcgt gggcgaagtc aacttccgca   1860
gcgagctcat gttcgtccgc aagctgctgt ccgacttccc cgtggtgccc acggccacgc   1920
gcgtggccat cgtgaccttc tcgtccaaga actacgtggt gccgcgcgtc gattacatct   1980
ccacccgccg cgcgcgccag cacaagtgcg cgctgctcct caagagatcc ctgccatct   2040
cctaccgagg tggcggcacc tacaccaagg gcgccttcca gcaagccgcg caaattcttc   2100
ttcatgctag agaaaactca acaaaagttg tatttctcat cactgatgga tattccaatg   2160
ggggagaccc tagaccaatt gcagcgtcac tgcgagattc aggagtggag atcttcactt   2220
ttggcatatg gcaagggaac attcgagagc tgaatgacat ggcttccacc ccaaaggagg   2280
agcactgtta cctgctacac agttttgaag aatttgaggc tttagctcgc cgggcattgc   2340
atgaagatct accttctggg agttttattc aagatgatat ggtccactgc tcatatcttt   2400
gtgatgaagg caaggactgc tgtgaccgaa tgggaagctg caaatgtggg acacacacag   2460
gccattttga gtgcatctgt gaaaagggt attacgggaa aggtctgcag tatgaatgca   2520
cagcttgccc atcggggaca tacaaacctg aaggctcacc aggaggaatc agcagttgca   2580
ttccatgtcc tgatgaaaat cacacctctc cacctggaag cacatcccct gaagactgtg   2640
tctgcagaga gggatacagg gcatctggcc agacctgtga acttgtccac tgccctgccc   2700
tgaagcctcc cgaaaatggt tactttatcc aaaacacttg caacaaccac ttcaatgcag   2760
cctgtggggt ccgatgtcac cctggatttg atcttgtggg aagcagcatc atcttatgtc   2820
tacccaatgg tttgtggtcc ggtttagaga gctactgcag agtaagaaca tgtcctcatc   2880
tccgccagcc gaaacatggc cacatcagct gttctacaag ggaaatgtta tataagacaa   2940
catgtttggt tgcctgtgat gaagggtaca gactagaagg cagtgataag cttacttgtc   3000
aaggaaacag ccagtgggat gggccagaac ccggtgtgt ggagcgccac tgttccacct   3060
ttcagatgcc caaagatgtc atcatatccc cccacaactg tggcaagcag ccagccaaat   3120
```

```
ttgggacgat ctgctatgta agttgccgcc aagggttcat tttatctgga gtcaaagaaa    3180
tgctgagatg taccacttct ggaaaatgga atgtcggagt tcaggcagct gtgtgtaaag    3240
acgtggaggc tcctcaaatc aactgtccta aggacataga ggctaagact ctggaacagc    3300
aagattctgc caatgttacc tggcagattc aacagctaaa agacaactct ggtgaaaagg    3360
tgtcagtcca cgttcatcca gctttcaccc caccttacct tttcccaatt ggagatgttg    3420
ctatcgtata cacggcaact gacctatccg gcaaccaggc cagctgcatt tccatatca    3480 aggttattga tgcagaacca cctgtcatag actggtgcag atctccacct cccgtccagg    3540
tctcggagaa ggtacatgcc gcaagctggg atgagcctca gttctcagac aactcagggg    3600
ctgaattggt cattaccaga agtcatacac aaggagacct tttccctcaa ggggagacta    3660
tagtacagta tacggccact gaccctcag gcaataacag gacatgtgat atccatattg    3720
tcataaaagg ttctccctgt gaaattccat tcacacctgt aaatggggat tttatatgca    3780
ctccagataa tactgagtc aactgtacat taacttgctt ggagggctat gatttcacag    3840
aagggtctac tgacaagtat tattgtgctt atgaagatgg cgtctggaaa ccaacatata    3900
ccactgaatg gccagactgt gccaaaaaac gttttgcaaa ccacgggttc aagtcctttg    3960
agatgttcta caaagcagct cgttgtgatg acacagatct gatgaagaag ttttctgaag    4020
catttgagac gaccctggga aaaatggtcc catcattttg tagtgatgca gaggacattg    4080
actggagact ggaggagaac ctgaccaaaa aatattgcct agaatataat tatgactatg    4140
aaaatggctt tgcaattgga ccaggtggct gggtgcagc taataggctg gattactctt    4200
acgatgactt cctggacact gtgcaagaaa cagccacaag catcggcaat gccaagtcct    4260
cacggattaa aagaagtgcc ccattatctg actataaaat taagttaatt tttaacatca    4320
cagctagtgt gccattaccc gatgaaagaa atgataccct tgaatgggaa aatcagcaac    4380
gactccttca gacattggaa actatcacaa ataaactgaa aaggactctc aacaaagacc    4440
ccatgtattc cttcagctt gcatcagaaa tacttatagc cgacagcaat tcattaggaa    4500
caaaaaaggc ttccccttc tgcagaccag gctcagtgct gagagggcgt atgtgtgtca    4560
attgcccttt gggaacctat tataatctgg aacatttcac ctgtgaaagc tgccggatcg    4620
gatcctatca agatgaagaa gggcaacttg agtgcaagct tgccccctct gggatgtaca    4680
cggaatatat ccattcaaga aacatctctg attgtaaagc tcagtgtaaa caaggcacct    4740
actcatgcag tggacttgag acttgtgaat cgtgtccact gggcacttat cagccaaaat    4800
ttggttcccg gagctgcctc tcgtgtccag aaaacacctc aactgtgaaa agaggagccg    4860
tgaacatttc tgcatgtgga gttccttgtc cagaaggaaa attctcgcgt tctgggttaa    4920
tgccctgtca cccatgtcct cgtgactatt accaacctaa tgcagggaag gccttctgcc    4980
tggcctgtcc cttttatgga actaccccat tcgctggttc cagatccatc acagaatgtt    5040
caagttttag ttcaacttc tcagcggcag aggaaagtgt ggtgcccct gcctctcttg    5100 gacatattaa aaagaggcat gaaatcagca gtcaggtttt ccatgaatgc ttctttaacc    5160
cttgccacaa tagtggaacc tgccagcaac ttggcgtgg ttatgtttgt ctctgtccac    5220
ttggatatac aggcttaaag tgtgaaacag acatcgatga gtgcagccca ctgccttgcc    5280
tcaacaatgg agtttgtaaa gaccctagtt ggggaattcat ttgtgagtgc ccatcaggtt    5340
acacaggtca gcggtgtgaa gaaaatatca atgagtgtag ctccagtcct tgtttaaata    5400
aaggaatctg tgttgatggt gtggctggct atcgttgcac atgtgtgaaa ggatttgtag    5460
gcctgcattg tgaaacagaa gtcaatgaat gccagtcaaa cccatgctta aataatgcag    5520
```

```
tctgtgaaga ccaggttggg ggattcttgt gcaaatgccc acctggattt ttgggtaccc    5580
gatgtggaaa gaacgtcgat gagtgtctca gtcagccatg caaaaatgga gctacctgta    5640
aagacggtgc caatagcttc agatgcctgt gtgcagctgg cttcacagga tcacactgtg    5700
aattgaacat caatgaatgt cagtctaatc catgtagaaa tcaggccacc tgtgtggatg    5760
aattaaattc atacagttgt aaatgtcagc caggattttc aggcaaaagg tgtgaaacag    5820
aacagtctac aggctttaac ctggattttg aagtttctgg catctatgga tatgtcatgc    5880
tagttggcat gctcccatct ctccatgctc taacctgtac cttctggatg aaatcctctg    5940
acgacatgaa ctatggaaca ccaatctcct atgcagttga taacggcagc gacaatacct    6000
tgctcctgac tgattataac ggctgggttc tttatgtgaa tggcagggaa aagataacaa    6060
actgtccctc ggtgaatgat ggcagatggc atcatattgc aatcacttgg acaagtgcca    6120
atggcatctg gaaagtctat atcgatggga aattatctga cggtggtgct ggcctctctg    6180
ttggtttgcc catacctggt atgtttgtg gtggtgcgtt agttctgggg caagagcaag    6240
acaaaaaagg agagggattc agcccagctg agtctttgt gggctccata gccagctca    6300 acctctggga ctatgtcctg tctccacagc aggtgaagtc actggctacc tcctgcccag    6360
aggaactcag taaggaaac gtgttagcat ggcctgattt cttgtcagga attgtgggga    6420
aagtgaagat cgattctaag agcatatttt gttctgattg cccacgctta ggagggtcag    6480
tgcctcatct gagaactgca tctgaagatt aaagccagg ttccaaagtc aatctgttct    6540
gtgatccagg cttccagctg gtcgggaacc ctgtgcagta ctgtctgaat caaggacagt    6600
ggacacaacc acttcctcac tgtgaacgca ttagctgtgg ggtgccacct cctttggaga    6660
atggcttcca ttcagccgat gacttctatg ctggcagcac agtaacctac cagtgcaaca    6720
atggctacta tctattgggt gactcaagga tgttctgtac agataatggg agctggaacg    6780
gcgtttcacc atcctgcctt gatgtcgatg agtgtgcagt tggatcagat tgtagtgagc    6840
atgcttcttg cctgaacgta gatggatcct acatatgttc atgtgtcccc tcgtacacag    6900
gagatgggaa aaactgtgca gaacctataa aatgtaaggc tccaggaaat ccggaaaatg    6960
gccactcctc aggtgagatt tatacagtag gtgccgaagt cacattttcg tgtcaggaag    7020
gataccagtt gatgggagta accaaaatca catgtttgga gtctggagaa tggaatcatc    7080
taataccata ttgtaaagct gttttcatgtg gtaaaccggc tattccagaa aatggttgca    7140
ttgaggagtt agcatttact tttggcagca agtgacata taggtgtaat aaaggatata    7200
ctctggccgg tgataaagaa tcatcctgtc ttgctaacag ttcttggagt cattcccctc    7260
ctgtgtgtga accagtgaag tgttctagtc cggaaaatat aaataatgga aaatatattt    7320
tgagtgggct tacctacctt tctactgcat catattcatg cgatacagga tacagcttac    7380
agggcccttc cattattgaa tgcacggctt ctggcatctg gacagagcg ccacctgcct    7440 gtcacctcgt cttctgtgga gaaccacctg ccatcaaaga tgctgtcatt acggggaata    7500
acttcacttt caggaacacc gtcacttaca cttgcaaaga aggctatact cttgctggtc    7560
ttgacaccat tgaatgcctg ccgacggca agtggagtag aagtgaccag cagtgcctgg    7620
ctgtctcctg tgatgagcca cccattgtgg accacgcctc tccagagact gcccatcggc    7680
tctttggaga cattgcattc tactactgct ctgatggtta cagcctagca gacaattccc    7740
agcttctctg caatgcccag ggcaagtggg tacccccaga aggtcaagac atgccccgtt    7800
gtatagctca tttctgtgaa aaactccat cggtttccta tagcatcttg gaatctgtga    7860
gcaaagcaaa atttgcagct ggctcagttg tgagctttaa atgcatggaa ggctttgtac    7920
```

```
tgaacacctc agcaaagatt gaatgtatga gaggtgggca gtggaaccct tcccccatgt    7980
ccatccagtg catccctgtg cggtgtggag agccaccaag catcatgaat ggctatgcaa    8040
gtggatcaaa ctacagtttt ggagccatgg tggcttacag ctgcaacaag gggttctaca    8100
tcaaagggga aaagaagagc acctgcgaag ccacagggca gtggagtagt cctataccga    8160
cgtgccaccc ggtatcttgt ggtgaaccac ctaaggttga aatggctttt ctggagcata    8220
caactggcag atctttgag agtgaagtga ggtatcagtg taacccgggc tataagtcag    8280
tcggaagtcc tgtatttgtc tgccaagcca atcgccactg cacagtgaa tcccctctga    8340
tgtgtgttcc tctcgactgt ggaaaacctc ccccgatcca gaatggcttc atgaaaggag    8400
aaaactttga agtagggtcc aaggttcagt ttttctgtaa tgagggttat gagcttgttg    8460
gtgacagttc ttggacatgt cagaaatctg gcaaatggaa taagaagtca aatccaaagt    8520
gcatgcctgc caagtgccca gagccgcccc tcttggaaaa ccagctagta ttaaaggagt    8580
tgaccaccga ggtaggagtt gtgacatttt cctgtaaaga agggcatgtc ctgcaaggcc    8640
cctctgtcct gaaatgcttg ccatcccagc aatggaatga ctctttccct gtttgtaaga    8700
ttgttctttg tacccacct cccctaattt ccttttggtgt ccccattcct tcttctgctc    8760
ttcattttgg aagtactgtc aagtattctt gtgtaggtgg gttttttccta agaggaaatt    8820
ctaccaccct ctgccaacct gatggcacct ggagctctcc actgccagaa tgtgttccag    8880
tagaatgtcc ccaacctgag gaaatcccca atggaatcat tgatgtgcaa ggccttgcct    8940
atctcagcac agctctctat acctgcaagc caggctttga attggtggga aatactacca    9000
cccttttgtgg agaaaatggt cactggcttg gaggaaaacc aacatgtaaa gccattgagt    9060
gcctgaaacc caaggagatt ttgaatggca aattctctta cacggaccta cactatggac    9120
agaccgttac ctactcttgc aaccgaggct ttcggctcga aggtcccagt gccttgacct    9180
gtttagagac aggtgattgg gatgtagatg ccccatcttg caatgccatc cactgtgatt    9240
ccccacaacc cattgaaaat ggttttgtag aaggtgcaga ttacagctat ggtgccataa    9300
tcatctacag ttgcttccct gggtttcagg tggctggtca tgccatgcag acctgtgaag    9360
agtcaggatg gtcaagttcc atcccaacat gtatgccaat agactgtggc ctccctcctc    9420
atatagattt tggagactgt actaaactca agatgacca gggatatttt gagcaagaag    9480
acgacatgat ggaagttcca tatgtgactc ctcaccctcc ttatcatttg ggagcagtgg    9540
ctaaaacctg ggaaaataca aaggagtctc ctgctacaca ttcatcaaac tttctgtatg    9600
gtaccatggt ttcatacacc tgtaatccag gatatgaact tctggggaac cctgtgctga    9660
tctgccagga agatggaact tggaatggca gtgcaccatc ctgcatttca attgaatgtg    9720
acttgcctac tgctcctgaa aatggctttt tgcgttttac agagactagc atgggaagtg    9780
ctgtgcagta tagctgtaaa cctggacaca ttctagcagg ctctgactta aggctttgtc    9840
tagagaatag aaagtggagt ggtgcctccc cacgctgtga agccatttca tgcaaaaagc    9900
caaatccagt catgaatgga tccatcaaag aagcaacta cacatacctg agcacgttgt    9960
actatgagtg tgaccccgga tatgtgctga atggcactga ggagaaaca tgccaggatg    10020
acaaaaactg ggatgaggat gagcccattt gcattcctgt ggactgcagt tcaccccag    10080
tctcagccaa tggccaggtg agaggagacg agtacacatt ccaaaaagag attgaataca    10140
cttgcaatga agggttcttg cttgagggag ccaggagtcg ggtttgtctt gccaatggaa    10200
gttggagtgg agccactccc gactgtgtgc ctgtcagatg tgccacccg ccacaactgg    10260
ccaatggggt gacggaaggc ctggactatg gcttcatgaa ggaagtaaca ttccactgtc    10320
```

```
acgagggcta catcttgcac ggtgctccaa aactcacctg tcagtcagat ggcaactggg    10380
atgcagagat tcctctctgt aaaccagtca actgtggacc tcctgaagat cttgcccatg    10440
gtttccctaa tggtttttcc tttattcatg ggggccatat acagtatcag tgctttcctg    10500
gttataagct ccatggaaat tcatcaagaa ggtgcctctc caatggctcc tggagtggca    10560
gctcaccttc ctgcctgcct tgcagatgtt ccacaccagt aattgaatat ggaactgtca    10620
atgggacaga ttttgactgt ggaaaggcag cccggattca gtgcttcaaa ggcttcaagc    10680
tcctaggact ttctgaaatc acctgtgaag ccgatggcca gtggagctct gggttccccc    10740
actgtgaaca cacttcttgt ggttctcttc aatgatacc aaatgcgttc atcagtgaga    10800
ccagctcttg gaaggaaaat gtgataactt acagctgcag gtctggatat gtcatacaag    10860
gcagttcaga tctgatttgt acagagaaag gggtatggag ccagccttat ccagtctgtg    10920
agcccttgtc ctgtgggtcc ccaccgtctg tcgccaatgc agtggcaact ggagaggcac    10980
acacctatga agtgaagtg aaactcagat gtctggaagg ttatacgatg gatacagata    11040
cagatacatt cacctgtcag aaagatggtc gctggttccc tgagagaatc tcctgcagtc    11100
ctaaaaaatg tcctctcccg gaaaacataa cacatatact tgttcatggg gacgatttca    11160
gtgtgaatag gcaagtttct gtgtcatgtg cagaagggta tacctttgag ggagttaaca    11220
tatcagtatg tcagcttgat ggaacctggg agccaccatt ctccgatgaa tcttgcagtc    11280
cagtttcttg tgggaaacct gaaagtccag aacatggatt tgtggttggc agtaaataca    11340
cctttgaaag cacgattatt tatcagtgtg agcctggcta tgaactagag gggaacaggg    11400
aacgtgtctg ccaggagaac agacagtgga gtggagggg ggcaatatgc aaagagacca    11460
ggtgtgaaac tcaacttgaa tttctcaatg ggaaagctga cattgaaaac aggacgactg    11520
gacccaacgt ggtatattcc tgcaacagag gctacagtct tgaagggcca tctgaggcac    11580
actgcacaga aaatggaacc tggagccacc cagtccctct ctgcaaacca aatccatgcc    11640
ctgttccttt tgtgattccc gagaatgctc tgctgtctga aaaggagttt tatgttgatc    11700
agaatgtgtc catcaaatgt agggaaggtt ttctgctgca gggccacggc atcattacct    11760
acaaccccga cgagacgtgg acacagacaa gcgccaaatg tgaaaaatc tcatgtggtc    11820
caccggctca cgtagaaaat gcaattgctc gaggcgtaca ttatcaatat ggagacatga    11880
tcacctactc atgttacagt ggatacatgt tgaggggttt cctgaggagt gtttgtttag    11940
aaaatggaac atggacatca cctcctatt gcagagctgt ctgtcgattt ccatgtcaga    12000
atgggggcat ctgccaacgc ccaaatgctt gttcctgtcc agagggctgg atggggcgcc    12060
tctgtgaaga accaatctgc attcttccct gtctgaacgg aggtcgctgt gtggcccctt    12120
accagtgtga ctgcccgcct ggctggacgg ggtctcgctg tcatacagct gtttgccagt    12180
ctccctgctt aaatggtgga aaatgtgtaa gaccaaaccg atgtcactgt ctttcttctt    12240
ggacgggaca taactgttcc aggaaaagga ggactgggtt ttaaccactg cacgaccatc    12300
tggctctccc aaaagcagga tcatctctcc tcggtagtgc ctgggcatcc tggaacttat    12360
gcaaagaaag tccaacatgg tgctgggtct tgtttagtaa acttgttact tggggttact    12420
ttttttattt tgtgatatat tttgttattc cttgtgacat actttcttac atgtttccat    12480
ttttaaatat gcctgtattt tctatataaa aattatatta aatagatgct gctac        12535
```

<210> SEQ ID NO 15
<211> LENGTH: 3574
<212> TYPE: PRT
<213> ORGANISM: Homo sapiens

```
<400> SEQUENCE: 15

Met Trp Pro Arg Leu Ala Phe Cys Cys Trp Gly Leu Ala Leu Val Ser
1               5                   10                  15

Gly Trp Ala Thr Phe Gln Gln Met Ser Pro Ser Arg Asn Phe Ser Phe
            20                  25                  30

Arg Leu Phe Pro Glu Thr Ala Pro Gly Ala Pro Gly Ser Ile Pro Ala
        35                  40                  45

Pro Pro Ala Pro Gly Asp Glu Ala Ala Gly Ser Arg Val Glu Arg Leu
    50                  55                  60

Gly Gln Ala Phe Arg Arg Arg Val Arg Leu Leu Arg Glu Leu Ser Glu
65                  70                  75                  80

Arg Leu Glu Leu Val Phe Leu Val Asp Asp Ser Ser Val Gly Glu
                85                  90                  95

Val Asn Phe Arg Ser Glu Leu Met Phe Val Arg Lys Leu Leu Ser Asp
                100                 105                 110

Phe Pro Val Val Pro Thr Ala Thr Arg Val Ala Ile Val Thr Phe Ser
            115                 120                 125

Ser Lys Asn Tyr Val Val Pro Arg Val Asp Tyr Ile Ser Thr Arg Arg
130                 135                 140

Ala Arg Gln His Lys Cys Ala Leu Leu Leu Gln Glu Ile Pro Ala Ile
145                 150                 155                 160

Ser Tyr Arg Gly Gly Thr Tyr Thr Lys Gly Ala Phe Gln Gln Ala
                165                 170                 175

Ala Gln Ile Leu Leu His Ala Arg Glu Asn Ser Thr Lys Val Val Phe
            180                 185                 190

Leu Ile Thr Asp Gly Tyr Ser Asn Gly Gly Asp Pro Arg Pro Ile Ala
        195                 200                 205

Ala Ser Leu Arg Asp Ser Gly Val Glu Ile Phe Thr Phe Gly Ile Trp
    210                 215                 220

Gln Gly Asn Ile Arg Glu Leu Asn Asp Met Ala Ser Thr Pro Lys Glu
225                 230                 235                 240

Glu His Cys Tyr Leu Leu His Ser Phe Glu Glu Phe Glu Ala Leu Ala
                245                 250                 255

Arg Arg Ala Leu His Glu Asp Leu Pro Ser Gly Ser Phe Ile Gln Asp
            260                 265                 270

Asp Met Val His Cys Ser Tyr Leu Cys Asp Glu Gly Lys Asp Cys Cys
        275                 280                 285

Asp Arg Met Gly Ser Cys Lys Cys Gly Thr His Thr Gly His Phe Glu
    290                 295                 300

Cys Ile Cys Glu Lys Gly Tyr Tyr Gly Lys Gly Leu Gln Tyr Glu Cys
305                 310                 315                 320

Thr Ala Cys Pro Ser Gly Thr Tyr Lys Pro Glu Gly Ser Pro Gly Gly
                325                 330                 335

Ile Ser Ser Cys Ile Pro Cys Pro Asp Glu Asn His Thr Ser Pro Pro
            340                 345                 350

Gly Ser Thr Ser Pro Glu Asp Cys Val Cys Arg Glu Gly Tyr Arg Ala
        355                 360                 365

Ser Gly Gln Thr Cys Glu Leu Val His Cys Pro Ala Leu Lys Pro Pro
    370                 375                 380

Glu Asn Gly Tyr Phe Ile Gln Asn Thr Cys Asn Asn His Phe Asn Ala
385                 390                 395                 400

Ala Cys Gly Val Arg Cys His Pro Gly Phe Asp Leu Val Gly Ser Ser
                405                 410                 415
```

-continued

```
Ile Ile Leu Cys Leu Pro Asn Gly Leu Trp Ser Gly Leu Glu Ser Tyr
            420                 425                 430

Cys Arg Val Arg Thr Cys Pro His Leu Arg Gln Pro Lys His Gly His
        435                 440                 445

Ile Ser Cys Ser Thr Arg Glu Met Leu Tyr Lys Thr Thr Cys Leu Val
    450                 455                 460

Ala Cys Asp Glu Gly Tyr Arg Leu Glu Gly Ser Asp Lys Leu Thr Cys
465                 470                 475                 480

Gln Gly Asn Ser Gln Trp Asp Gly Pro Glu Pro Arg Cys Val Glu Arg
                485                 490                 495

His Cys Ser Thr Phe Gln Met Pro Lys Asp Val Ile Ile Ser Pro His
            500                 505                 510

Asn Cys Gly Lys Gln Pro Ala Lys Phe Gly Thr Ile Cys Tyr Val Ser
        515                 520                 525

Cys Arg Gln Gly Phe Ile Leu Ser Gly Val Lys Glu Met Leu Arg Cys
    530                 535                 540

Thr Thr Ser Gly Lys Trp Asn Val Gly Val Gln Ala Ala Val Cys Lys
545                 550                 555                 560

Asp Val Glu Ala Pro Gln Ile Asn Cys Pro Lys Asp Ile Glu Ala Lys
                565                 570                 575

Thr Leu Glu Gln Gln Asp Ser Ala Asn Val Thr Trp Gln Ile Pro Thr
            580                 585                 590

Ala Lys Asp Asn Ser Gly Glu Lys Val Ser Val His Val His Pro Ala
        595                 600                 605

Phe Thr Pro Pro Tyr Leu Phe Pro Ile Gly Asp Val Ala Ile Val Tyr
    610                 615                 620

Thr Ala Thr Asp Leu Ser Gly Asn Gln Ala Ser Cys Ile Phe His Ile
625                 630                 635                 640

Lys Val Ile Asp Ala Glu Pro Pro Val Ile Asp Trp Cys Arg Ser Pro
                645                 650                 655

Pro Pro Val Gln Val Ser Glu Lys Val His Ala Ala Ser Trp Asp Glu
            660                 665                 670

Pro Gln Phe Ser Asp Asn Ser Gly Ala Glu Leu Val Ile Thr Arg Ser
        675                 680                 685

His Thr Gln Gly Asp Leu Phe Pro Gln Gly Glu Thr Ile Val Gln Tyr
    690                 695                 700

Thr Ala Thr Asp Pro Ser Gly Asn Asn Arg Thr Cys Asp Ile His Ile
705                 710                 715                 720

Val Ile Lys Gly Ser Pro Cys Glu Ile Pro Phe Thr Pro Val Asn Gly
                725                 730                 735

Asp Phe Ile Cys Thr Pro Asp Asn Thr Gly Val Asn Cys Thr Leu Thr
            740                 745                 750

Cys Leu Glu Gly Tyr Asp Phe Thr Glu Gly Ser Thr Asp Lys Tyr Tyr
        755                 760                 765

Cys Ala Tyr Glu Asp Gly Val Trp Lys Pro Thr Tyr Thr Thr Glu Trp
    770                 775                 780

Pro Asp Cys Ala Lys Lys Arg Phe Ala Asn His Gly Phe Lys Ser Phe
785                 790                 795                 800

Glu Met Phe Tyr Lys Ala Ala Arg Cys Asp Thr Asp Leu Met Lys
                805                 810                 815

Lys Phe Ser Glu Ala Phe Glu Thr Thr Leu Gly Lys Met Val Pro Ser
            820                 825                 830

Phe Cys Ser Asp Ala Glu Asp Ile Asp Trp Arg Leu Glu Glu Asn Leu
        835                 840                 845
```

```
Thr Lys Lys Tyr Cys Leu Glu Tyr Asn Tyr Asp Tyr Glu Asn Gly Phe
    850             855             860

Ala Ile Gly Pro Gly Gly Trp Gly Ala Ala Asn Arg Leu Asp Tyr Ser
865             870             875             880

Tyr Asp Asp Phe Leu Asp Thr Val Gln Glu Thr Ala Thr Ser Ile Gly
                885             890             895

Asn Ala Lys Ser Ser Arg Ile Lys Arg Ser Ala Pro Leu Ser Asp Tyr
            900             905             910

Lys Ile Lys Leu Ile Phe Asn Ile Thr Ala Ser Val Pro Leu Pro Asp
        915             920             925

Glu Arg Asn Asp Thr Leu Glu Trp Glu Asn Gln Gln Arg Leu Leu Gln
    930             935             940

Thr Leu Glu Thr Ile Thr Asn Lys Leu Lys Arg Thr Leu Asn Lys Asp
945             950             955             960

Pro Met Tyr Ser Phe Gln Leu Ala Ser Glu Ile Leu Ile Ala Asp Ser
                965             970             975

Asn Ser Leu Gly Thr Lys Lys Ala Ser Pro Phe Cys Arg Pro Gly Ser
            980             985             990

Val Leu Arg Gly Arg Met Cys Val Asn Cys Pro Leu Gly Thr Tyr Tyr
        995             1000            1005

Asn Leu Glu His Phe Thr Cys Glu Ser Cys Arg Ile Gly Ser Tyr
    1010            1015            1020

Gln Asp Glu Glu Gly Gln Leu Glu Cys Lys Leu Cys Pro Ser Gly
    1025            1030            1035

Met Tyr Thr Glu Tyr Ile His Ser Arg Asn Ile Ser Asp Cys Lys
    1040            1045            1050

Ala Gln Cys Lys Gln Gly Thr Tyr Ser Cys Ser Gly Leu Glu Thr
    1055            1060            1065

Cys Glu Ser Cys Pro Leu Gly Thr Tyr Gln Pro Lys Phe Gly Ser
    1070            1075            1080

Arg Ser Cys Leu Ser Cys Pro Glu Asn Thr Ser Thr Val Lys Arg
    1085            1090            1095

Gly Ala Val Asn Ile Ser Ala Cys Gly Val Pro Cys Pro Glu Gly
    1100            1105            1110

Lys Phe Ser Arg Ser Gly Leu Met Pro Cys His Pro Cys Pro Arg
    1115            1120            1125

Asp Tyr Tyr Gln Pro Asn Ala Gly Lys Ala Phe Cys Leu Ala Cys
    1130            1135            1140

Pro Phe Tyr Gly Thr Thr Pro Phe Ala Gly Ser Arg Ser Ile Thr
    1145            1150            1155

Glu Cys Ser Ser Phe Ser Ser Thr Phe Ser Ala Ala Glu Glu Ser
    1160            1165            1170

Val Val Pro Pro Ala Ser Leu Gly His Ile Lys Lys Arg His Glu
    1175            1180            1185

Ile Ser Ser Gln Val Phe His Glu Cys Phe Phe Asn Pro Cys His
    1190            1195            1200

Asn Ser Gly Thr Cys Gln Gln Leu Gly Arg Gly Tyr Val Cys Leu
    1205            1210            1215

Cys Pro Leu Gly Tyr Thr Gly Leu Lys Cys Glu Thr Asp Ile Asp
    1220            1225            1230

Glu Cys Ser Pro Leu Pro Cys Leu Asn Asn Gly Val Cys Lys Asp
    1235            1240            1245

Leu Val Gly Glu Phe Ile Cys Glu Cys Pro Ser Gly Tyr Thr Gly
```

```
                    1250              1255              1260

Gln Arg Cys Glu Glu Asn Ile Asn Glu Cys Ser Ser Ser Pro Cys
    1265              1270              1275

Leu Asn Lys Gly Ile Cys Val Asp Gly Val Ala Gly Tyr Arg Cys
    1280              1285              1290

Thr Cys Val Lys Gly Phe Val Gly Leu His Cys Glu Thr Glu Val
    1295              1300              1305

Asn Glu Cys Gln Ser Asn Pro Cys Leu Asn Asn Ala Val Cys Glu
    1310              1315              1320

Asp Gln Val Gly Gly Phe Leu Cys Lys Cys Pro Pro Gly Phe Leu
    1325              1330              1335

Gly Thr Arg Cys Gly Lys Asn Val Asp Glu Cys Leu Ser Gln Pro
    1340              1345              1350

Cys Lys Asn Gly Ala Thr Cys Lys Asp Gly Ala Asn Ser Phe Arg
    1355              1360              1365

Cys Leu Cys Ala Ala Gly Phe Thr Gly Ser His Cys Glu Leu Asn
    1370              1375              1380

Ile Asn Glu Cys Gln Ser Asn Pro Cys Arg Asn Gln Ala Thr Cys
    1385              1390              1395

Val Asp Glu Leu Asn Ser Tyr Ser Cys Lys Cys Gln Pro Gly Phe
    1400              1405              1410

Ser Gly Lys Arg Cys Glu Thr Glu Gln Ser Thr Gly Phe Asn Leu
    1415              1420              1425

Asp Phe Glu Val Ser Gly Ile Tyr Gly Tyr Val Met Leu Val Gly
    1430              1435              1440

Met Leu Pro Ser Leu His Ala Leu Thr Cys Thr Phe Trp Met Lys
    1445              1450              1455

Ser Ser Asp Asp Met Asn Tyr Gly Thr Pro Ile Ser Tyr Ala Val
    1460              1465              1470

Asp Asn Gly Ser Asp Asn Thr Leu Leu Leu Thr Asp Tyr Asn Gly
    1475              1480              1485

Trp Val Leu Tyr Val Asn Gly Arg Glu Lys Ile Thr Asn Cys Pro
    1490              1495              1500

Ser Val Asn Asp Gly Arg Trp His His Ile Ala Ile Thr Trp Thr
    1505              1510              1515

Ser Ala Asn Gly Ile Trp Lys Val Tyr Ile Asp Gly Lys Leu Ser
    1520              1525              1530

Asp Gly Gly Ala Gly Leu Ser Val Gly Leu Pro Ile Pro Gly Met
    1535              1540              1545

Phe Gly Gly Ala Leu Val Leu Gly Gln Glu Gln Asp Lys Lys
    1550              1555              1560

Gly Glu Gly Phe Ser Pro Ala Glu Ser Phe Val Gly Ser Ile Ser
    1565              1570              1575

Gln Leu Asn Leu Trp Asp Tyr Val Leu Ser Pro Gln Val Lys
    1580              1585              1590

Ser Leu Ala Thr Ser Cys Pro Glu Glu Leu Ser Lys Gly Asn Val
    1595              1600              1605

Leu Ala Trp Pro Asp Phe Leu Ser Gly Ile Val Gly Lys Val Lys
    1610              1615              1620

Ile Asp Ser Lys Ser Ile Phe Cys Ser Asp Cys Pro Arg Leu Gly
    1625              1630              1635

Gly Ser Val Pro His Leu Arg Thr Ala Ser Glu Asp Leu Lys Pro
    1640              1645              1650
```

-continued

```
Gly Ser Lys Val Asn Leu Phe Cys Asp Pro Gly Phe Gln Leu Val
1655             1660                1665

Gly Asn Pro Val Gln Tyr Cys Leu Asn Gln Gly Gln Trp Thr Gln
1670             1675                1680

Pro Leu Pro His Cys Glu Arg Ile Ser Cys Gly Val Pro Pro Pro
1685             1690                1695

Leu Glu Asn Gly Phe His Ser Ala Asp Asp Phe Tyr Ala Gly Ser
1700             1705                1710

Thr Val Thr Tyr Gln Cys Asn Asn Gly Tyr Tyr Leu Leu Gly Asp
1715             1720                1725

Ser Arg Met Phe Cys Thr Asp Asn Gly Ser Trp Asn Gly Val Ser
1730             1735                1740

Pro Ser Cys Leu Asp Val Asp Glu Cys Ala Val Gly Ser Asp Cys
1745             1750                1755

Ser Glu His Ala Ser Cys Leu Asn Val Asp Gly Ser Tyr Ile Cys
1760             1765                1770

Ser Cys Val Pro Ser Tyr Thr Gly Asp Gly Lys Asn Cys Ala Glu
1775             1780                1785

Pro Ile Lys Cys Lys Ala Pro Gly Asn Pro Glu Asn Gly His Ser
1790             1795                1800

Ser Gly Glu Ile Tyr Thr Val Gly Ala Glu Val Thr Phe Ser Cys
1805             1810                1815

Gln Glu Gly Tyr Gln Leu Met Gly Val Thr Lys Ile Thr Cys Leu
1820             1825                1830

Glu Ser Gly Glu Trp Asn His Leu Ile Pro Tyr Cys Lys Ala Val
1835             1840                1845

Ser Cys Gly Lys Pro Ala Ile Pro Glu Asn Gly Cys Ile Glu Glu
1850             1855                1860

Leu Ala Phe Thr Phe Gly Ser Lys Val Thr Tyr Arg Cys Asn Lys
1865             1870                1875

Gly Tyr Thr Leu Ala Gly Asp Lys Glu Ser Ser Cys Leu Ala Asn
1880             1885                1890

Ser Ser Trp Ser His Ser Pro Pro Val Cys Glu Pro Val Lys Cys
1895             1900                1905

Ser Ser Pro Glu Asn Ile Asn Asn Gly Lys Tyr Ile Leu Ser Gly
1910             1915                1920

Leu Thr Tyr Leu Ser Thr Ala Ser Tyr Ser Cys Asp Thr Gly Tyr
1925             1930                1935

Ser Leu Gln Gly Pro Ser Ile Ile Glu Cys Thr Ala Ser Gly Ile
1940             1945                1950

Trp Asp Arg Ala Pro Pro Ala Cys His Leu Val Phe Cys Gly Glu
1955             1960                1965

Pro Pro Ala Ile Lys Asp Ala Val Ile Thr Gly Asn Asn Phe Thr
1970             1975                1980

Phe Arg Asn Thr Val Thr Tyr Thr Cys Lys Glu Gly Tyr Thr Leu
1985             1990                1995

Ala Gly Leu Asp Thr Ile Glu Cys Leu Ala Asp Gly Lys Trp Ser
2000             2005                2010

Arg Ser Asp Gln Gln Cys Leu Ala Val Ser Cys Asp Glu Pro Pro
2015             2020                2025

Ile Val Asp His Ala Ser Pro Glu Thr Ala His Arg Leu Phe Gly
2030             2035                2040

Asp Ile Ala Phe Tyr Tyr Cys Ser Asp Gly Tyr Ser Leu Ala Asp
2045             2050                2055
```

```
Asn Ser Gln Leu Leu Cys Asn Ala Gln Gly Lys Trp Val Pro Pro
    2060                2065                2070

Glu Gly Gln Asp Met Pro Arg Cys Ile Ala His Phe Cys Glu Lys
    2075                2080                2085

Pro Pro Ser Val Ser Tyr Ser Ile Leu Glu Ser Val Ser Lys Ala
    2090                2095                2100

Lys Phe Ala Ala Gly Ser Val Val Ser Phe Lys Cys Met Glu Gly
    2105                2110                2115

Phe Val Leu Asn Thr Ser Ala Lys Ile Glu Cys Met Arg Gly Gly
    2120                2125                2130

Gln Trp Asn Pro Ser Pro Met Ser Ile Gln Cys Ile Pro Val Arg
    2135                2140                2145

Cys Gly Glu Pro Pro Ser Ile Met Asn Gly Tyr Ala Ser Gly Ser
    2150                2155                2160

Asn Tyr Ser Phe Gly Ala Met Val Ala Tyr Ser Cys Asn Lys Gly
    2165                2170                2175

Phe Tyr Ile Lys Gly Glu Lys Lys Ser Thr Cys Glu Ala Thr Gly
    2180                2185                2190

Gln Trp Ser Ser Pro Ile Pro Thr Cys His Pro Val Ser Cys Gly
    2195                2200                2205

Glu Pro Pro Lys Val Glu Asn Gly Phe Leu Glu His Thr Thr Gly
    2210                2215                2220

Arg Ile Phe Glu Ser Glu Val Arg Tyr Gln Cys Asn Pro Gly Tyr
    2225                2230                2235

Lys Ser Val Gly Ser Pro Val Phe Val Cys Gln Ala Asn Arg His
    2240                2245                2250

Trp His Ser Glu Ser Pro Leu Met Cys Val Pro Leu Asp Cys Gly
    2255                2260                2265

Lys Pro Pro Pro Ile Gln Asn Gly Phe Met Lys Gly Glu Asn Phe
    2270                2275                2280

Glu Val Gly Ser Lys Val Gln Phe Phe Cys Asn Glu Gly Tyr Glu
    2285                2290                2295

Leu Val Gly Asp Ser Ser Trp Thr Cys Gln Lys Ser Gly Lys Trp
    2300                2305                2310

Asn Lys Lys Ser Asn Pro Lys Cys Met Pro Ala Lys Cys Pro Glu
    2315                2320                2325

Pro Pro Leu Leu Glu Asn Gln Leu Val Leu Lys Glu Leu Thr Thr
    2330                2335                2340

Glu Val Gly Val Val Thr Phe Ser Cys Lys Glu Gly His Val Leu
    2345                2350                2355

Gln Gly Pro Ser Val Leu Lys Cys Leu Pro Ser Gln Gln Trp Asn
    2360                2365                2370

Asp Ser Phe Pro Val Cys Lys Ile Val Leu Cys Thr Pro Pro Pro
    2375                2380                2385

Leu Ile Ser Phe Gly Val Pro Ile Pro Ser Ser Ala Leu His Phe
    2390                2395                2400

Gly Ser Thr Val Lys Tyr Ser Cys Val Gly Gly Phe Phe Leu Arg
    2405                2410                2415

Gly Asn Ser Thr Thr Leu Cys Gln Pro Asp Gly Thr Trp Ser Ser
    2420                2425                2430

Pro Leu Pro Glu Cys Val Pro Val Glu Cys Pro Gln Pro Glu Glu
    2435                2440                2445

Ile Pro Asn Gly Ile Ile Asp Val Gln Gly Leu Ala Tyr Leu Ser
```

-continued

```
              2450               2455               2460
Thr Ala Leu Tyr Thr Cys Lys Pro Gly Phe Glu Leu Val Gly Asn
        2465               2470               2475
Thr Thr Thr Leu Cys Gly Glu Asn Gly His Trp Leu Gly Gly Lys
        2480               2485               2490
Pro Thr Cys Lys Ala Ile Glu Cys Leu Lys Pro Lys Glu Ile Leu
        2495               2500               2505
Asn Gly Lys Phe Ser Tyr Thr Asp Leu His Tyr Gly Gln Thr Val
        2510               2515               2520
Thr Tyr Ser Cys Asn Arg Gly Phe Arg Leu Glu Gly Pro Ser Ala
        2525               2530               2535
Leu Thr Cys Leu Glu Thr Gly Asp Trp Asp Val Asp Ala Pro Ser
        2540               2545               2550
Cys Asn Ala Ile His Cys Asp Ser Pro Gln Pro Ile Glu Asn Gly
        2555               2560               2565
Phe Val Glu Gly Ala Asp Tyr Ser Tyr Gly Ala Ile Ile Ile Tyr
        2570               2575               2580
Ser Cys Phe Pro Gly Phe Gln Val Ala Gly His Ala Met Gln Thr
        2585               2590               2595
Cys Glu Glu Ser Gly Trp Ser Ser Ile Pro Thr Cys Met Pro
        2600               2605               2610
Ile Asp Cys Gly Leu Pro Pro His Ile Asp Phe Gly Asp Cys Thr
        2615               2620               2625
Lys Leu Lys Asp Asp Gln Gly Tyr Phe Glu Gln Glu Asp Asp Met
        2630               2635               2640
Met Glu Val Pro Tyr Val Thr Pro His Pro Pro Tyr His Leu Gly
        2645               2650               2655
Ala Val Ala Lys Thr Trp Glu Asn Thr Lys Glu Ser Pro Ala Thr
        2660               2665               2670
His Ser Ser Asn Phe Leu Tyr Gly Thr Met Val Ser Tyr Thr Cys
        2675               2680               2685
Asn Pro Gly Tyr Glu Leu Leu Gly Asn Pro Val Leu Ile Cys Gln
        2690               2695               2700
Glu Asp Gly Thr Trp Asn Gly Ser Ala Pro Ser Cys Ile Ser Ile
        2705               2710               2715
Glu Cys Asp Leu Pro Thr Ala Pro Glu Asn Gly Phe Leu Arg Phe
        2720               2725               2730
Thr Glu Thr Ser Met Gly Ser Ala Val Gln Tyr Ser Cys Lys Pro
        2735               2740               2745
Gly His Ile Leu Ala Gly Ser Asp Leu Arg Leu Cys Leu Glu Asn
        2750               2755               2760
Arg Lys Trp Ser Gly Ala Ser Pro Arg Cys Glu Ala Ile Ser Cys
        2765               2770               2775
Lys Lys Pro Asn Pro Val Met Asn Gly Ser Ile Lys Gly Ser Asn
        2780               2785               2790
Tyr Thr Tyr Leu Ser Thr Leu Tyr Tyr Glu Cys Asp Pro Gly Tyr
        2795               2800               2805
Val Leu Asn Gly Thr Glu Arg Arg Thr Cys Gln Asp Asp Lys Asn
        2810               2815               2820
Trp Asp Glu Asp Glu Pro Ile Cys Ile Pro Val Asp Cys Ser Ser
        2825               2830               2835
Pro Pro Val Ser Ala Asn Gly Gln Val Arg Gly Asp Glu Tyr Thr
        2840               2845               2850
```

-continued

Phe Gln Lys Glu Ile Glu Tyr Thr Cys Asn Glu Gly Phe Leu Leu
2855                2860                2865

Glu Gly Ala Arg Ser Arg Val Cys Leu Ala Asn Gly Ser Trp Ser
2870                2875                2880

Gly Ala Thr Pro Asp Cys Val Pro Val Arg Cys Ala Thr Pro Pro
2885                2890                2895

Gln Leu Ala Asn Gly Val Thr Glu Gly Leu Asp Tyr Gly Phe Met
2900                2905                2910

Lys Glu Val Thr Phe His Cys His Glu Gly Tyr Ile Leu His Gly
2915                2920                2925

Ala Pro Lys Leu Thr Cys Gln Ser Asp Gly Asn Trp Asp Ala Glu
2930                2935                2940

Ile Pro Leu Cys Lys Pro Val Asn Cys Gly Pro Pro Glu Asp Leu
2945                2950                2955

Ala His Gly Phe Pro Asn Gly Phe Ser Phe Ile His Gly Gly His
2960                2965                2970

Ile Gln Tyr Gln Cys Phe Pro Gly Tyr Lys Leu His Gly Asn Ser
2975                2980                2985

Ser Arg Arg Cys Leu Ser Asn Gly Ser Trp Ser Gly Ser Ser Pro
2990                2995                3000

Ser Cys Leu Pro Cys Arg Cys Ser Thr Pro Val Ile Glu Tyr Gly
3005                3010                3015

Thr Val Asn Gly Thr Asp Phe Asp Cys Gly Lys Ala Ala Arg Ile
3020                3025                3030

Gln Cys Phe Lys Gly Phe Lys Leu Leu Gly Leu Ser Glu Ile Thr
3035                3040                3045

Cys Glu Ala Asp Gly Gln Trp Ser Ser Gly Phe Pro His Cys Glu
3050                3055                3060

His Thr Ser Cys Gly Ser Leu Pro Met Ile Pro Asn Ala Phe Ile
3065                3070                3075

Ser Glu Thr Ser Ser Trp Lys Glu Asn Val Ile Thr Tyr Ser Cys
3080                3085                3090

Arg Ser Gly Tyr Val Ile Gln Gly Ser Ser Asp Leu Ile Cys Thr
3095                3100                3105

Glu Lys Gly Val Trp Ser Gln Pro Tyr Pro Val Cys Glu Pro Leu
3110                3115                3120

Ser Cys Gly Ser Pro Pro Ser Val Ala Asn Ala Val Ala Thr Gly
3125                3130                3135

Glu Ala His Thr Tyr Glu Ser Glu Val Lys Leu Arg Cys Leu Glu
3140                3145                3150

Gly Tyr Thr Met Asp Thr Asp Thr Asp Thr Phe Thr Cys Gln Lys
3155                3160                3165

Asp Gly Arg Trp Phe Pro Glu Arg Ile Ser Cys Ser Pro Lys Lys
3170                3175                3180

Cys Pro Leu Pro Glu Asn Ile Thr His Ile Leu Val His Gly Asp
3185                3190                3195

Asp Phe Ser Val Asn Arg Gln Val Ser Val Ser Cys Ala Glu Gly
3200                3205                3210

Tyr Thr Phe Glu Gly Val Asn Ile Ser Val Cys Gln Leu Asp Gly
3215                3220                3225

Thr Trp Glu Pro Pro Phe Ser Asp Glu Ser Cys Ser Pro Val Ser
3230                3235                3240

Cys Gly Lys Pro Glu Ser Pro Glu His Gly Phe Val Val Gly Ser
3245                3250                3255

| Lys | Tyr | Thr | Phe | Glu | Ser | Thr | Ile | Ile | Tyr | Gln | Cys | Glu | Pro | Gly |
|  | 3260 |  |  |  | 3265 |  |  |  | 3270 |  |  |  |  |  |

| Tyr | Glu | Leu | Glu | Gly | Asn | Arg | Glu | Arg | Val | Cys | Gln | Glu | Asn | Arg |
|  | 3275 |  |  |  | 3280 |  |  |  | 3285 |  |  |  |  |  |

| Gln | Trp | Ser | Gly | Gly | Val | Ala | Ile | Cys | Lys | Glu | Thr | Arg | Cys | Glu |
|  | 3290 |  |  |  | 3295 |  |  |  | 3300 |  |  |  |  |  |

| Thr | Gln | Leu | Glu | Phe | Leu | Asn | Gly | Lys | Ala | Asp | Ile | Glu | Asn | Arg |
|  | 3305 |  |  |  | 3310 |  |  |  | 3315 |  |  |  |  |  |

| Thr | Thr | Gly | Pro | Asn | Val | Val | Tyr | Ser | Cys | Asn | Arg | Gly | Tyr | Ser |
|  | 3320 |  |  |  | 3325 |  |  |  | 3330 |  |  |  |  |  |

| Leu | Glu | Gly | Pro | Ser | Glu | Ala | His | Cys | Thr | Glu | Asn | Gly | Thr | Trp |
|  | 3335 |  |  |  | 3340 |  |  |  | 3345 |  |  |  |  |  |

| Ser | His | Pro | Val | Pro | Leu | Cys | Lys | Pro | Asn | Pro | Cys | Pro | Val | Pro |
|  | 3350 |  |  |  | 3355 |  |  |  | 3360 |  |  |  |  |  |

| Phe | Val | Ile | Pro | Glu | Asn | Ala | Leu | Leu | Ser | Glu | Lys | Glu | Phe | Tyr |
|  | 3365 |  |  |  | 3370 |  |  |  | 3375 |  |  |  |  |  |

| Val | Asp | Gln | Asn | Val | Ser | Ile | Lys | Cys | Arg | Glu | Gly | Phe | Leu | Leu |
|  | 3380 |  |  |  | 3385 |  |  |  | 3390 |  |  |  |  |  |

| Gln | Gly | His | Gly | Ile | Ile | Thr | Tyr | Asn | Pro | Asp | Glu | Thr | Trp | Thr |
|  | 3395 |  |  |  | 3400 |  |  |  | 3405 |  |  |  |  |  |

| Gln | Thr | Ser | Ala | Lys | Cys | Glu | Lys | Ile | Ser | Cys | Gly | Pro | Pro | Ala |
|  | 3410 |  |  |  | 3415 |  |  |  | 3420 |  |  |  |  |  |

| His | Val | Glu | Asn | Ala | Ile | Ala | Arg | Gly | Val | His | Tyr | Gln | Tyr | Gly |
|  | 3425 |  |  |  | 3430 |  |  |  | 3435 |  |  |  |  |  |

| Asp | Met | Ile | Thr | Tyr | Ser | Cys | Tyr | Ser | Gly | Tyr | Met | Leu | Glu | Gly |
|  | 3440 |  |  |  | 3445 |  |  |  | 3450 |  |  |  |  |  |

| Phe | Leu | Arg | Ser | Val | Cys | Leu | Glu | Asn | Gly | Thr | Trp | Thr | Ser | Pro |
|  | 3455 |  |  |  | 3460 |  |  |  | 3465 |  |  |  |  |  |

| Pro | Ile | Cys | Arg | Ala | Val | Cys | Arg | Phe | Pro | Cys | Gln | Asn | Gly | Gly |
|  | 3470 |  |  |  | 3475 |  |  |  | 3480 |  |  |  |  |  |

| Ile | Cys | Gln | Arg | Pro | Asn | Ala | Cys | Ser | Cys | Pro | Glu | Gly | Trp | Met |
|  | 3485 |  |  |  | 3490 |  |  |  | 3495 |  |  |  |  |  |

| Gly | Arg | Leu | Cys | Glu | Glu | Pro | Ile | Cys | Ile | Leu | Pro | Cys | Leu | Asn |
|  | 3500 |  |  |  | 3505 |  |  |  | 3510 |  |  |  |  |  |

| Gly | Gly | Arg | Cys | Val | Ala | Pro | Tyr | Gln | Cys | Asp | Cys | Pro | Pro | Gly |
|  | 3515 |  |  |  | 3520 |  |  |  | 3525 |  |  |  |  |  |

| Trp | Thr | Gly | Ser | Arg | Cys | His | Thr | Ala | Val | Cys | Gln | Ser | Pro | Cys |
|  | 3530 |  |  |  | 3535 |  |  |  | 3540 |  |  |  |  |  |

| Leu | Asn | Gly | Gly | Lys | Cys | Val | Arg | Pro | Asn | Arg | Cys | His | Cys | Leu |
|  | 3545 |  |  |  | 3550 |  |  |  | 3555 |  |  |  |  |  |

| Ser | Ser | Trp | Thr | Gly | His | Asn | Cys | Ser | Arg | Lys | Arg | Arg | Thr | Gly |
|  | 3560 |  |  |  | 3565 |  |  |  | 3570 |  |  |  |  |  |

Phe

<210> SEQ ID NO 16
<211> LENGTH: 1396
<212> TYPE: DNA
<213> ORGANISM: Homo sapiens

<400> SEQUENCE: 16
agacggagtt aaatcattca ctattagaaa cagaggaaac tgagatcact gaattccatc    60
atgaaataga tactgatgct gagccaagga ttggaagtga ctcagttcag gtggtttaca   120
taaccgtagg cttacctaca cggtgttcct gactcccagc tggaatcttt taaccaaagg   180

| | |
|---|---|
| cccaccctc atgcaaagtg cacctttct ttacacgtgc gctctcccct ttggaggtct | 240 |
| tgctttggaa aaaccacccc aggtagcaac ttgtttcaaa gcagatatat gccaggtacc | 300 |
| acttaaagcc aggtggatct tatctgttga aatagatcaa gaacacatga aggggactg | 360 |
| gggaccccct acttacactt cagacttcag cacaaacttt ctgtcctcag agaaggcttc | 420 |
| tctggcctct ccaaggtcaa gtctgtctac ctaagctctc ctttatttag catggtcact | 480 |
| tgtaattaca tatattttgt atgttaatat ctggttaatg gtcacctcac ttgttaccct | 540 |
| ttaagttcat tgaggataga atccctgtca atttttgttc cttatatttg cagtgcctca | 600 |
| catagttcct ggcacacaat gggtattcaa aaaatatttg ttaaaatcag aaagaatga | 660 |
| acaaacagat gaatgaataa atgcacgact gaagtaccat gacaaatcat tcctgtggaa | 720 |
| cgcataaggt tagatgcaac tcctttatgg tgtgatctga gggggccctt aagggcttaa | 780 |
| tctgcacgct cacacacacc actgattaga aatccccatc aggaaaattg tacaatcatc | 840 |
| tatttggcga gggctttggg acactgaatg ggggaaaaga aacacaaaag gtgagcaagc | 900 |
| agttttcaaa ggatgctttc aactccctgg ccagtccgcg tgtatgtttt cgtctacaaa | 960 |
| gtgtttccaa ttactgtggc actctcggta tctggatcca tctccagtga attcctctgc | 1020 |
| agctcctgcc agacatatgg gatcaatcag ggcttcggcg ctggtgcgct tgctgcggga | 1080 |
| atgttgacag cctgacagac gcggggttct ggtgtcatgg aatctccgag cctttggctt | 1140 |
| gatcccggga ggagaatgag aggggagga gggagataga gtcacagata cagaaagtag | 1200 |
| acaggagcgg ggagagggag agagggagag aaggagggaa gcgggagatt tttcttgact | 1260 |
| gccccctttc cttcaaacat tttataggct tcagggagag agaggaggag gagagaggga | 1320 |
| agaaaaaaag aggagagcga gaggggtaga gagcgcgcgc cgttccctcc ggagttcccg | 1380 |
| agctgctgag gagtct | 1396 |

<210> SEQ ID NO 17
<211> LENGTH: 11139
<212> TYPE: DNA
<213> ORGANISM: Homo sapiens

<400> SEQUENCE: 17

| | |
|---|---|
| ggattgtgtc tgtccccagt gtcagatgaa agggcgctga ggctcttggc cgctgccccg | 60 |
| cgcccagctc cgcgcacgcc cctctgcgag tcccggccgcc cagcgcctct tcccgcccga | 120 |
| gccgccgcct gcgctccggg gcagccgctc tgtctccagc gcgatgtggc ctcgcctggc | 180 |
| cttttgttgc tggggtctgg cgctcgtttc gggctgggcg acctttcagc agatgtcccc | 240 |
| gtcgcgcaat ttcagcttcc gcctcttccc cgagaccgcg cccggggccc ccgggagtat | 300 |
| ccccgcgccg cccgctcctg gcgacgaagc ggcggggagc agagtggagc ggctgggcca | 360 |
| ggcgttccgg cgacgcgtgc ggctgctgcg ggagctcagc gagcgcctgg agcttgtctt | 420 |
| cctggtggat gattcgtcca gcgtgggcga agtcaacttc cgcagcgagc tcatgttcgt | 480 |
| ccgcaagctg ctgtccgact tccccgtggt gcccacggcc acgcgcgtgg ccatcgtgac | 540 |
| cttctcgtcc aagaactacg tggtgccgcg cgtcgattac atctccaccc gccgcgcgcg | 600 |
| ccagcacaag tgcgcgctgc tcctccaaga gatccctgcc atctcctacc gaggtggcgg | 660 |
| cacctacacc aagggcgcct tccagcaagc gcgcaaatt cttcttcatg ctagagaaaa | 720 |
| ctcaacaaaa gttgtatttc tcatcactga tggatattcc aatgggggag accctagacc | 780 |
| aattgcagcg tcactgcgag attcaggagt ggagatcttc actttggca tatggcaagg | 840 |
| gaacattcga gagctgaatg acatggcttc caccccaaag gaggagcact gttacctgct | 900 |

```
acacagtttt gaagaatttg aggctttagc tcgccgggca ttgcatgaag atctaccttc      960
tgggagtttt attcaagatg atatggtcca ctgctcatat ctttgtgatg aaggcaagga     1020
ctgctgtgac cgaatgggaa gctgcaaatg tgggacacac acaggccatt ttgagtgcat     1080
ctgtgaaaag gggtattacg ggaaaggtct gcagtatgaa tgcacagctt gcccatcggg     1140
gacatacaaa cctgaaggct caccaggagg aatcagcagt tgcattccat gtcctgatga     1200
aaatcacacc tctccacctg gaagcacatc ccctgaagac tgtgtctgca gagagggata     1260
cagggcatct ggccagacct gtgaacttgt ccactgccct gccctgaagc tcccgaaaaa     1320
tggttacttt atccaaaaca cttgcaacaa ccacttcaat gcagcctgtg ggtccgatg     1380
tcaccctgga tttgatcttg tgggaagcag catcatctta tgtctaccca atggtttgtg     1440
gtccggttta gagagctact gcagagtaag aacatgtcct catctccgcc agccgaaaca     1500
tggccacatc agctgttcta caagggaaat gttatataag caacatgtt tggttgcctg     1560
tgatgaaggg tacagactag aaggcagtga taagcttact tgtcaaggaa acagccagtg     1620
ggatgggcca gaaccccggt gtgtggagcg ccactgttcc acctttcaga tgcccaaaga     1680
tgtcatcata tcccccacca actgtggcaa gcagccagcc aaatttggga cgatctgcta     1740
tgtaagttgc cgccaagggt tcattttatc tggagtcaaa gaaatgctga gatgtaccac     1800
ttctggaaaa tggaatgtcg gagttcaggc agctgtgtgt aaagacgtgg aggctcctca     1860
aatcaactgt cctaaggaca tagaggctaa gactctggaa cagcaagatt ctgccaatgt     1920
tacctggcag attccaacag ctaaagacaa ctctggtgaa aaggtgtcag tccacgttca     1980
tccagctttc accccacctt accttttccc aattggagat gttgctatcg tatacacggc     2040
aactgaccta tccggcaacc aggccagctg cattttccat atcaaggtta ttgatgcaga     2100
accacctgtc atagactggt gcagatctcc acctcccgtc caggtctcgg agaaggtaca     2160
tgccgcaagc tgggatgagc ctcagttctc agacaactca ggggctgaat tggtcattac     2220
cagaagtcat acacaaggag accttttccc tcaaggggag actatagtac agtatacggc     2280
cactgacccc tcaggcaata acaggacatg tgatatccat attgtcataa aaggttctcc     2340
ctgtgaaatt ccattcacac ctgtaaatgg ggatttttata tgcactccag ataatactgg     2400
agtcaactgt acattaactt gcttggaggg ctatgatttc acagaagggt ctactgacaa     2460
gtattattgt gcttatgaag atggcgtctg gaaaccaaca tataccactg aatggccaga     2520
ctgtgccaaa aaacgttttg caaaccacgg gttcaagtcc tttgagatgt tctacaaagc     2580
agctcgttgt gatgacacag atctgatgaa gaagttttct gaagcatttg agacgaccct     2640
gggaaaaatg gtcccatcat tttgtagtga tgcagaggac attgactgga gactggagga     2700
gaacctgacc aaaaaatatt gcctagaata taattatgac tatgaaaatg ctttgcaat      2760
tggaccaggt ggctggggtg cagctaatag gctggattac tcttacgatg acttcctgga     2820
cactgtgcaa gaaacagcca caagcatcgg caatgccaag tcctcacgga ttaaaagaag     2880
tgccccatta tctgactata aaattaagtt aattttttaac atcacagcta gtgtgccatt     2940
acccgatgaa agaaatgata cccttgaatg ggaaaatcag caacgactcc ttcagacatt     3000
ggaaactatc acaaataaac tgaaaaggac tctcaacaaa accccatgt attcctttca      3060
gcttgcatca gaaatactta tagccgacac caattcatta ggaacaaaaa aggcttcccc     3120
cttctgcaga ccaggctcag tgctgagagg gcgtatgtgt gtcaattgcc ctttgggaac     3180
ctattataat ctggaacatt tcacctgtga aagctgccgg atcggatcct atcaagatga     3240
agaagggcaa cttgagtgca agctttgccc ctctgggatg tacacggaat atatccattc     3300
```

```
aagaaacatc tctgattgta aagctcagtg taaacaaggc acctactcat gcagtggact   3360
tgagacttgt gaatcgtgtc cactgggcac ttatcagcca aaatttggtt cccggagctg   3420
cctctcgtgt ccagaaaaca cctcaactgt gaaagagga gccgtgaaca tttctgcatg   3480
tggagttcct tgtccagaag gaaaattctc gcgttctggg ttaatgccct gtcacccatg   3540
tcctcgtgac tattaccaac ctaatgcagg gaaggccttc tgcctggcct gtcccttta   3600
tggaactacc ccattcgctg gttccagatc catcacagaa tgttcaagtt ttagttcaac   3660
tttctcagcg gcagaggaaa gtgtggtgcc ccctgcctct cttggacata ttaaaaagag   3720
gcatgaaatc agcagtcagg ttttccatga atgcttcttt aacccttgcc acaatagtgg   3780
aacctgccag caacttgggc gtggttatgt ttgtctctgt ccacttggat atacaggctt   3840
aaagtgtgaa acagacatcg atgagtgcag cccactgcct tgcctcaaca atggagtttg   3900
taaagaccta gttggggaat tcatttgtga gtgcccatca ggttacacag gtcagcggtg   3960
tgaagaaaat ataaatgagt gtagctccag tccttgttta aataaaggaa tctgtgttga   4020
tggtgtggct ggctatcgtt gcacatgtgt gaaaggattt gtaggcctgc attgtgaaac   4080
agaagtcaat gaatgccagt caaacccatg cttaaataat gcagtctgtg aagaccaggt   4140
tgggggattc ttgtgcaaat gcccacctgg attttttgggt acccgatgtg gaaagaacgt   4200
cgatgagtgt ctcagtcagc catgcaaaaa tggagctacc tgtaaagacg gtgccaatag   4260
cttcagatgc ctgtgtgcag ctggcttcac aggatcacac tgtgaattga acatcaatga   4320
atgtcagtct aatccatgta gaaatcaggc cacctgtgtg gatgaattaa attcatacag   4380
ttgtaaatgt cagccaggat tttcaggcaa aaggtgtgaa acagaacagt ctacaggctt   4440
taacctggat tttgaagttt ctggcatcta tggatatgtc atgctagttg gcatgctccc   4500
atctctccat gctctaacct gtaccttctg gatgaaatcc tctgacgaca tgaactatgg   4560
aacaccaatc tcctatgcag ttgataacgg cagcgacaat accttgctcc tgactgatta   4620
taacggctgg gttctttatg tgaatggcag ggaaaagata acaaactgtc cctcggtgaa   4680
tgatggcaga tggcatcata ttgcaatcac ttggacaagt gccaatgcca tctgaaaagt   4740
ctatatcgat gggaaattat ctgacggtgg tgctggcctc tctgttggtt tgcccatacc   4800
tggtatgttt ggtggtggtg cgttagttct ggggcaagag caagacaaaa aaggagaggg   4860
attcagccca gctgagtctt ttgtgggctc cataagccag ctcaacctct gggactatgt   4920
cctgtctcca cagcaggtga agtcactggc tacctcctgc ccagaggaac tcagtaaagg   4980
aaacgtgtta gcatggcctg atttcttgtc aggaattgtg gggaaagtga agatcgattc   5040
taagagcata ttttgttctg attgcccacg cttaggaggg tcagtgcctc atctgagaac   5100
tgcatctgaa gatttaaagc caggttccaa agtcaatctg ttctgtgatc caggcttcca   5160
gctggtcggg aaccctgtgc agtactgtct gaatcaagga cagtggacac aaccacttcc   5220
tcactgtgaa cgcattagct gtggggtgcc acctcctttg gagaatggct tccattcagc   5280
cgatgacttc tatgctggca gcacagtaac ctaccagtgc aacaatggct actatctatt   5340
gggtgactca aggatgttct gtacagataa tgggagctgg aacggcgttt caccatcctg   5400
ccttgatgtc gatgagtgtg cagttggatc agattgtagt gagcatgctt cttgcctgaa   5460
cgtagatgga tcctacatat gttcatgtgt ccccctcgtac acaggagatg ggaaaaactg   5520
tgcagaacct ataaaatgta aggctccagg aaatccggaa aatggccact cctcaggtga   5580
gatttataca gtaggtgccg aagtcacatt ttcgtgtcag gaaggatacc agttgatggg   5640
agtaaccaaa atcacatgtt tggagtctgg agaatggaat catctaatac catattgtaa   5700
```

-continued

```
agctgtttca tgtggtaaac cggctattcc agaaaatggt tgcattgagg agttagcatt    5760
tacttttggc agcaaagtga catataggtg taataaagga tatactctgg ccggtgataa    5820
agaatcatcc tgtcttgcta acagttcttg gagtcattcc cctcctgtgt gtgaaccagt    5880
gaagtgttct agtccggaaa atataaataa tggaaaatat attttgagtg ggcttaccta    5940
cctttctact gcatcatatt catgcgatac aggatacagc ttacagggcc cttccattat    6000
tgaatgcacg gcttctggca tctgggacag agcgccacct gcctgtcacc tcgtcttctg    6060
tggagaacca cctgccatca aagatgctgt cattacgggg aataacttca cttttcaggaa   6120 caccgtcact tacacttgca agaaggcta tactcttgct ggtcttgaca ccattgaatg     6180
cctggccgac ggcaagtgga gtagaagtga ccagcagtgc ctggctgtct cctgtgatga    6240
gccacccatt gtggaccacg cctctccaga gactgcccat cggctctttg gagacattgc    6300
attctactac tgctctgatg gttacagcct agcagacaat tcccagcttc tctgcaatgc    6360
ccagggcaag tgggtacccc cagaaggtca agacatgccc cgttgtatag ctcatttctg    6420
tgaaaaacct ccatcggttt cctatagcat cttggaatct gtgagcaaag caaaatttgc    6480
agctggctca gttgtgagct ttaaatgcat ggaaggcttt gtactgaaca cctcagcaaa    6540
gattgaatgt atgagaggtg ggcagtggaa cccttccccc atgtccatcc agtgcatccc    6600
tgtgcggtgt ggagagccac caagcatcat gaatggctat gcaagtggat caaactacag    6660
ttttggagcc atggtggctt acagctgcaa caaggggttc tacatcaaag gggaaaagaa    6720
gagcacctgc gaagccacag gcagtggag tagtcctata ccgacgtgcc acccggtatc     6780
ttgtggtgaa ccacctaagg ttgagaatgg cttttctggag catacaactg gcaggatctt   6840
tgagagtgaa gtgaggtatc agtgtaaccc gggctataag tcagtcggaa gtcctgtatt    6900
tgtctgccaa gccaatcgcc actggcacag tgaatcccct ctgatgtgtg ttcctctcga    6960
ctgtggaaaa cctcccccga tccagaatgg cttcatgaaa ggagaaaact ttgaagtagg    7020
gtccaaggtt cagttttct gtaatgaggg ttatgagctt gttggtgaca gttcttggac      7080
atgtcagaaa tctggcaaat ggaataagaa gtcaaatcca aagtgcatgc ctgccaagtg    7140
cccagagccg cccctcttgg aaaaccagct agtattaaag gagttgacca ccgaggtagg    7200
agttgtgaca ttttcctgta agaagggca tgtcctgcaa ggcccctctg tcctgaaatg     7260
cttgccatcc cagcaatgga atgactcttt ccctgttgtgt aagattgttc tttgtacccc   7320
acctccccta atttcctttg gtgtccccat tccttcttct gctcttcatt ttggaagtac    7380
tgtcaagtat tcttgtgtag gtgggttttt cctaagagga aattctacca ccctctgcca    7440
acctgatggc acctggagct ctccactgcc agaatgtgtt ccagtagaat gtcccccaacc   7500 tgaggaaatc cccaatggaa tcattgatgt gcaaggcctt gcctatctca gcacagctct    7560
ctatacctgc aagccaggct ttgaattggt gggaaatact accacccttt gtggagaaaa    7620
tggtcactgg cttggaggaa aaccaacatg taaagccatt gagtgcctga acccaaggga    7680
gattttgaat ggcaaattct cttacacgga cctacactat ggacagaccg ttacctactc    7740
ttgcaaccga ggctttcggc tcgaaggtcc cagtgccttg acctgtttag agacaggtga    7800
ttgggatgta gatgccccat cttgcaatgc catccactgt gattccccac acccattga    7860 aaatggtttt gtagaaggtg cagattacag ctatggtgcc ataatcatct acagttgctt    7920
ccctgggttt caggtggctg gtcatgccat gcagacctgt gaagagtcag gatggtcaag    7980
ttccatccca acatgtatgc caatagactg tggcctccct cctcatatag attttggaga    8040
ctgtactaaa ctcaaagatg accagggata ttttgagcaa gaagacgaca tgatggaagt    8100
```

```
tccatatgtg actcctcacc ctccttatca tttgggagca gtggctaaaa cctgggaaaa   8160
tacaaaggag tctcctgcta cacattcatc aaactttctg tatggtacca tggtttcata   8220
cacctgtaat ccaggatatg aacttctggg gaaccctgtg ctgatctgcc aggaagatgg   8280
aacttggaat ggcagtgcac catcctgcat ttcaattgaa tgtgacttgc ctactgctcc   8340
tgaaaatggc ttttgcgtt ttacagagac tagcatggga agtgctgtgc agtatagctg   8400
taaacctgga cacattctag caggctctga cttaaggctt tgtctagaga atagaaagtg   8460
gagtggtgcc tccccacgct gtgaagccat tcatgcaaa aagccaaatc cagtcatgaa   8520
tggatccatc aaaggaagca actacacata cctgagcacg ttgtactatg agtgtgaccc   8580
cggatatgtg ctgaatggca ctgagaggag aacatgccag gatgacaaaa actgggatga   8640
ggatgagccc atttgcattc ctgtggactg cagttcaccc ccagtctcag ccaatggcca   8700
ggtgagagga gacgagtaca cattccaaaa agagattgaa tacacttgca atgaagggtt   8760
cttgcttgag ggagccagga gtcgggtttg tcttgccaat ggaagttgga gtggagccac   8820
tcccgactgt gtgcctgtca gatgtgccac cccgccacaa ctggccaatg ggtgacgga   8880 aggcctggac tatggcttca tgaaggaagt aacattccac tgtcacgagg ctacatcttg   8940
gcacggtgct ccaaaactca cctgtcagtc agatggcaac tgggatgcag agattcctct   9000
ctgtaaacca gtcaactgtg gacctcctga agatcttgcc catggtttcc ctaatggttt   9060
ttcctttatt catgggggcc atatacagta tcagtgcttt cctggttata agctccatgg   9120
aaattcatca agaaggtgcc tctccaatgg ctcctggagt ggcagctcac cttcctgcct   9180
gccttgcaga tgttccacac cagtaattga atatggaact gtcaatggga cagattttga   9240
ctgtggaaag gcagcccgga ttcagtgctt caaaggcttc aagctcctag gactttctga   9300
aatcacctgt gaagccgatg gccagtggag ctctgggttc ccccactgtg aacacacttc   9360
ttgtggttct cttccaatga taccaaatgc gttcatcagt gagaccagct cttggaagga   9420
aaatgtgata acttacagct gcaggtctgg atatgtcata caaggcagtt cagatctgat   9480
ttgtacagag aaaggggtat ggagccagcc ttatccagtc tgtgagccct tgtcctgtgg   9540
gtccccaccg tctgtcgcca atgcagtggc aactggagag gcacacacct atgaaagtga   9600
agtgaaactc agatgtctgg aaggttatac gatggataca gatacagata cattcacctg   9660
tcagaaagat ggtcgctggt tccctgagag aatctcctgc agtcctaaaa aatgtcctct   9720
cccggaaaac ataacacata tacttgttca tggggacgat ttcagtgtga ataggcaagt   9780
ttctgtgtca tgtgcagaag ggtataacctt tgagggagtt aacatatcag tatgtcagct   9840
tgatggaacc tgggagccac cattctccga tgaatcttgc agtccagttt cttgtgggaa   9900
acctgaaagt ccagaacatg gatttgtggt tggcagtaaa tacaccttgt aaagcacgat   9960
tatttatcag tgtgagcctg gctatgaact agaggggaac agggaacgtg tctgccagga  10020
gaacagacag tggagtggag gggtggcaat atgcaaagag accaggtgtg aaactcaact  10080
tgaatttctc aatgggaaag ctgacattga aaacaggacg actggaccca acgtggtata  10140
ttcctgcaac agaggctaca gtcttgaagg gccatctgag gcacactgca cagaaaatgg  10200
aacctggagc cacccagtcc ctctctgcaa accaaatcca tgccctgttc cttttgtgat  10260
tcccgagaat gctctgctgt ctgaaaagga gttttatgtt gatcagaatg tgtccatcaa  10320
atgtagggaa ggttttctgc tgcagggcca cggcatcatt acctacaacc ccgacgagac  10380
gtggacacag acaagcgcca aatgtgaaaa aatctcatgt ggtccaccgg ctcacgtaga  10440
aaatgcaatt gctcgaggcg tacattatca atatggagac atgatcacct actcatgtta  10500
```

```
cagtggatac atgttggagg gtttcctgag gagtgtttgt ttagaaaatg gaacatggac    10560
atcacctcct atttgcagag ctgtctgtcg atttccatgt cagaatgggg gcatctgcca    10620
acgcccaaat gcttgttcct gtccagaggg ctggatgggg cgcctctgtg aagaaccaat    10680
ctgcattctt ccctgtctga acggaggtcg ctgtgtggcc ccttaccagt gtgactgccc    10740
gcctggctgg acggggtctc gctgtcatac agctgtttgc cagtctccct gcttaaatgg    10800
tggaaaatgt gtaagaccaa accgatgtca ctgtctttct tcttggacgg gacataactg    10860
ttccaggaaa aggaggactg ggttttaacc actgcacgac catctggctc tcccaaaagc    10920
aggatcatct ctcctcggta gtgcctgggc atcctggaac ttatgcaaag aaagtccaac    10980
atggtgctgg gtcttgttta gtaaacttgt tacttggggt tacttttttt attttgtgat    11040
atattttgtt attccttgtg acatactttc ttacatgttt ccattttttaa atatgcctgt    11100 attttctata taaaaattat attaaataga tgctgctac                           11139
```

<210> SEQ ID NO 18
<211> LENGTH: 19
<212> TYPE: DNA
<213> ORGANISM: Artificial sequence
<220> FEATURE:
<223> OTHER INFORMATION: SiRNA oligonucleotide

<400> SEQUENCE: 18
tatatgcact ccagataat                                                 19

<210> SEQ ID NO 19
<211> LENGTH: 19
<212> TYPE: DNA
<213> ORGANISM: Artificial sequence
<220> FEATURE:
<223> OTHER INFORMATION: SiRNA oligonucleotide

<400> SEQUENCE: 19
atatgcactc cagataata                                                 19

<210> SEQ ID NO 20
<211> LENGTH: 19
<212> TYPE: DNA
<213> ORGANISM: Artificial sequence
<220> FEATURE:
<223> OTHER INFORMATION: SiRNA oligonucleotide

<400> SEQUENCE: 20
aaatggcttt gcaattgga                                                 19

<210> SEQ ID NO 21
<211> LENGTH: 19
<212> TYPE: DNA
<213> ORGANISM: Artificial sequence
<220> FEATURE:
<223> OTHER INFORMATION: SiRNA oligonucleotide

<400> SEQUENCE: 21
gccaagtcct cacggatta                                                 19

<210> SEQ ID NO 22
<211> LENGTH: 19
<212> TYPE: DNA
<213> ORGANISM: Artificial sequence
<220> FEATURE:
<223> OTHER INFORMATION: SiRNA oligonucleotide

<400> SEQUENCE: 22

```
cgacagcaat tcattagga                                              19
```

<210> SEQ ID NO 23
<211> LENGTH: 8
<212> TYPE: PRT
<213> ORGANISM: Artificial sequence
<220> FEATURE:
<223> OTHER INFORMATION: A synthetic peptide that may be used for
      generating antibodies against SEL-OB

<400> SEQUENCE: 23

Arg Asp Ser Gly Val Glu Ile Phe
1               5

<210> SEQ ID NO 24
<211> LENGTH: 9
<212> TYPE: PRT
<213> ORGANISM: Artificial sequence
<220> FEATURE:
<223> OTHER INFORMATION: A synthetic peptide that may be used for
      generating antibodies against SEL-OB

<400> SEQUENCE: 24

Arg Leu Asp Tyr Ser Tyr Asp Asp Phe
1               5

<210> SEQ ID NO 25
<211> LENGTH: 17
<212> TYPE: PRT
<213> ORGANISM: Artificial sequence
<220> FEATURE:
<223> OTHER INFORMATION: A synthetic peptide that may be used for
      generating antibodies against SEL-OB

<400> SEQUENCE: 25

Asp Gly Gly Ala Gly Leu Ser Val Gly Leu Pro Ile Pro Gly Met Phe
1               5                   10                  15
Gly

<210> SEQ ID NO 26
<211> LENGTH: 8
<212> TYPE: PRT
<213> ORGANISM: Artificial sequence
<220> FEATURE:
<223> OTHER INFORMATION: A synthetic peptide that may be used for
      generating antibodies against SEL-OB

<400> SEQUENCE: 26

Gln Asp Asp Lys Asn Trp Asp Glu
1               5

<210> SEQ ID NO 27
<211> LENGTH: 14
<212> TYPE: PRT
<213> ORGANISM: Artificial sequence
<220> FEATURE:
<223> OTHER INFORMATION: A synthetic peptide that may be used for
      generating antibodies against SEL-OB

<400> SEQUENCE: 27

Glu Asn Ala Ile Ala Arg Gly Val His Tyr Gln Tyr Gly Asp
1               5                   10

<210> SEQ ID NO 28
<211> LENGTH: 8
<212> TYPE: PRT
<213> ORGANISM: Artificial sequence
<220> FEATURE:

```
<223> OTHER INFORMATION: A possible Ab cross reacting motif in mouse
      polydom protein

<400> SEQUENCE: 28

Arg Asp Phe Gly Val Glu Ile Phe
1               5

<210> SEQ ID NO 29
<211> LENGTH: 9
<212> TYPE: PRT
<213> ORGANISM: Artificial sequence
<220> FEATURE:
<223> OTHER INFORMATION: A possible Ab cross reacting motif in mouse
      polydom protein

<400> SEQUENCE: 29

Arg Leu Asp Tyr Ser Tyr Asp His Phe
1               5

<210> SEQ ID NO 30
<211> LENGTH: 8
<212> TYPE: PRT
<213> ORGANISM: Artificial sequence
<220> FEATURE:
<223> OTHER INFORMATION: A possible Ab cross reacting motif in mouse
      polydom protein

<400> SEQUENCE: 30

Gln Glu Asn Arg Asp Trp Asp Gly
1               5

<210> SEQ ID NO 31
<211> LENGTH: 401
<212> TYPE: DNA
<213> ORGANISM: Mus musculus

<400> SEQUENCE: 31
taccaccctc tgtggggaaa atggccagtg gctcggagga aaaccaatgt gcaaacccat      60
tgaatgccca gagcccaagg agattttaaa tggccaattc tcttccgtga gctttcagta     120
tggacaaacc atcacatact tttgtgaccg gggcttccgg ctcgaaggtc ccaaatccct     180
gacctgttta gagacaggtg actgggatat ggatccccccc tcttgtgatg ccatccactg     240
cagtgaccca cagcccattg aaaatggttt cgtagaaggt gcggattaca gatacggtgc     300
catgatcatc tatagctgct ccctgggtt tcaggtgctt ggtcatgcca tgcagacctg     360
tgaagagtcg ggatggtcaa gctccagccc aacctgtgta c                         401

<210> SEQ ID NO 32
<211> LENGTH: 400
<212> TYPE: DNA
<213> ORGANISM: Rattus norvegicus

<400> SEQUENCE: 32
aggctttgaa ttggtgggaa atactaccac cctttgtgga gaaaatggtc actggcttgg      60
aggaaaacca acatgtaaag ccattgagtg cctgaaaccc aaggagattt tgaatggcaa     120
attctcttac acggacctac actatggaca gaccgttacc tactcttgca accgaggctt     180
tcggctcgaa ggtcccagtg ccttgacctg tttagagaca ggtgattggg atgtagatgc     240
cccatcttgc aatgccatcc actgtgattc cccacaaccc attgaaaatg gttttgtaga     300
aggtgcagat tacagctatg gtgccataat catctacagt tgcttccctg ggtttcaggt     360
ggctggtcat gccatgcaga cctgtgaaga gtcaggatgg                           400
```

<210> SEQ ID NO 33
<211> LENGTH: 400
<212> TYPE: DNA
<213> ORGANISM: Homo sapiens

<400> SEQUENCE: 33

```
accacccttt gtggagaaaa tggtcactgg cttggaggaa aaccaacatg taaagccatt      60
gagtgcctga aacccaagga gattttgaat ggcaaattct cttacacgga cctacactat     120
ggacagaccg ttacctactc ttgcaaccga ggctttcggc tcgaaggtcc cagtgccttg     180
acctgtttag agacaggtga ttgggatgta atgcccccat cttgcaatgc catccactgt     240
gattccccac aacccattga aaatggtttt gtagaaggtg cagattacag ctatggtgcc     300
ataatcatct acagttgctt ccctgggttt caggtggctg gtcatgccat gcagacctgt     360
gaagagtcag gatggtcaag ttccatccca acatgtatgc                           400
```

<210> SEQ ID NO 34
<211> LENGTH: 401
<212> TYPE: DNA
<213> ORGANISM: Artificial sequence
<220> FEATURE:
<223> OTHER INFORMATION: Consensus sequence for alignment of mouse
    and Rat polydom and Human Sel-OB
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (394)..(394)
<223> OTHER INFORMATION: n is a, c, g, or t

<400> SEQUENCE: 34

```
naccaccctc tgtggggaaa atggccagtg gcttggagga aaaccaatgt gcaaacccat      60
tgaatgccca gagcccaagg agattttaaa tggccaattc tcttccgtga gctttcagta     120
tggacaaacc atcacatact cttgtgaccg aggcttccgg ctcgaaggtc ccaaatccct     180
gacctgttta gagacaggtg actgggatat ggatgcccca tcttgcaatg ccatccactg     240
tagtgaccca cagcccattg aaaatggttt cgtagaaggt gcggattaca gatatggtgc     300
catgatcatc tatagctgct ccctgggtt tcaggtggtt ggtcatgcca tgcagacctg     360
tgaagagtcg ggatggtcaa gatccagccc aacntgtgta c                        401
```

<210> SEQ ID NO 35
<211> LENGTH: 1500
<212> TYPE: DNA
<213> ORGANISM: Homo sapiens

<400> SEQUENCE: 35

```
agacggagtt aaatcattca ctattagaaa cagaggaaac tgagatcact gaattccatc      60
atgaaataga tactgatgct gagccaagga ttggaagtga ctcagttcag gtggtttaca     120
taaccgtagg cttacctaca cggtgttcct gactcccagc tggaatcttt taaccaaagg     180
cccaccctc atgcaaagtg cacctttct ttacacgtgc gctctcccct ttggaggtct      240
tgctttggaa aaaccacccc aggtagcaac ttgtttcaaa gcagatatat gccaggtacc     300
acttaaagcc aggtggatct tatctgttga aatagatcaa gaacacatga aggggactg     360
gggaccccct acttacactt cagacttcag cacaaacttt ccgtcctcag agaaggcttc     420
tctggcctct ccaaggtcaa gtctgtctac ctaagctctc ctttatttag catggtcact     480
tgtaattaca tatattttgt atgttaatat ctggttaatg gtcacctcac ttgttaccct     540
```

```
ttaagttcat tgaggataga atccctgtca atttttgttc cttatatttg cagtgcctca    600
catagttcct ggcacacaat gggtattcaa aaaatatttg ttaaaatcag gaaagaatga    660
acaaacagat gaatgaataa atgcacgact gaagtaccat gacaaatcat tcctgtggaa    720
cgcataaggt tagatgcaac tcctttatgg tgtgatctga gggggccctt aagggcttaa    780
tctgcacgct cacacacacc actgattaga aatccccatc aggaaaattg tacaatcatc    840
tatttggcga gggctttggg acactgaatg ggggaaaaga aacacaaaag gtgagcaagc    900
agttttcaaa ggatgctttc aactccctgg ccagtccgcg tgtatgtttt cgtctacaaa    960
gtgtttccaa ttactgtggc actctcggta tctggatcca tctccagtga attcctctgc   1020
agctcctgcc agacatatgg gatcaatcag ggcttcggcg ctggtgcgct tgctgcggga   1080
atgttgacag cctgacagac gcggggttct ggtgtcatgg aatctccgag cctttggctt   1140
gatcccggga ggagaatgag aggggagga gggagataga gtcacagata cagaaagtag   1200
acaggagcgg ggagagggag agaggagag aaggagggaa gcgggagatt tttcttgact   1260
gccccctttc cttcaaacat tttataggct tcagggagag agaggaggag gagagaggga   1320
agaaaaaaag aggagagcga gaggggtaga gagcgcgcgc cgttccctcc ggagttcccg   1380
agctgctgag gagtctggat tgtgtctgtc cccagtgtca gatgaaaggg cgctgaggct   1440
cttggccgct gccccgcgcc cagctccgcg cacgcccctc tgcgagtccg gccgcccagc   1500
```

POLYPEPTIDES, POLYNUCLEOTIDES ENCODING SAME, ANTIBODIES THEREAGAINST AND METHODS OF USING SAME FOR DIAGNOSING AND TREATING CANCER AND SKELETAL DISORDERS

RELATED APPLICATIONS

This application is a U.S. Continuation-In-Part (CIP) Patent Application of PCT Application No. PCT/IL2005/000225, filed on Feb. 23, 2005, which claims the benefit of U.S. Provisional Patent Application No. 60/546,181, filed on Feb. 23, 2004. The contents of the above Applications are incorporated herein by reference.

FIELD AND BACKGROUND OF THE INVENTION

The present invention relates to novel polypeptide sequences, polynucleotides encoding same and antibodies generated thereagainst which can be used to diagnose and treat cancer and skeletal disorders, such as osteoporosis.

Organization and differentiation of the embryo into distinct tissues requires adhesive mechanisms that promote and maintain physical segregation and association. The differentiation of mesenchymal stem cells to skeletal tissues occurs in response to microenvironmental signals evoked by cell adhesion molecules and affinities that control responses to hormones and growth factors (Ferguson et al., 1998; Olsen et al., 2000; Tepass et al., 2002; Triffitt et al., 1998). The differentiation of bone marrow cells that are maintained in a specific microenvironment is controlled by cell-cell and cell-matrix interactions mediated by selectins and integrins, which switch on intracellular signaling pathways regulating cell function (Jaiswal et al., 2000; Patel et al., 2002; Shur et al., 2001).

In a mammal, bone shape is maintained by continuous remodeling or sculpturing of its surface through two major processes, including bone formation and bone resorption, which are regulated by various soluble factors, systemic hormones, cell adhesion molecules, and focal mechanical stress (Arai et al., 2003; Goltzman, 2002). Osteoblasts, the cells from which bone develops, play a central role in bone formation by synthesizing and mineralizing bone matrices. Osteoblasts and their progenitors (bone marrow stromal cells) also function in the control of bone resorption by acquiring a supportive activity for osteoclast differentiation (Arai et al., 2003). An osteoclast, or an osteophage, is a large, multinucleate cell found in growing bone that resorbs bony tissue, as in the formation of canals and cavities or in a fracture that is healing. Osteoclastogenesis is the process of formation and development of osteoclasts, whereas osteogenesis is the process of formation and development of bony tissue from osteoblasts.

The differentiation and function of bone marrow and skeletal cells underlying bone remodeling processes is primarily regulated by estrogen. The effects of this hormone are integrated into multiple regulatory pathways that coordinate cell growth and proliferation (Brigstock, 2003; Manolagas et al., 2002; Spelsberg et al., 1999). Estrogen deficiency in vivo, e.g., at the postmenopausal period or after ovariectomy, stimulates skeletal destruction by increased osteoclastogenesis and decreased osteogenesis. (Benayahu et al., 2000; Ishihara et al., 1999; Liu et al., 2000; Watts, 2000).

Estrogens act to weaken the adhesive property of osteoclasts by inhibiting the activity of β-integrin adhesion molecules and thereby changing the cells' mode of interaction with the bone microenvironment (Duong et al., 1998; Moggs et al., 2003; Saintier et al., 2004). However, the precise mechanism whereby estrogen stimulates osteoblasts and bone formation is still unknown. Estrogenic regulation of transcriptional and translational events is mediated through cell surface molecules that activate signal transduction pathways in osteoblasts (Monroe et al., 2003, Plotkin et al., 2002, Rickard et al., 1999). The signals are translated to anti-apoptotic events (Manolagas et al., 2002) and modulate intracellular calcium levels, IP3, and cAMP through gap junctions (Massas et al., 1998; Lieberherr et al., 1993). These estrogenic effects on stromal and osteoblastic cells are mediated through specific cell surface proteins that interact with the microenvironment.

Some approaches for the treatment of bone disorders such as osteoporosis include, for example, estrogens, bisphosphonates, calcitonin, flavonoids, and selective estrogen receptor modulators. Other approaches include peptides from the parathyroid hormone family, strontium ranelate, and growth hormone and insulin-like growth response [see, for example, Reginster et al. "Promising New Agents in Osteoporosis" Drugs R & D 1999, 3, 195-201]. Unfortunately, these therapeutic agents still have significant shortcomings.

The variety of different approaches represented by the therapeutic agents currently available or under study evidence the variety of biological factors influencing the competing processes of bone production and resorption.

Although progress has been made towards developing therapeutic agents for osteoporosis and other bone disorders, there remains a need to develop new therapeutic agents which have an improved therapeutic efficacy, which may be given to patients who cannot well tolerate or do not respond to existing therapies, and/or which may be used in conjunction with other therapies.

SUMMARY OF THE INVENTION

According to one aspect of the present invention there is provided an isolated polypeptide comprising an amino acid sequence being at least 88% homologous to SEQ ID NO: 15 as determined by BlastP using default parameters, the isolated polypeptide being capable of promoting cell adhesion and/or cell homing.

According to further features in preferred embodiments of the invention described below, the amino acid sequence is as set forth in SEQ ID NO: 15.

According to still further features in the described preferred embodiments an isolated polynucleotide encoding the polypeptide comprising an amino acid sequence being at least 88% homologous to SEQ ID NO: 15 as determined by BlastP using default parameters, the isolated polypeptide being capable of promoting cell adhesion and/or cell homing.

According to still further features in the described preferred embodiments the polynucleotide comprises a nucleic acid sequence as set forth in SEQ ID NO: 14 or SEQ ID NO: 17.

According to still further features in the described preferred embodiments a nucleic acid construct comprising the polynucleotide encoding the polypeptide comprising an amino acid sequence being at least 88% homologous to SEQ ID NO: 15 as determined by BlastP using default parameters, the isolated polypeptide being capable of promoting cell adhesion and/or cell homing.

According to still further features in the described preferred embodiments the nucleic acid construct further comprising a regulatory sequence for mediating transcription of the isolated polynucleotide in a host cell.

According to still further features in the described preferred embodiments the regulatory sequence comprises a promoter sequence.

According to still further features in the described preferred embodiments the promoter sequence comprises an estrogen inducible element.

According to still further features in the described preferred embodiments the promoter sequence comprises a nucleic acid sequence being at least 97% identical to SEQ ID NO: 16, as determined using BlastN analysis using default parameters.

According to another aspect of the present invention there is provided an isolated polynucleotide comprising a nucleic acid sequence being at least 97% identical to SEQ ID NO: 16, as determined using BlastN analysis using default parameters, the isolated polynucleotide being capable of directing transcription of a coding sequence operatively linked thereto.

According to still further features in the described preferred embodiments the transcription is inducible by estrogen.

According to another aspect of the present invention there is provided a nucleic acid construct comprising the isolated polynucleotide comprising a nucleic acid sequence being at least 97% identical to SEQ ID NO: 16, as determined using BlastN analysis using default parameters, the isolated polynucleotide being capable of directing transcription of a coding sequence operatively linked thereto.

According to still further features in the described preferred embodiments the nucleic acid construct further comprising a nucleic acid sequence of interest, the nucleic acid sequence of interest being operatively linked to the isolated polynucleotide comprising a nucleic acid sequence being at least 97% identical to SEQ ID NO: 16, as determined using BlastN analysis using default parameters, the isolated polynucleotide being capable of directing transcription of a coding sequence operatively linked thereto.

According to another aspect of the present invention there is provided a mammalian cell transformed with the isolated polynucleotide encoding the polypeptide comprising an amino acid sequence being at least 88% homologous to SEQ ID NO: 15 as determined by BlastP using default parameters, the isolated polynucleotide being capable of promoting cell adhesion and/or cell homing.

According to another aspect of the present invention there is provided a mammalian cell transformed with the isolated polynucleotide comprising a nucleic acid sequence being at least 97% identical to SEQ ID NO: 16, as determined using BlastN analysis using default parameters, the isolated polynucleotide being capable of directing transcription of a coding sequence operatively linked thereto.

According to still further features in the described preferred embodiments the isolated polypeptide further comprising, conjugated to the amino acid sequence, at least one additional amino acid sequence encoding a therapeutic agent.

According to still further features in the described preferred embodiments A pharmaceutical composition comprising the isolated polypeptide and a pharmaceutically acceptable carrier.

According to still further features in the described preferred embodiments the isolated polypeptide comprises an amino acid sequence as set forth in SEQ ID NO: 15.

According to still further features in the described preferred embodiments a pharmaceutical composition comprising the isolated polynucleotide and a pharmaceutically acceptable carrier.

According to still further features in the described preferred embodiments the pharmaceutical composition comprising the polynucleotide and a pharmaceutically acceptable carrier.

According to yet another aspect of the present invention there is provided an antibody being capable of specifically binding a polypeptide comprising an amino acid sequence being at least 88% homologous to SEQ ID NO: 15 as determined by BlastP using default parameters, the polypeptide being capable of promoting cell adhesion and/or cell homing.

According to still further features in the described preferred embodiments the antibody is conjugated to a detectable moiety.

According to still further features in the described preferred embodiments the antibody is conjugated to a solid support.

According to still further features in the described preferred embodiments the antibody is conjugated to a therapeutic agent.

According still another aspect of the present invention there is provided a pharmaceutical composition comprising the antibody and a pharmaceutically acceptable carrier.

According to still further features in the described preferred embodiments the antibody is conjugated to a therapeutic agent or a detectable moiety.

According still another aspect of the present invention there is provided a method of diagnosing a presence of, or a predisposition to a disease associated with bone resorption in a subject, the method comprising detecting in a tissue and/or a cell of the subject an absence, a presence and/or a level of a polypeptide as set forth in SEQ ID NO: 15 or a polynucleotide encoding the polypeptide, wherein the absence, presence and/or the level of the polypeptide or the polynucleotide in the tissue or cell of the subject is indicative of a presence of, or a predisposition to the skeletal disorder in the subject.

According to an additional aspect of the present invention there is provided a method of treating a disease associated with bone resorption in a subject in need thereof, the method comprising administering to the subject a therapeutically effective amount of:

(i) a polypeptide having an amino acid sequence being at least 88% homologous to SEQ ID NO: 15 as determined by BlastP using default parameters; and/or (ii) a polynucleotide encoding for the polypeptide;

the polypeptide being capable of promoting cell adhesion and/or cell homing, thereby treating the disease associated with bone resorption in the subject.

According to still further features in the described preferred embodiments the disease associated with the bone resorption is selected from the group consisting of osteoporosis, osteopenia, hypercalcemia, jaw bone disorders, erosions associated with rheumatoid arthritis and Paget's disease and bone disorders associated with glucocorticoid, steroid, sex hormones and corticosteroid therapy.

According to yet an additional aspect of the present invention there is provided a method of treating cancer and/or an inflammatory disease in a subject in need thereof, the method comprising administering to the subject a therapeutically effective amount of an agent for down-regulating in cells of the subject a level and/or an activity of a polypeptide having an amino acid sequence being at least 88% homologous to SEQ ID NO: 15 as determined by BlastP using default parameters, thereby treating the cancer and/or the inflammatory disease in the subject.

According to still further features in the described preferred embodiments the agent is an estrogen inhibitor.

According to still further features in the described preferred embodiments the agent is an antibody capable of binding the polypeptide.

According to still further features in the described preferred embodiments the antibody is conjugated to a therapeutic moiety.

According to still further features in the described preferred embodiments the antibody is capable of neutrelizing a cell adhision and/or homing of the polypeptide.

According to still further features in the described preferred embodiments the therapeutic moiety is selected from the group consisting of a toxin, a proapoptotic factor, a chemotherapy and a radio-isotope.

According to still further features in the described preferred embodiments the cancer is selected from the group consisting of breast cancer, prostate cancer, lung cancer, thyroid cancer, renal cancer, myeloma, blastoma, lymphoma and melanoma.

According to still an additional aspect of the present invention there is provided a method of modulating an interaction of a first cell with a second cell and/or a microenvironment, the method comprising regulating a level and/or an activity of a polypeptide comprising an amino acid sequence being at least 88% homologous to SEQ ID NO: 15 as determined by BlastP using default parameters in the first cell, the second cell, and/or the microenvironment, thereby modulating the interaction of the first cell with the second cell and/or the microenvironment.

According to a further aspect of the present invention there is provided a method of identifying a stem cell, the method comprising detecting a cell expressing a polypeptide as set forth in SEQ ID NO: 15, wherein a presence of said polypeptide is indicative of a stem cell.

According to still further features in the described preferred embodiments the stem cell is a satellite cell, a mesenchimal stem cell or a hematopoietic stem cell.

According to a further aspect of the present invention there is provided a method of identifying a bone or periosteum cell, the method comprising detecting cells expressing a polypeptide as set forth in SEQ ID NO: 15, wherein a presence of said polypeptide is indicative of a bone or periosteum cell.

The present invention successfully addresses the shortcomings of the presently known configurations by providing novel polypeptide sequences, polynucleotides encoding same and antibodies thereagainst which can be used to diagnose and treat cancer and skeletal disorders, such as osteoporosis Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show details of the invention in more detail than is necessary for a fundamental understanding of the invention, the description taken with the drawings making apparent to those skilled in the art how the several forms of the invention may be embodied in practice.

In the drawings:

Figure 1B:
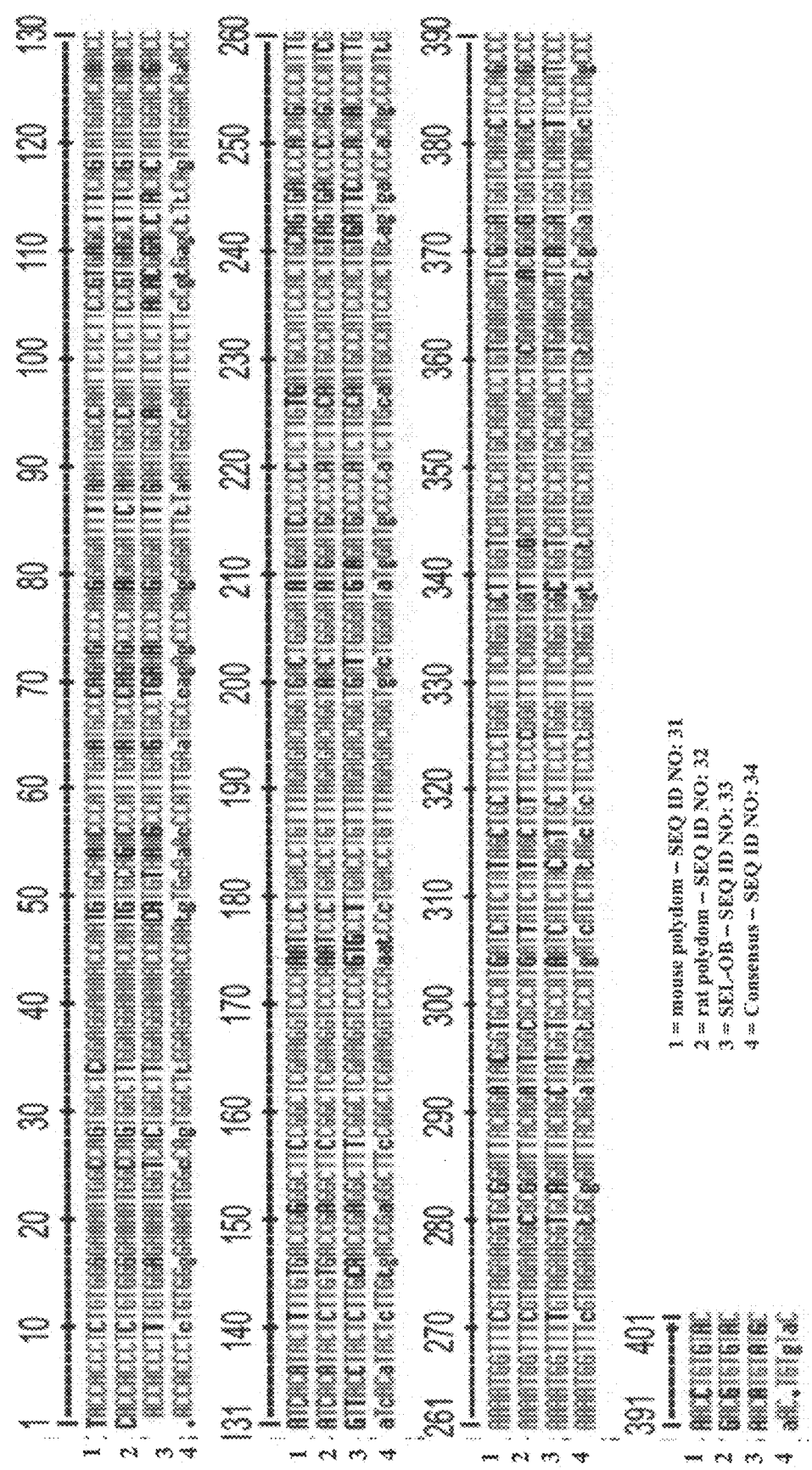
Figure 1C:
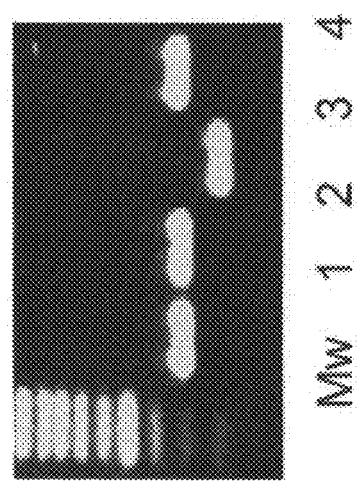

FIGS. 1a-c depicts the expression of SEL-OB cDNA reverse-transcribed from mRNA of various cell types and species, and a multiple alignment of cDNAs amplified using three species-specific sets of primers. FIG. 1a shows expression of full-length SEL-OB cDNA, indicated by an arrow. The cDNA is 11,139-bp long (not including promoter region). FIG. 1b is a multiple alignment by Multalin analysis of partial (400-401-bp) cDNA sequences of mouse polydom (GenBank Accession No. NP_073725), rat polydom (GenBank Accession No. XP_232929), and human SEL-OB (SEQ ID NO: 17). This region was used to create species-specific RT-PCR primers for differential expression analysis. The primer sequences and expected PCR product sizes are presented in Table 1. FIG. 1c depicts RT-PCR expression of SEL-OB mRNA from primary cultured cells: human trabecular bone (HTB) (unrelated to carcinoma cell lines), lane 1; human marrow stromal cells (MSCs), lane 2; mouse MSCs, lane 3; and rat MSCs, lane 4.

Figure 2A:
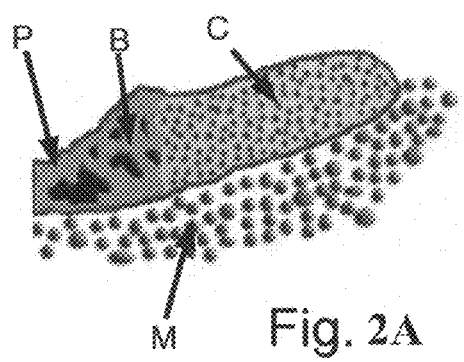
Figure 2B:
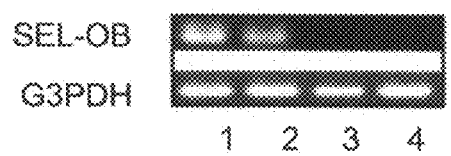

FIGS. 2a-b depicts SEL-OB differential expression in mouse newborn skeletal tissues retrieved by laser capture microdissection (LCM) technique. FIG. 2a shows a schematic illustration of the skeletal tissues: 1-periosteum; 2-bone; 3-cartilage; 4-skeletal muscle. FIG. 2b shows the reverse transcriptase polymerase chain reaction (RT-PCR) amplification products of SEL-OB cDNA reverse-transcribed from the mRNA of the four skeletal tissues, normalized to G3PDH: periosteum, lane 1; bone, lane 2; cartilage, lane 3; and muscle, lane 4. Periosteum and bone express SEL-OB, but cartilage and skeletal muscle do not.

Figure 3A:
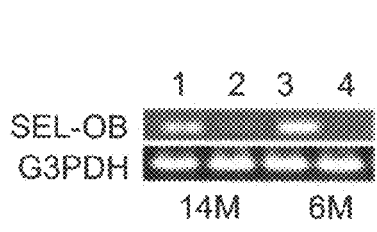
Figure 3B:
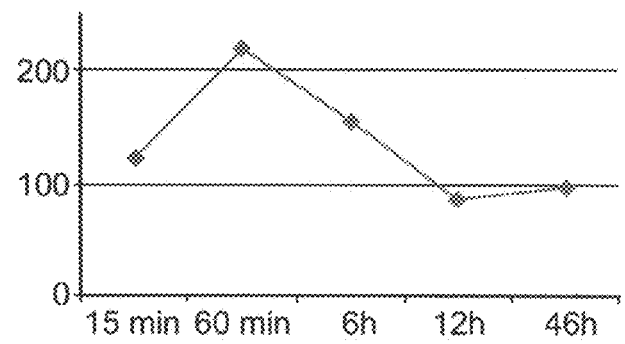

FIGS. 3a-b depicts SEL-OB expression in the bone marrow of ovariectomized and control-operated rats and in cultured osteoblasts. FIG. 3a shows SEL-OB expression analyzed by RT-PCR in bone marrow cells obtained from control-operated (sham) (lanes 1 and 3) and ovariectomized (OVX) (lanes 2 and 4) rats, 14 (lanes 1 and 2) and 6 (lanes 3 and 4) months-old. OVX rats are deficient in estrogen production. SEL-OB expression was detected in sham, but not OVX rats of both ages, supporting the conclusion that SEL-OB is estrogen-regulated. FIG. 3b shows real-time PCR results of SEL-OB expression in cultured osteoblasts modulated by 17 beta-estradiol, the most common estrogenic hormone. The levels of SEL-OB expression in cells treated from 15 minutes to 48 hours were compared with control (untreated) cells and normalized by G3PDH. The x-axis represents time points at which mRNA levels were analyzed by real-time PCR (not to scale), and the y-axis represents mRNA expression levels of 17 beta-estradiol-treated cells as a percent of mRNA expression levels of control cells, normalized to G3PDH levels.

Figure 4:
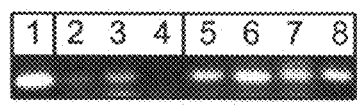

FIG. 4 demonstrates interaction of estrogen receptor (ER) and transcription factor pcJun with the promoter region of SEL-OB, which was predicted using bioinformatics analysis. The cross-linked immunoprecipitation (X-ChIP) technique was used to isolate and PCR-amplify DNA immunoprecipitated with antibodies to ER (anti-ER) (lane 1) and pcJun (anti-pcJun) (lanes 2-4): control (2); 17 beta-estradiol-treated (3); and ICI 182,780-treated (4). Lanes 5-8 represent input (control). MSCs demonstrated interaction of ER and pcJun with the SEL-OB promoter region. Control and 17 beta-estradiol-treated DNA immunoprecipitated with pcJun showed promoter-protein interaction, which was lost upon treatment with estrogen inhibitor ICI 182,780.

FIG. 5 is a schematic presentation of the SEL-OB protein domains, as predicted by SMART analysis.

FIG. 6 shows a high-molecular-weight band (~370 kDa), indicated by an arrow, corresponding to SEL-OB immuno-precipitated from hMSC lysates using anti-SEL-OB. Proteins were separated by SDS-PAGE and analyzed on a Western blot.

FIGS. 7a-e depict immunohistochemistry staining with anti-SEL-OB. Stained hMSCs are visualized by confocal microscopy (FIGS. 7a-c) or light microscopy (FIGS. 7d-e). Cultured cells present a heterogeneous morphology (630× magnification) (a); also shown are the same cells stained with anti-SEL-OB (630×) (b). An overlay of cultured unstained and stained cells reveals intensively stained cells (double-headed arrow) and an unstained cell (single arrow) (630×) (c). A visualization of SEL-OB staining at a lower magnification (400×) reveals that cells are heterogeneous in shape and pattern of expression (d). A cell expressing a high level of SEL-OB is circled in FIG. 7d, and shown at a higher magnification (630×) in FIG. 7e.

Figure 8A:
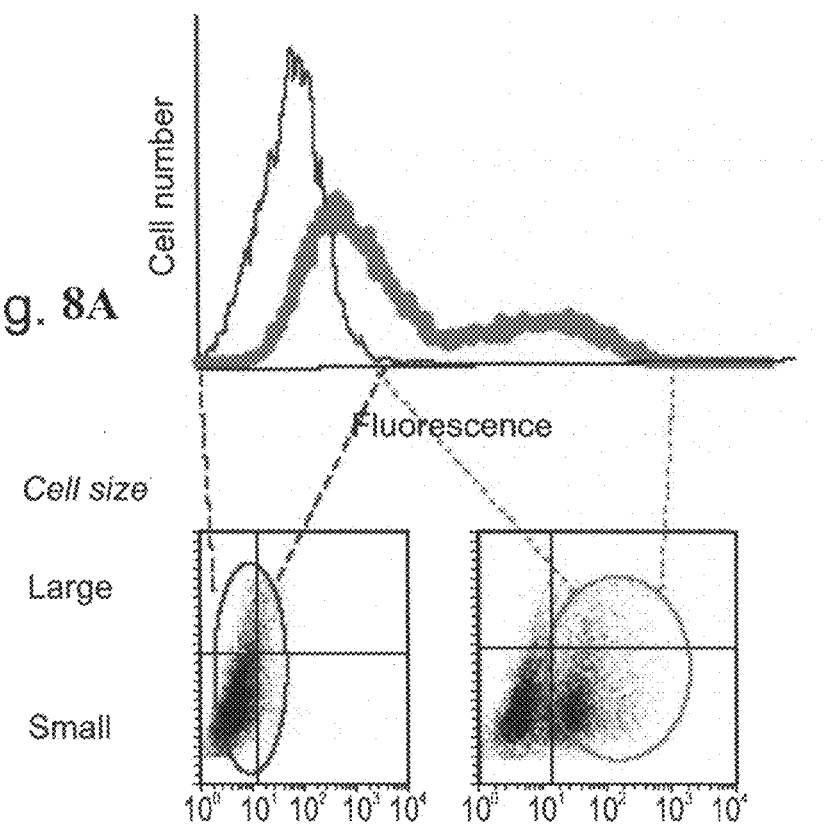
Figure 8A:
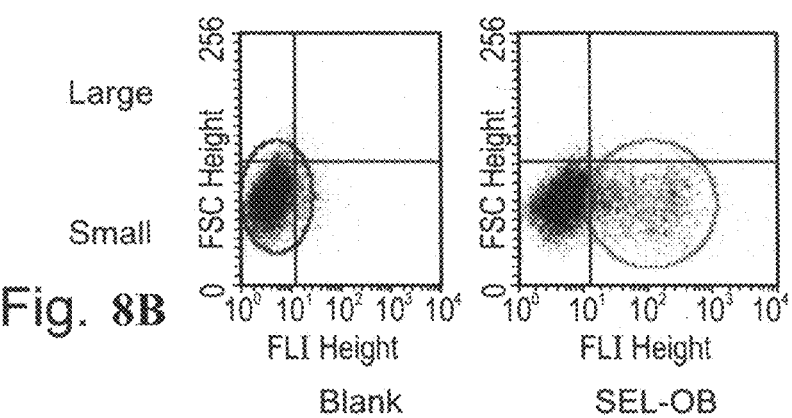
Figure 8C:
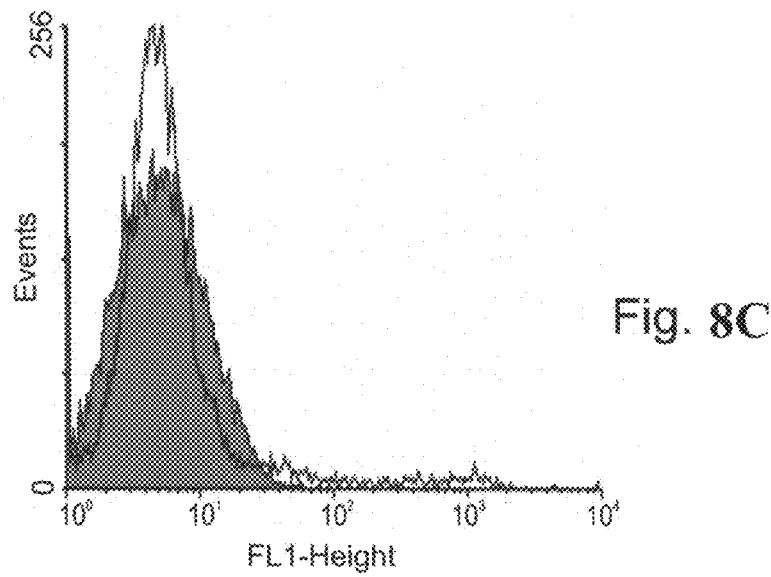

FIGS. 8a-c depicts FACS analysis of SEL-OB expression by intensity of cell staining versus cell numbers (FIGS. 8a, c) and versus cell size (FIG. 8b). The SEL-OB-positive population is sub-divided into two subpopulations presented as peaks of low- and high-fluorescence intensity (FIG. 8a). Dot plots represent SEL-OB staining of human MSCs (top panels) and mouse MBA-15 cells (bottom panels) (FIG. 8b). The x-axis represents the intensity of staining (FL1-Height) and the y-axis represents the cell size (FSC-Height) for blank and SEL-OB-stained samples (left and right panels, respectively). The blue curve depicts the blank. FIG. 8c depicts FACS analysis of SEL-OB expression in C2C12, a myoblast cell line of mouse origin. In each FACS analysis curve, the SEL-OB-positive population is divided into a low-fluorescence intensity subpopulation, indicated by the high peak, and a higher-intensity subpopulation, indicated by the low peak.

Figures 9A, 9B:
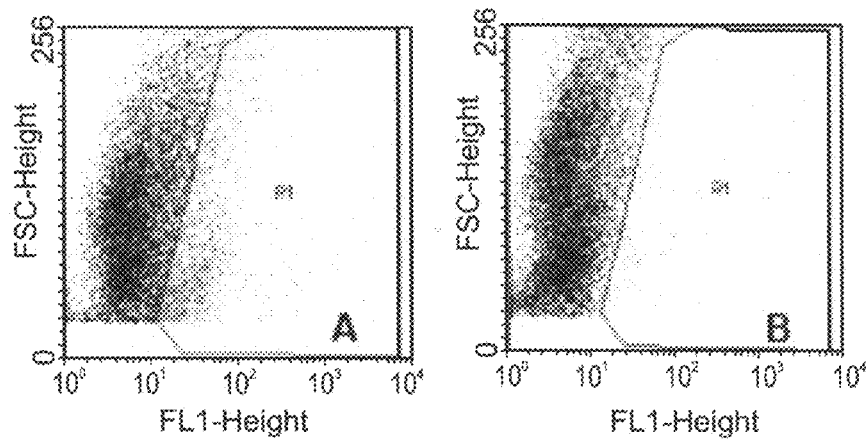

FIGS. 9a-b depicts a role for SEL-OB in adhesion processes. FACS analysis shows SEL-OB expression in MBA-15 cells incubated with anti-SEL-OB and re-plated for 15 minutes to follow their attachment (as compared with nonspecific IgG-incubated cells, results not shown). There were 50% more unbound cells in the anti-SEL-OB-treated fraction than in the control (IgG) fraction (results not shown), showing that SEL-OB antibody delays the initial cell attachment compared with the control. Region R1 represents positive (SEL-OB-expressing) staining in both unbound and bound cells. The figures show that there were 3.4-fold more SEL-OB-positive cells in the unbound fraction (FIG. 9a) versus the bound population (FIG. 9b). The x-axis represents the intensity of staining (FL1-Height) and the y-axis represents the cell size (FSC-Height). The interference of anti-SEL-OB with cell adhesion indicates that SEL-OB protein plays a role in this process.

Figure 10A:
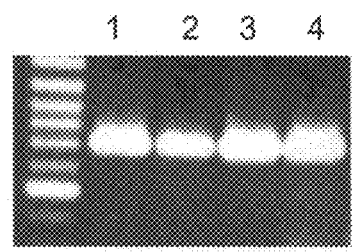
Figures 10B, 10C, 10D:
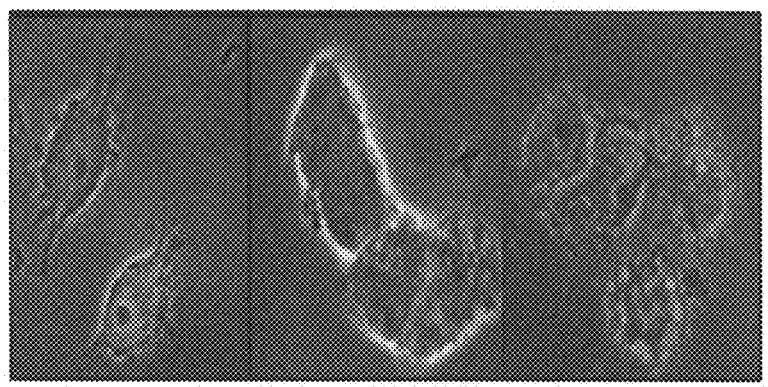

FIGS. 10a-d depicts SEL-OB expression in various cancer cell lines in vitro and in vivo. FIG. 10a shows RT-PCR expression of SEL-OB mRNA from primary cultured cells: MCF7, lane 1; MDA-231, lane 2; MDA-435, lane 3; and T-47D, lane 4. FIGS. 10b-d depict immunohistochemical staining with anti-SEL-OB, visualized by confocal microscopy (630×). The breast cancer cell lines expressing the SEL-OB protein are: MDA-231 (FIG. 10b); MCF7 (FIG. 10c); and T-47D (FIG. 10d).

Figure 11A:
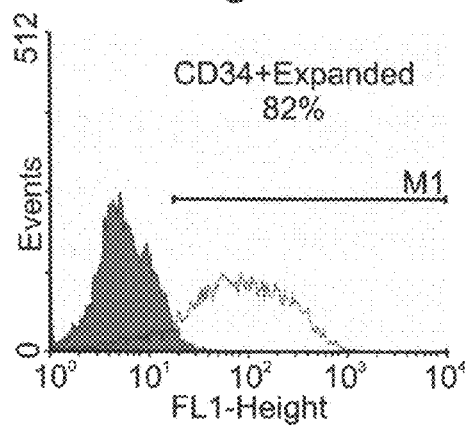
Figure 11B:
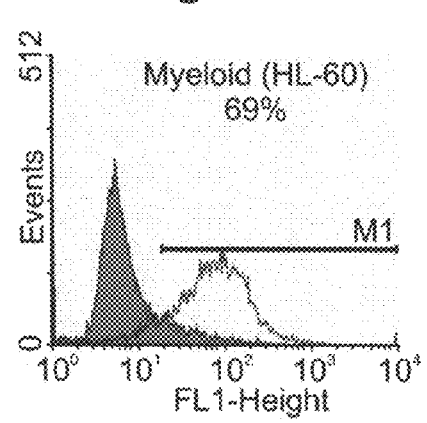
Figure 11C:
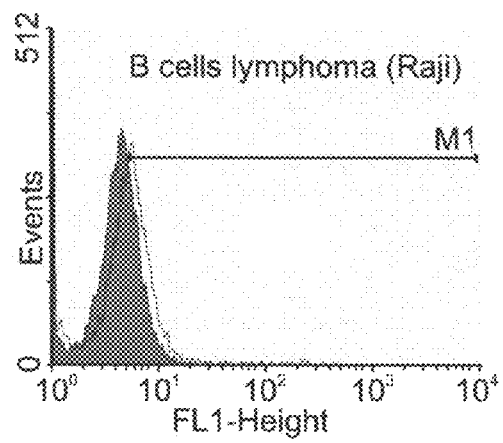
Figure 11D:
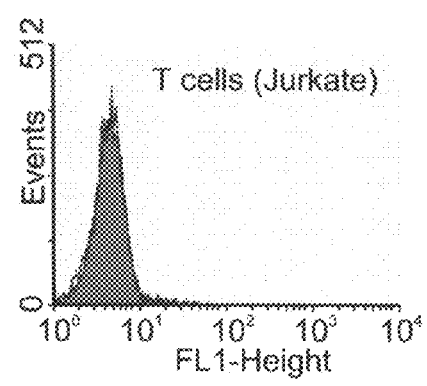

FIGS. 11a-d depict FACS analysis of SEL-OB expression in various human hematopoietic cell lines by intensity of cell staining versus cell numbers. The cell lines are: expanded human CD34+ hematopoietic stem/progenitor (FIG. 11a); HL-60 myeloid leukemia (FIG. 11b); Raji B cell lymphoma (FIG. 11c); and Jurkat T cell leukemia (FIG. 11d). Each cell line shows a SEL-OB-positive population divided into high- and low-fluorescence intensity subpopulations. The red curves are blanks. 82% and 69% of the total cell population of primary CD34+ cells and HL-60 cells, respectively, are SEL-OB-positive cells.

Figure 12A:
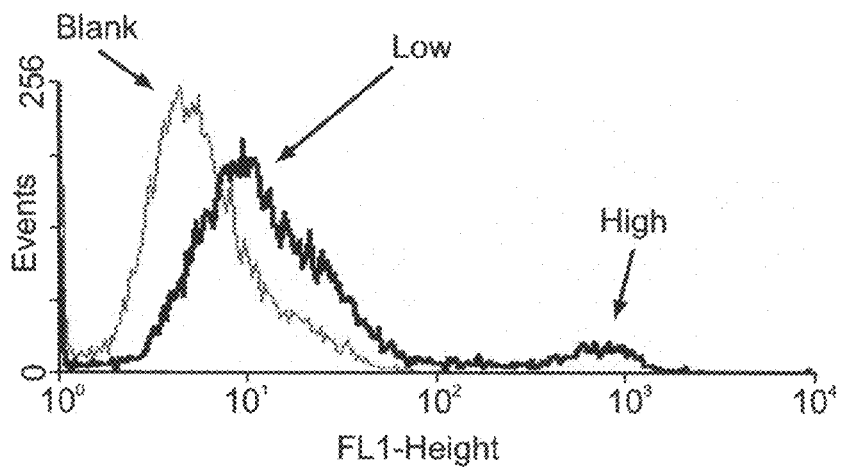
Figure 12B:
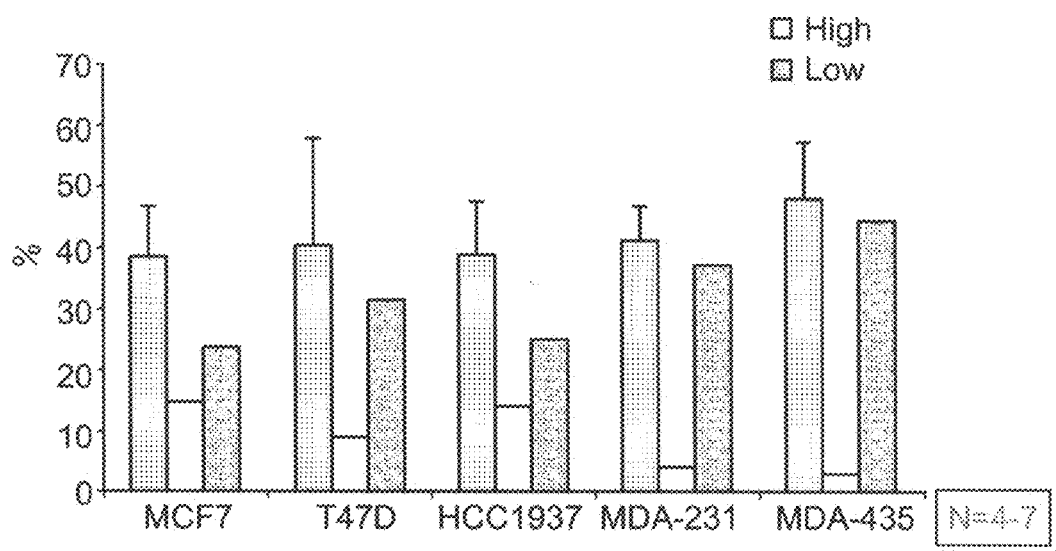

FIGS. 12a-b depicts FACS analysis of SEL-OB expression in various human carcinoma lines. FIG. 12a shows a SEL-OB-positive population of MCF7 cells, divided into high- and low-fluorescence intensity subpopulations. The high peak of the black curve shows low-intensity SEL-OB-expressing cells, and the low peak depicts the smaller, high-intensity subpopulation of cells. The red curve shows the blank. FIG. 12b shows the expression of SEL-OB analyzed on five breast cancer cell lines by FACS. The positive expression is not homogenous and results with peaks of high and low expression levels. The histogram summarizes total expression (dotted bars), high expression (white bars), and low expression (gray bars): 1, MCF7; 2, T-47D; 3, HCC1937; 4, MDA-231; 5, MDA-435.

Figure 13B:
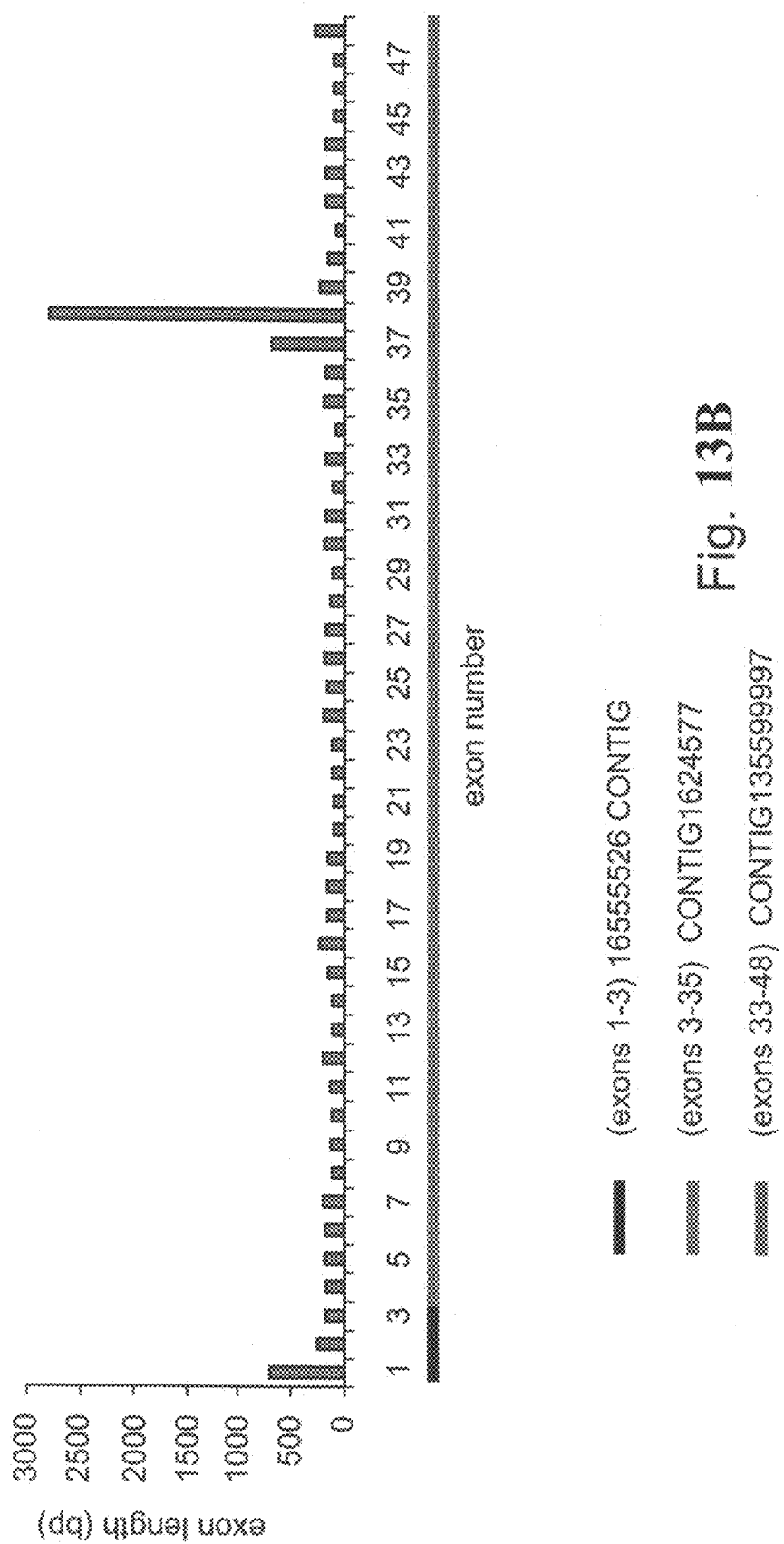

FIGS. 13a-b depict the predicted nucleotide sequence of the SEL-OB coding region, and the amino acid sequence it encodes (FIG. 13a, SEQ ID NOs: 17 and 15, respectively) and the exon structure of SEL-OB (FIG. 13b).

Figure 14A:
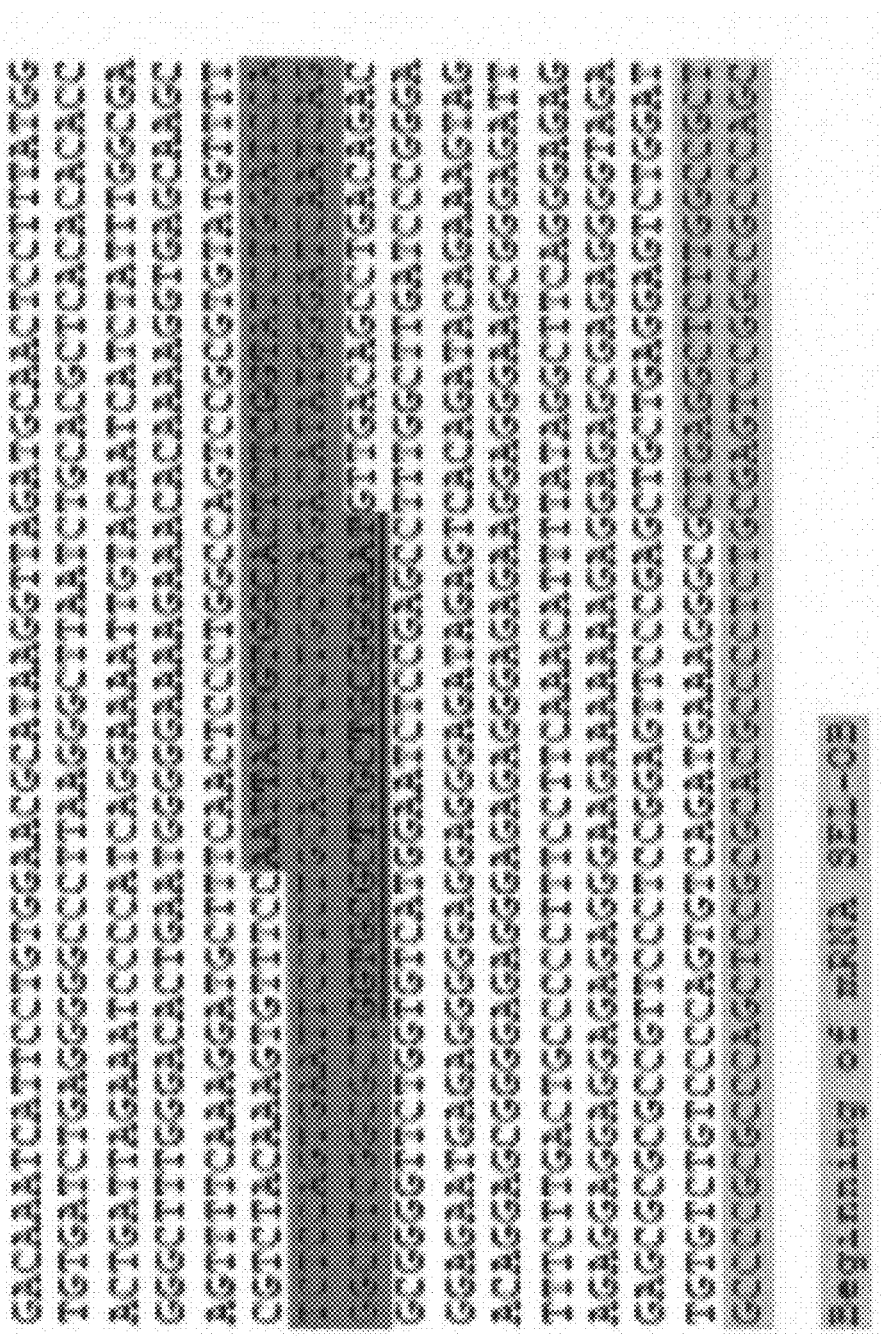
Figure 14B:

FIGS. 14a-b depict the nucleotide sequence of the predicted SEL-OB promoter region (FIG. 14a) and transcription factor binding sites found therein (FIG. 14b). The promoter region was predicted by SoftBerry promoter prediction analysis to be found at 34001-35500 by of the human genome contig 16555526, with a TATA box predicted at 1269 by of the sequence. Primers specific to SEL-OB promoter (F-SEQ ID NO: 11 and R-SEQ ID NO: 12) were designed by Primer3 software, at 969 by (F, FIG. 14a, first underlined sequence) and 1104 by (R, complementary sequence of second underlined sequence), respectively. The mRNA-coding region of SEL-OB begins at 1433 by at the transcription start site (FIG. 14a, yellow-shaded box). FIG. 14b shows certain transcription factor binding sites of the predicted promoter sequence (SEQ ID NO: 35), including the AP-1 binding site, shown at about 96 by in the promoter region.

Figure 15:
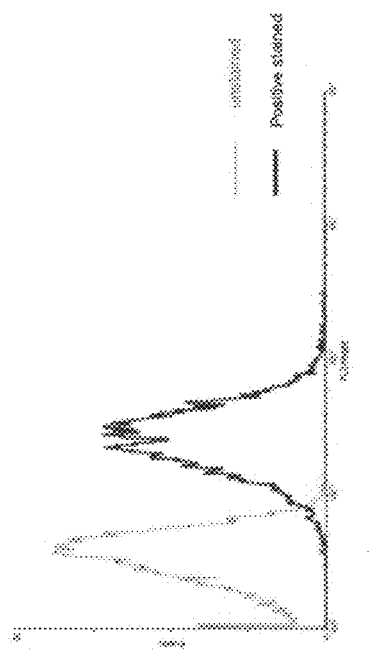

FIG. 15 is a graph showing CD45R expression on G2 cells.

Figure 16:
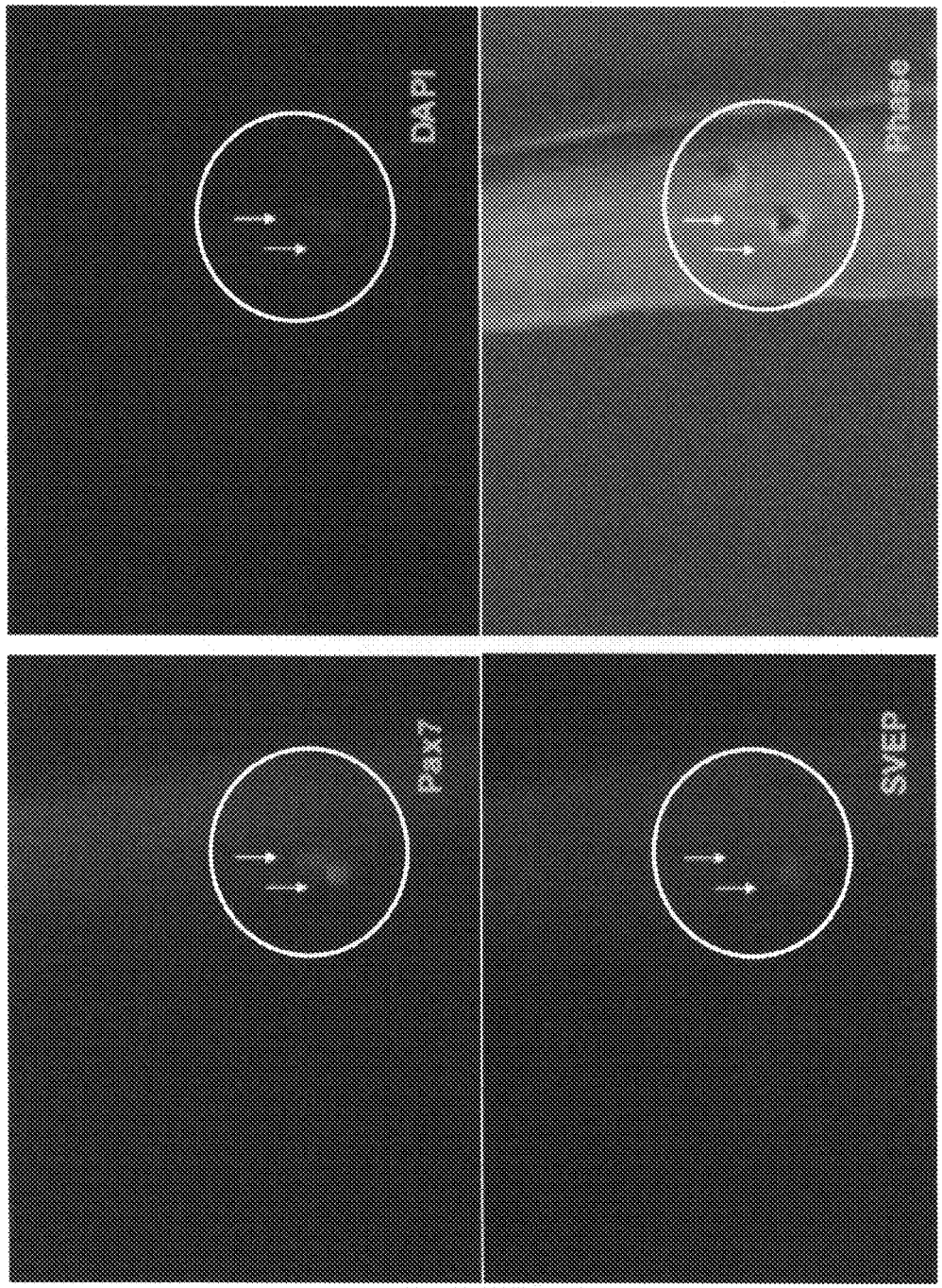

FIG. 16 shows co-staining of muscle fiber cells with Pax7 and SEL-OB substantiating SEL-OB as a satellite cell marker.

DESCRIPTION OF THE PREFERRED EMBODIMENTS

The present invention is of novel polypeptide sequences, polynucleotides encoding same and antibodies thereagainst which can be used to diagnose and treat cancer and skeletal disorders, such as osteoporosis.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Human bones are subject to a constant dynamic renovation process comprising bone resorption and bone formation. These processes are controlled by two types of cells specialized for these purposes. Osteoblasts, the cells from which bone develops, play a central role in bone formation by synthesizing and mineralizing bone matrices. Osteoclasts are large, multinucleate cells found in growing bones which resorb bony tissue by destruction of bone matrix. The majority of bone disorders are based on a disturbed equilibrium between bone formation and bone resorption. For example, osteoporosis is a disease characterized by low bone mass and enhanced bone fragility resulting in an increased risk of fractures. It results from a deficit in new bone formation versus bone resorption during the ongoing remodeling process.

Conventional treatment for disorders associated with enhanced bone resorption includes, for example, the administration of bisphosphonates, estrogens, estrogen/progesterone (hormone replacement therapy), estrogen agonists/antagonists (selective estrogen receptor modulators), calcitonin, vitamin D analogues, parathyroid hormone, growth hormone secretagogues, or sodium fluoride [Jardine et al., Annual Reports in Medicinal Chemistry 31 (1996) 211]. Unfortunately, these therapeutic agents still have significant shortcomings including increased risk of breast and uterine cancer, endometriosis, venous thromboembolism and cardiovascular events.

While reducing the present invention to practice, the present inventors have cloned a novel gene encoding for a skeletal cell surface protein, referred to herein as SEL-OB or SVEP1 (SEQ ID NOs: 14 and 15, respectively, see FIGS. 13a-c) with adhesion properties, which can be used for treating bone disorders and cancer.

As is illustrated hereinbelow and in the Examples section which follows, SEL-OB is a cell-surface protein expressed on skeletal cells and tumor cells. Specifically, as shown in Examples 1 and 6 of the Examples section which follows, in vivo expression analysis of SEL-OB showed confined expression to skeletal cells in bone marrow, periosteum and bone tissues and to tumor cells.

Bioinformatic analysis revealed that SEL-OB is 87% homologous to polydom genes [e.g., rat Polydom-like gene (GenBank Accession No. XP_232929) and mouse Polydom (GenBank Accession No. NP_073725)] which are implicated in cell adhesion and immune response (Gilges et al., 2000). SEL-OB specific antibody was used to immunoprecipitate a 370 KDa SEL-OB protein (with a predicted length of 3574 amino acids) from human bone marrow stromal cell lysates (see Example 4 of the Examples section which follows). The SEL-OB protein consists of a multi-domain structure comprising 34 CCP modules with a selectin superfamily signature, EGF domains and EGF-like Ca-binding domains. The EGF domain is a conserved motif found in many extracellular molecules. CCPs are presented by 60 amino acid repeats found in multiple copies and have a structural role as special spacers between other domains or may be directly implicated in the ligand binding. This domain is expressed in proteins of the coagulation system, of the complement cascade, and in selectins adhesion proteins (Bork et al., 1996; Davis, 1990). More domains identified in SEL-OB, such as PTX, vWF-A, pentraxin, Hyaline repeat domains, TNF receptor domain and cysteine-rich domains are found in the extracellular parts of receptors, such as TNF-R and ephrin, and may affect the biological specificity of the proteins as a part of the ligand-receptor complexes (Labrador et al., 1997). The vWFA domain binds to the complement proteins or the chain of integrins and exhibit residues that co-ordinate the binding of metal ions. vWFA is distributed in proteins that are implicated in the immune and haemostatic systems, cell adhesion or matrix assembly (Colombatti et al., 1993). HYR domain is a part of adhesive protein hyaline that is involved in cellular adhesion (Wessel et al., 1998). The unique domain composition places SEL-OB in the discrete group of membrane proteins which may be involved in cell adhesion processes.

The similarity of SEL-OB to selectin family is based on the presence of CCP modules with a selectin superfamily signature. In addition, both proteins possess the EGF and EGF-like Ca binding domains. The selectins (CD62) were identified on the surface of hematopoietic and endothelial cells and on bone marrow stromal cell (Kansas, 1996). These adhesion molecules mediate initial dynamic cell-cell interactions and contribute to the cellular localization in an appropriate niche (Calvi et al., 2003; Shi et al., 2003; Zhang et al., 2003). Such interactions were explored between hematopoietic stem cells and osteoblasts (Askenasy et al., 2002). The bone marrow microenvironment is composed of heterogeneous stromal cells and extra-cellular matrix (ECM) components. ECM serves not only as a scaffold to stabilize tissue structure, but also has been observed to influence the development, migration, proliferation, shape and metabolic function of cells that contact it. The nature of these interactions is based on the close relations between cells and relies on the expression of adhesion molecules and the constituents of ECM. Such interactions mediate processes, such as stem cell homing to specific sites, or lymphoid cells to sites of injury.

The identification of SEL-OB, a novel cell surface molecule, with a restricted tissue expression and domain structure of a cell adhesion molecule suggested involvement thereof in cell adhesion and homing. As is illustrated in Example 5 of the Examples section, immunohistochemical analysis and FACS demonstrated that SEL-OB has a role in vitro in cell adhesion. These results were substantiated by the demonstration that an anti SEL-OB antibody reduces cell attachment to the substrate.

The effect of estrogen on SEL-OB transcript expression was addressed in vitro and in vivo (see Example 3 of the Examples section which follows). As mentioned, estrogen is recognized to have a role in bone physiology, acting as a stimulator of bone formation in vivo and regulating proliferation of osteoblasts in vivo and in vitro (Tobias, 1999; Plant et al., 2001; 2002). Estrogen deficiency is a pathophysiology cause that disturbs skeletal function and results in postmenopausal osteoporosis, or in animal model following ovariectomy (Benayahu et al., 2000; Ishihara et al., 1999; Liu et al., 1999; Manolagas et al, 2002). Estrogen loss is a major reason for deterioration of bone structure and subsequent changes also lympho-hematopoietic cells, as observed in an animal model (Benayahu et al., 2000; Erlandsson et al., 2002; Onoe et al., 2000) and in osteoporotic patients (Cenci et al., 2003; Roggia et al., 2001). The nature of such changes relies on the effects of estrogen on adhesion molecules (Mendelsohn et al., 1999; Wren, 1992). In vivo analysis of SEL-OB expression in correlation with estrogen levels was effected in an animal model of ovaryectomy-induced osteoporosis (Benayahu et al, 2000). As is illustrated in Example 3 of the Examples section SEL-OB was detected in sham, but not OVX-rats with reduced estrogen levels. An up-regulation of SEL-OB mRNA in osteoblasts was detected in response to 17β-estradiol in vitro. These results show that SEL-OB is dynamically regulated by estrogen.

Estrogen has many functional effects on the skeleton; however, the precise mechanism of estrogen stimulation of bone formation is still unknown. According to the classical scheme, estrogen activity is mediated when the estrogen receptor (ER) binds to estrogen response elements (EREs) in the promoters of estrogen-regulated genes (Parker, 1998). In addition, estrogen receptor regulates gene transcription via protein—protein interactions with the AP-1 transcription complex in promoters of several genes (Kushner et al., 2000; Safe, 2001). Promoter analysis uncovered estrogen receptor binding to the SEL-OB promoter region including ERE and AP1 response elements known to participate in estrogen regulation. As shown in Example 3 of the Examples section which follows, ER and pcJun bound SEL-OB promoter, which binding was reversed in the presence of the estrogen antagonist ICI 182,780.

Altogether, the present findings suggest that the novel estrogen regulated SEL-OB protein expressed on skeletal and tumor cells serves as a cell adhesion molecule for enhancing bone formation and cell homing and as such can be used for generating potent diagnostic and therapeutic agents for cancer and skeletal disorders.

Thus, according to one aspect of the present invention there is provided an isolated polynucleotide encoding a polypeptide comprising an amino acid sequence being at least 60% at least 65% at least 70% at least 75% at least 80% at least 85% at least 86% at least 87% at least 88% at least 89% at least 90% at least 91% at least 92% at least 93% at least 94% at least 95% at least 96% at least 97% at least 98% at least 99% or 100% homologous to SEQ ID NO: 15 as determined by BlastP of the National Center of Biotechnology Information [(NCBI) http://worldwidewebdotncbiAotnihdotgov/BLAST/] using default parameters, the isolated polypeptide being capable of promoting cell adhesion and/or cell homing.

As used herein the phrase "an isolated polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

As used herein the phrase "cell adhesion" refers to the ability of a cell to bind another cell or an extracellular matrix component.

As used herein the term "homing" refers to the process by which circulating cells migrate to a target tissue or organ (e.g., the homing of human stromal cells to bone marrow).

According to a preferred embodiment of this aspect of the present invention the polypeptide includes an amino acid sequence which is at least 60% at least 65% at least 70% at least 75% at least 80% at least 85% at least 86% at least 87% at least 88% at least 89% at least 90% at least 91% at least 92% at least 93% at least 94% at least 95% at least 96% at least 97% at least 98% at least 99% or 100% identical to SEQ ID NO: 15 (i.e., SEL-OB), as determined using BlastP software of the National Center of Biotechnology Information (NCBI) using default parameters.

According to another preferred embodiment of this aspect of the present invention the nucleic acid sequence is as set forth in SEQ ID NO: 14 or 17.

Preferably, the polynucleotide according to this aspect of the present invention encodes a polypeptide, which is set forth in SEQ ID NO: 15.

As mentioned the isolated polypeptide of this aspect of the present invention is capable of promoting cell adhesion and/or cell homing.

According to yet another preferred embodiment of this aspect of the present invention, the isolated polynucleotide encodes for an active portion of SEL-OB polypeptides of the present invention.

As used hereinabove the phrase "active portion" refers to an amino acid sequence portion which is capable of displaying one or more functions of SEL-OB polypeptides of the present invention. Examples include, but are not limited to, cell homing, cell adhesion and antibody specific recognition. Examples of amino acid sequences of SEL-OB which are capable of generating SEL-OB adhesion activity include RGD (e.g., amino acid coordinates 2846-2848 of SEQ ID NO: 15), LDV (e.g., amino acid coordinates 1747-1749 of SEQ ID NO: 15) and LRE (e.g., amino acid coordinates 74-76 of SEQ ID NO: 15)

The isolated polynucleotides of the present invention can be qualified using hybridization assays. Thus, the isolated polynucleotides of the present invention are preferably hybridizable with SEQ ID NO: 14 or 17 under moderate to stringent hybridization conditions.

Moderate to stringent hybridization conditions are characterized by a hybridization solution such as containing 10% dextrane sulfate, 1 M NaCl, 1% SDS and 5×10$^6$ cpm $^{32}$P labeled probe, at 65° C., with a final wash solution of 0.2× SSC and 0.1% SDS and final wash at 65° C. and whereas moderate hybridization is effected using a hybridization solution containing 10% dextrane sulfate, 1 M NaCl, 1% SDS and 5×10$^6$ cpm $^{32}$P labeled probe, at 65° C., with a final wash solution of 1×SSC and 0.1% SDS and final wash at 50° C.

Thus, the present invention encompasses nucleic acid sequences described hereinabove; fragments thereof, sequences hybridizable therewith, sequences homologous thereto, sequences encoding similar polypeptides with different codon usage, altered sequences characterized by mutations, such as deletion, insertion or substitution of one or more nucleotides, either naturally occurring or man induced, either randomly or in a targeted fashion.

Since the polynucleotide sequences of the present invention encode previously unidentified polypeptides, the present invention also encompasses novel polypeptides of SEL-OB or portions thereof, which are encoded by the isolated polynucleotide and respective nucleic acid fragments thereof described hereinabove.

Thus, the present invention also encompasses polypeptides encoded by the novel SEL-OB nucleic acid sequences of the present invention. Examples of amino acid sequences of these novel polypeptides are set forth in SEQ ID NO: 15 and 13.

The present invention also encompasses homologs of these polypeptides, such homologs can be at least 60% at least 65% at least 70% at least 75% at least 80% at least 85% at least 86% at least 87% at least 88% at least 89% at least 90% at least 91% at least 92% at least 93% at least 94% at least 95% at least 96% at least 97% at least 98% at least 99% or more say 100% homologous to SEQ ID NOs: 15. Finally, the present invention also encompasses fragments of the above described polypeptides and polypeptides having mutations, such as deletion, insertion or substitution of one or more amino acids, either naturally occurring or man induced, either randomly or in a targeted fashion.

As mentioned hereinabove, the cell-adhesion and/or homing properties of the SEL-OB polypeptides of the present invention can be used in a number of therapeutic applications. For example, tumor cell metastasis such as to the bone can be prevented by a SEL-OB peptide encompassing the cell-adhesion domain, which may bind to the target organ (e.g., bone) and inhibit tumor spreading. In such applications it is highly desirable to employ the minimal and most efficacious peptide regions which still exert cell adhesion or homing activity. Identification of such peptide regions can be effected using various approaches, including, for example, display techniques.

Methods of constructing such display libraries are well known in the art. Such methods are described in, for example, Young A C, et al., "The three-dimensional structures of a polysaccharide binding antibody to *Cryptococcus neoformans* and its complex with a peptide from a phage display library: implications for the identification of peptide mimotopes" J Mol Biol 1997 Dec. 12; 274(4):622-34; Giebel L B et al. "Screening of cyclic peptide phage libraries identifies ligands that bind streptavidin with high affinities" Biochemistry 1995 Nov. 28; 34(47):15430-5; Davies E L et al., "Selection of specific phage-display antibodies using libraries derived from chicken immunoglobulin genes" J Immunol Methods 1995 Oct. 12; 186(1):125-35; Jones C R T al. "Current trends in molecular recognition and bioseparation" J Chromatogr A 1995 Jul. 14; 707(1):3-22; Deng S J et al. "Basis for selection of improved carbohydrate-binding single-chain antibodies from synthetic gene libraries" Proc Natl Acad Sci USA 1995 May 23; 92(11):4992-6; and Deng S J et al. "Selection of antibody single-chain variable fragments with improved carbohydrate binding by phage display" J Biol Chem 1994 Apr. 1; 269(13):9533-8, which are incorporated herein by reference.

Peptide sequences capable of mediating homing and or cell-adhesion activities can be also uncovered using computational biology which can model binding of selected peptide sequences to known ECM components or cell surface components.

It will be appreciated that peptides identified according to the teachings of the present invention may be degradation products, synthetic peptides or recombinant peptides as well as peptidomimetics, typically, synthetic peptides and peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C.A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as Phenylglycine, TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1) and non-conventional or modified amino acids (Table 2) which can be used with the present invention.

TABLE 1

| Amino Acid | Three-Letter Abbreviation | One-letter Symbol |
| --- | --- | --- |
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Ile | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisoleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |

TABLE 2-continued

| Non-conventional amino acid | Code | Non-conventional amino acid | Code |
|---|---|---|---|
| D-N-methylleucine | Dnmleu | N-(3-indolylethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine | Mval Nnbhm | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(l)glycine | Nnbhe |
| 1-carboxy-1-(2,2-diphenyl ethylamino)cyclopropane | Nmbc | | |

The peptides of the present invention are preferably utilized in a linear form, although it will be appreciated that in cases where cyclicization does not severely interfere with peptide characteristics, cyclic forms of the peptide can also be utilized.

The peptides of present invention can be biochemically synthesized such as by using standard solid phase techniques. These methods include exclusive solid phase synthesis, partial solid phase synthesis methods, fragment condensation, classical solution synthesis. These methods are preferably used when the peptide is relatively short (i.e., 10 kDa) and/or when it cannot be produced by recombinant techniques (i.e., not encoded by a nucleic acid sequence) and therefore involves different chemistry.

Solid phase peptide synthesis procedures are well known in the art and further described by John Morrow Stewart and Janis Dillaha Young, Solid Phase Peptide Syntheses (2nd Ed., Pierce Chemical Company, 1984).

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

In cases where large amounts of the peptides of the present invention are desired, the peptides of the present invention can be generated using recombinant techniques using a nucleic acid expression construct (further described hereinbelow). Recombinant production of polypeptides is described by Bitter et al., (1987) Methods in Enzymol. 153: 516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463 and further below.

As mentioned hereinabove SEL-OB protein or functional portions thereof can be used to treat skeletal disorders associated with bone resorption.

Thus, according to another aspect of the present invention there is provided a method of treating a disease associated with bone resorption in a subject in need thereof. The method comprising administering to the subject a therapeutically effective amount of:

(i) a SEL-OB polypeptide or an active portion thereof, as described hereinabove; and/or (ii) a polynucleotide encoding for the polypeptide, thereby treating the disease associated with bone resorption in the subject.

As used herein the term "subject" refers to a mammal, preferably a human subject.

As used herein the phrase "a disease associated with bone resorption" refers to a disease which results in bone loss, such as the bone loss resulting from excessive osteoclastic activity.

Examples of diseases which are associated with bone resrption include, but are not limited to, osteoporosis, osteopenia, hypercalcemia, jaw bone disorders, erosions associated with rheumatoid arthritis and Paget's disease and bone disorders associated with glucocorticoid, steroid, sex hormones and corticosteroid therapy.

As used herein the term "treating" refers to preventing, curing, reversing, attenuating, alleviating, minimizing, suppressing or halting the deleterious effects of a condition, a disease or a disorder (such as associated with bone resorption).

The SEL-OB polypeptide or active portion thereof can be administered to the subject per se or as part of a pharmaceutical composition where it is mixed with suitable carriers or excipients.

As used herein, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

As used herein, the term "active ingredient" refers to the SEL-OB polynucleotide, antibody, oligonucleotide, polypeptide or active portion thereof accountable for the intended biological effect.

Hereinafter, the phrases "physiologically acceptable carrier" and "pharmaceutically acceptable carrier," which may be used interchangeably, refer to a carrier or a diluent that does not cause significant irritation to an organism and does not abrogate the biological activity and properties of the administered compound. An adjuvant is included under these phrases.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

Techniques for formulation and administration of drugs may be found in the latest edition of "Remington's Pharmaceutical Sciences," Mack Publishing Co., Easton, Pa., which is herein fully incorporated by reference.

Suitable routes of administration may, for example, include oral, rectal, transmucosal, especially transnasal, intestinal, or parenteral delivery, including intramuscular, subcutaneous, and intramedullary injections, as well as intrathecal, direct intraventricular, intravenous, inrtaperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, and sodium carbomethylcellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichlorotetrafluoroethane, or carbon dioxide. In the case of a pressurized aerosol, the dosage may be determined by providing a valve to deliver a metered amount. Capsules and cartridges of, for example, gelatin for use in a dispenser may be formulated containing a powder mix of the compound and a suitable powder base, such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with, optionally, an added preservative. The compositions may be suspensions, solutions, or emulsions in oily or aqueous vehicles, and may contain formulatory agents such as suspending, stabilizing, and/or dispersing agents.

Pharmaceutical compositions for parenteral administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

Alternatively, the active ingredient may be in powder form for constitution with a suitable vehicle, e.g., a sterile, pyrogen-free, water-based solution, before use.

The pharmaceutical composition of the present invention may also be formulated in rectal compositions such as suppositories or retention enemas, using, for example, conventional suppository bases such as cocoa butter or other glycerides.

Pharmaceutical compositions suitable for use in the context of the present invention include compositions wherein the active ingredients are contained in an amount effective to achieve the intended purpose. More specifically, a "therapeutically effective amount" means an amount of active ingredients (e.g., a nucleic acid construct) effective to prevent, alleviate, or ameliorate symptoms of a disorder (e.g., ischemia) or prolong the survival of the subject being treated.

Determination of a therapeutically effective amount is well within the capability of those skilled in the art, especially in light of the detailed disclosure provided herein.

For any preparation used in the methods of the invention, the dosage or the therapeutically effective amount can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration, and dosage can be chosen by the individual physician in view of the patient's condition. (See, e.g., Fingl, E. et al. (1975), "The Pharmacological Basis of Therapeutics," Ch. 1, p. 1.)

Dosage amount and administration intervals may be adjusted individually to provide sufficient plasma or brain levels of the active ingredient to induce or suppress the biological effect (i.e., minimally effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks, or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA-approved kit, which may contain one or more unit dosage forms containing the active ingredient. The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a pharmaceutically acceptable carrier may also be prepared, placed in an appropriate container, and labeled for treatment of an indicated condition, as further detailed above.

As mentioned, SEL-OB polypeptides of the present invention can also be expressed from a nucleic acid construct comprising a SEL-OB polynucleotide (described hereinabove) administered to the subject employing any suitable mode of administration, described hereinabove (i.e., in-vivo gene therapy).

Alternatively, the nucleic acid construct is introduced into a suitable cell via an appropriate gene delivery vehicle/method (transfection, transduction, homologous recombination, etc.) and an expression system as needed and then the modified cells are expanded in culture and returned to the subject (i.e., ex-vivo gene therapy).

Thus, for example, polynucleotides encoding SEL-OB or an active portion thereof can be introduced into a population of osteoblasts (preferably autologous cells). Such cells can be retrieved from the subject by bone biopsy such as a drill biopsy or an open biopsy. Osteoblasts thus isolated, are expanded and infected in vitro prior to being re-introduced to the subject.

Regardless of the procedure employed for isolating osteoblasts, to enable cellular expression, SEL-OB polynucleotides of the present invention are ligated into nucleic acid expression constructs (also referred to herein as expression vectors) under the transcriptional control of a promoter sequence suitable (i.e., SEL-OB is operatively linked to the promoter) for directing constitutive, tissue specific or inducible transcription in the cells. One such promoter, is a nucleic acid sequence being at least 97% identical to SEQ ID NO: 16, as determined using BlastN analysis of NCBI using default parameters. As described hereinabove and in Example 2 of the Examples section which follows, this novel promoter sequence is capable of promoting SEL-OB expression in an estrogen regulatable manner.

Alternatively, constitutive promoters suitable for use with the present invention include sequences which are functional (i.e., capable of directing transcription) under most environmental conditions and most types of cells such as the cytomegalovirus (CMV) and Rous sarcoma virus (RSV).

Tissue specific promoters suitable for use with the present invention include sequences which are functional in skeletal cell populations, such as for example, Coll A1 promoter [Kuznetsov (2004) J. Cell Biol. 167:1113-22] and the osteocalcin promoter [Abboud (2003) J. Bone Miner. Res. 18:1386-94]. For review on bone tissue specific transcriptional control for targeting gene therapy to the skeleton see Stein (2000) Cancer 88:2899-902 and http://worldwideweb-dotopddottaudotacdotil/.

As mentioned above, the expression vector of the present invention may include additional sequences which render this vector suitable for replication and integration in prokaryotes, eukaryotes, or preferably both (e.g., shuttle vectors).

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

The nucleic acid construct of the present invention preferably further includes an appropriate selectable marker and/or an origin of replication. Preferably, the nucleic acid construct utilized is a shuttle vector, which can propagate both in E. coli (wherein the construct comprises an appropriate selectable marker and origin of replication) and be compatible for propagation in cells, or integration in a gene and a tissue of choice. The construct according to the present invention can be, for example, a plasmid, a bacmid, a phagemid, a cosmid, a phage, a virus or an artificial chromosome.

Examples of suitable constructs include, but are not limited to, pcDNA3, pcDNA3.1 (+/−), pGL3, PzeoSV2 (+/−), pDisplay, pEF/myc/cyto, pCMV/myc/cyto each of which is commercially available from Invitrogen Co. (worldwidewebdotinvitrogendotcom). Examples of retroviral vector and packaging systems are those sold by Clontech, San Diego, Calif., including Retro-X vectors pLNCX and pLXSN, which permit cloning into multiple cloning sites and the transgene is transcribed from CMV promoter. Vectors derived from Mo-MuLV are also included such as pBabe, where the transgene will be transcribed from the 5'LTR promoter.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

It will be appreciated that the SEL-OB polynucleotides, polypeptides or active portions thereof of the present invention can be provided to the subject with additional active agents to achieve an improved therapeutic effect as compared to treatment with each agent by itself.

For example, SEL-OB polynucleotides, polypeptides or active portions thereof for treating osteoporosis may be administered in combination with conventional osteoporosis treatments, for example in combination with agents like bisphosphonates, estrogens, estrogen/progesterone, estrogen agonists/antagonists, calcitonin, vitamin D analogues, parathyroid hormone, growth hormone secretagogues, or sodium fluoride.

In such therapy, measures (e.g., dosing and selection of the complementary agent) are taken to adverse side effects which may be associated with combination therapies.

Administration of such combination therapy can be simultaneous, such as in a single capsule having a fixed ration of these active agents, or in multiple capsules for each agent.

As mentioned hereinabove, SEL-OB is a cell adhesion molecule expressed on the cell-surface of cancer cells and immune system cells (see FIGS. 10a-d-11a-d) and mediates homing thereof such as to a bony tissue, suggesting that inhibition of this activity may be used to prevent osseous metastasis, and inflammatory diseases. The art teaches the use of anti adhesion molecules antibodies for the treatment of inflammatory diseases. See, for example, Khan S B, Allen A R, Bhangal G, Smith J, Lobb R R, Cook H T, Pusey C D. Blocking VLA-4 prevents progression of experimental crescentic glomerulonephritis. Nephron Exp Nephrol. 2003; 95(3):e100-10; and Miyamoto K, Ogura Y, Hamada M, Nishiwaki H, Hiroshiba N, Tsujikawa A, Mandai M, Suzuma K, Tojo S J, Honda Y. In vivo neutralization of P-selectin inhibits leukocyte-endothelial interactions in retinal microcirculation during ocular inflammation. Microvasc Res. 1998 May; 55(3):230-40.

As shown in Example 8 of the Examples section which follows, treatment of hematopoietic cells (G2, pre-B acute lymphoblastic leukemia cells) with an anti-SEL-OB antibody markedly reduced cell homing to the spleen of tested recipients as compared to control untreated cells. These results place SEL-OB critical to cell homing and as such downregulation of same is expected to be of therapeutic value in the treatment of cancer (prevention of cancer metastasis) as well as inflammatory diseases associated with cell homing.

Thus, according to yet another aspect of the present invention there is provided a method of treating cancer and/or an inflammatory disease in a subject in need thereof, the method comprising administering to the subject a therapeutically effective amount of an agent for down-regulating in cells of the subject a level and/or an activity of a SEL-OB polypeptide (described hereinabove), thereby treating the cancer and/or the inflammatory disease in the subject.

As used herein the term "cancer" refers to a malignant growth or tumor caused by abnormal and uncontrolled cell division, which may spread to other parts of the body (e.g., bones). Examples of cancer, which may metastasize to bones include, but are not limited to, breast cancer, prostate cancer, lung cancer, thyroid cancer, renal cancer, myeloma, blastoma, lymphoma and melanoma.

An "inflammatory disease or condition" as used herein refers to any condition characterized by local inflammation at a site of injury or infection and includes autoimmune diseases, certain forms of infectious inflammatory states, undesirable neutrophil activity characteristic of organ transplants or other implants and virtually any other condition characterized by unwanted neutrophil accumulation at a local tissue site. These conditions include but are not limited to meningitis, cerebral edema, arthritis, nephritis, adult respiratory distress syndrome, pancreatitis, myositis, neuritis, connective tissue diseases, phlebitis, arteritis, vasculitis, allergy, anaphylaxis, ehrlichiosis, gout, organ transplants and/or ulcerative colitis.

Downregulation of SEL-OB can be effected on the genomic and/or the transcript level using a variety of molecules that interfere with transcription and/or translation [e.g., estrogen antagonists (see Example 3 of the Examples section) antisense, siRNA, Ribozyme, or DNAzyme], or on the protein level using, e.g., antibodies, as further described hereinbelow.

Following is a non-comprehensive list of agents capable of downregulating expression level and/or activity of SEL-OB.

One example of an agent capable of downregulating activity of SEL-OB is an antibody or antibody fragment capable of specifically binding SEL-OB.

As used herein the term "antibody capable of specifically binding a SEL-OB polypeptide" refers to an antibody which immunospecifically binds to a SEL-OB antigen and preferably not to other sequences not having the amino acid coordinates (1587-1589 of SEQ ID NO: 15).

For example, the antibody of this aspect of the present invention may specifically bind at least one epitope unique to SEL-OB, such as the unique epitopes located in the amino acid sequence set forth in SEQ ID NO: 13. As used herein, the term "epitope" refers to any antigenic determinant on an antigen to which the paratope of an antibody binds. Other peptides which may be used for generating antibodies against SEL-OB include but are not limited to those provided in SEQ ID NOs.: 23-27 listed in Table 3 below.

TABLE 3

| Peptide | Localization | Sequence/SEQ ID NO: | Antigenic score* | Cross reactivity human/mouse |
|---|---|---|---|---|
| 1 | 212aa | RDSGVEIF/SEQ ID NO: 23 | 2.9 | RDSGVEIF<br>RDFGVEIF |
| 2 | 876aa | RLDYSYDDF/SEQ ID NO: 24 | 4.6 | RLDYSYDDF<br>RLDYSYDHF |
| 3 | 1534aa | DGGAGLSVGLPIPGMFG/SEQ ID NO: 25 | 2.8 | |
| 4 | 2819aa | QDDKNWDE/SEQ ID NO: 26 | 4.6 | QDDKNWDE<br>QENRDWDG |
| 5 | 3426aa | ENAIARGVHYQYGD/SEQ ID NO: 27 | 3.6 | M/R/H |

*http://worldwidewebdotopenbiosystemsdotcom/antigen/indexdotphp

Such an antibody is preferably selected to inhibit cell-adhesion and/or homing activity of SEL-OB, thereby serving as a neutralizing antibody. An Example of generating such a neutralizing antibody is described in Examples 4-5 of the Examples section which follows.

Epitopic determinants usually consist of chemically active surface groupings of molecules such as amino acids or carbohydrate side chains and usually have specific three-dimensional structural characteristics, as well as specific charge characteristics.

The term "antibody" as used in this invention includes any intact molecules and functional fragments thereof, such as Fab, F(ab')2, and Fv, that are capable of binding to macrophages. The functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of a heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single-chain Antibody ("SCA"), a genetically engineered molecule containing the variable region of the light chain and the variable region of the heavy chain, linked by a suitable polypeptide linker as a genetically fused single-chain molecule.

Methods of producing polyclonal and monoclonal antibodies as well as fragments thereof are well known in the art. (See, for example, Harlow, E. and Lane, D. (1988). Antibodies: A Laboratory Manual, Cold Spring Harbor Laboratory, New York, incorporated herein by reference.)

Antibody fragments according to the present invention can be prepared by proteolytic hydrolysis of the antibody or by expression in *E. coli* or mammalian cells (e.g., by Chinese hamster ovary (CHO) cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin directly produces two monovalent Fab' fragments and an Fc (constant region) fragment. Such methods are described, for example, by Goldenberg in U.S. Pat. Nos. 4,036,945 and 4,331,647, and in references contained therein, the patents being hereby incorporated by reference in their entirety. (See also Porter, R. R. (1959). The hydrolysis of rabbit gammaglobulins and antibodies by crystalline papain. Biochem J 73, 119-126.) Other methods of cleaving antibodies, such as separation of heavy chains to form monovalent light-heavy chain fragments, further cleavage of fragments, or other enzymatic, chemical, or genetic techniques, may also be used, so long as the fragments bind to the antigen that is recognized by the intact antibody.

$F_v$ fragments comprise an association of variable heavy (VH) and variable light (VL) chains. This association may be noncovalent, as described in Inbar, D. et al. (1972). Localization of Antibody-Combining Sites within the Variable Portions of Heavy and Light Chains. Proc Natl Acad Sci USA 69, 2659-2662. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as *E. coli*. The recombinant host cell synthesizes a single polypeptide chain with a linker peptide bridging the two V domains. Methods for producing sFvs are described, for example, in: Whitlow, M. and Filpula, D. (1991). Single-chain Fv proteins and their fusion proteins. METHODS: A Companion to Methods in Enzymology 2(2), 97-105; Bird, R. E. et al. (1988). Single-chain antigen-binding proteins. Science 242, 423-426; Pack, P. et al. (1993). Improved bivalent miniantibodies, with identical avidity as whole antibodies, produced by high cell density fermentation of *Escherichia coli*. Biotechnology (N.Y.) 11(11), 1271-1277; and U.S. Pat. No. 4,946,778, which is hereby incorporated by reference in its entirety.

Another form of antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick, J. W. and Fry, K. E. (1991). PCR Amplification of Antibody Genes. METHODS: A Companion to Methods in Enzymology 2(2), 106-110.

Humanized forms of non-human (e.g., murine) antibodies are chimeric molecules of immunoglobulins, immunoglobulin chains, or fragments thereof (such as Fv, Fab, Fab', F(ab').sub.2, or other antigen-binding subsequences of antibodies) that contain minimal sequence derived from non-human immunoglobulin. Humanized antibodies include human immunoglobulins in which residues forming a CDR of the recipient (recipient antibody) are replaced by residues from a CDR of a non-human species (donor antibody), such as mouse, rat, or rabbit, with the desired specificity, affinity, and capacity. In some instances, the Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR corresponds to that of a non-human immunoglobulin, and all or substantially all of the framework region (FR) is that of a human immunoglobulin consensus sequence. The humanized antibody optimally also will comprise at least a portion of an immunoglobulin constant region (Fc), typically that of a human immunoglobulin (Jones, P. T. et al. (1986). Replacing the complementarity-determining regions in a human antibody with those from a mouse. Nature 321, 522-525; Riechmann, L. et al. (1988). Reshaping human antibodies for therapy. Nature 332, 323-327; Presta, L. G. (1992b). Curr Opin Struct Biol 2, 593-596; and Presta, L. G. (1992a). Antibody engineering. Curr Opin Biotechnol 3(4), 394-398).

Methods for humanizing non-human antibodies are well known in the art. Generally, a humanized antibody has one or more amino acid residues from a non-human source introduced into it. These non-human amino acid residues are often referred to as import residues, which are typically taken from an import variable domain. Humanization can be essentially performed following the method of Winter and co-workers (see Jones et al. (1986); Riechmann et al. (1988); and Verhoeyen, M. et al. (1988). Reshaping human antibodies: grafting an antilysozyme activity. Science 239, 1534-1536), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogueous sites in rodent antibodies.

Human antibodies can also be produced using various techniques known in the art, including phage display libraries (Hoogenboom, H. R. and Winter, G. (1991). By-passing immunisation. Human antibodies from synthetic repertoires of germline VH gene segments rearranged in vitro. J Mol Biol 227, 381-388). The techniques of Cole et al. and Boemer et al. are also available for the preparation of human monoclonal antibodies (Cole et al. (1985), Monoclonal Antibodies and Cancer Therapy, Alan R. Liss, Inc., pp. 77-96; and Boerner, P. et al. (1991). Production of antigen-specific human monoclonal antibodies from in vitro-primed human splenocytes. J Immunol 147, 86-95). Similarly, human antibodies can be made by introduction of human immunoglobulin loci into transgenic animals, e.g., mice, in which the endogenous immunoglobulin genes have been partially or completely inactivated. Upon challenge, human antibody production is observed to closely resemble that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; and 5,661,016; and in the following scientific publications: Marks, J. D. et al. (1992). By-passing immunization: building high affinity human antibodies by chain shuffling. Biotechnology (N.Y.) 10(7), 779-783; Lonberg et al., 1994. Nature 368:856-859; Morrison, S. L. (1994). News and View: Success in Specification. Nature 368, 812-813; Fishwild, D. M. et al. (1996). High-avidity human IgG kappa monoclonal antibodies from a novel strain of minilocus transgenic mice. Nat Biotechnol 14, 845-851; Neuberger, M. (1996). Generating high-avidity human Mabs in mice. Nat Biotechnol 14, 826; and Lonberg, N. and Huszar, D. (1995). Human antibodies from transgenic mice. Int Rev Immunol 13, 65-93.

To improve therapeutic efficacy, antibodies of the present invention are preferably conjugated to a therapeutic moiety. Essentially binding of the antibody to the cell surface of the target cell (e.g., cancer cell) is followed by endocytosis of the therapeutic complex (antibody-therapeutic moiety) and cell death. Examples of therapeutic moieties which can be used in accordance with the present invention include, but are not limited to, toxins, proapoptotic factors, a chemotherapeutic agents and radio-isotopes.

Examples of chemotherapeutic agents include, but are not limited to, alkylating agents, folic acid antagonists, anti-metabolites of nucleic acid metabolism, antibiotics, pyrimidine analogs, 5-fluorouracil, cisplatin, purine nucleosides, amines, amino acids, triazol nucleosides, or corticosteroids. Specific examples include Adriamycin, Doxorubicin, 5-Fluorouracil (5FU), 1-Carboxymethyl-5-Fluorouracil (CMFU), Cytosine arabinoside (Ara-C), Cyclophosphamide, Thiotepa, Busulfan, Cytoxin, Taxol, Toxotere, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Carminomycin, Aminopterin, Dactinomycin, Mitomycins, Esperamicins (see U.S. Pat. No. 4,675,187), Melphalan, and other related nitrogen mustards. Also included in this definition are hormonal agents that act to regulate or inhibit hormone action on tumors, such as tamoxifen and onapristone.

Examples of radio-isotopes include cytotoxic radio-isotopes such as β radiation emitters, γ emitters and α-radiation emitting materials. Examples of β radiation emitters which are useful as cytotoxic agents, include isotopes such as scandium-46, scandium-47, scandium-48, copper-67, gallium-72, gallium-73, yttrium-90, ruthenium-97, palladium-100, rhodium-101, palladium-109, samarium-153, rhenium-186, rhenium-188, rhenium-189, gold-198, radium-212 and lead-212. The most useful γ emitters are iodine-131 and indium-m 114. Other radio-isotope useful with the invention include α-radiation emitting materials such as bismuth-212, bismuth-213, and At-211 as well as positron emitters such as gallium-68 and zirconium-89.

Examples of enzymatically active toxins and fragments thereof which can be used as cytotoxic agents include diphtheria A chain toxin, non-binding active fragments of diphtheria toxin, exotoxin A chain (from *Pseudomonas aeruginosa*), shiga toxin, verotoxin, ricin A chain, abrin A chain toxin, modeccin A chain toxin, α-sarcin toxin, Abrus precatorius toxin, amanitin, pokeweed antiviral protein, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes.

Conjugates of antibodies (or peptides) and therapeutic moieties of the present invention are generated using any conjugation method known in the art. For example by using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bisazido compounds (such as bis-(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). Alternatively, when the therapeutic moiety is a polypeptide (e.g., a pro-apoptotic factor such as Fas-L), recombinant techniques may be used to generate the conjugates of the present invention.

Another agent capable of downregulating SEL-OB is a small interfering RNA (siRNA) molecule in the process of RNA interference (RNAi). RNAi is a two-step process. In the first, the initiation step, input double-stranded (dsRNA) is digested into 21- to 23-nucleotide (nt) small interfering RNAs (siRNAs), probably by the action of Dicer, a member of the RNase III family of dsRNA-specific ribonucleases, which processes (cleaves) dsRNA (introduced directly or by means of a transgene or a virus) in an ATP-dependent manner. Successive cleavage events degrade the RNA to 19- to 21-bp duplexes (the siRNA), each with 2-nucleotide 3' overhangs (Hutvagner, G. and Zamore. P. D. (2002). RNAi: Nature abhors a double-strand. Curr Opin Gen Dev 12, 225-232; and Bernstein, E. (2001). Role for a bidentate ribonuclease in the initiation step of RNA interference. Nature 409, 363-366).

In the second step, termed the effector step, the siRNA duplexes bind to a nuclease complex to form the RNA-induced silencing complex (RISC). An ATP-dependent unwinding of the siRNA duplex is required for activation of the RISC. The active RISC then targets the homologous transcript by base-pairing interactions and cleaves the mRNA into 12-nucleotide fragments from the 3' terminus of the siRNA (Hutvagner and Zamore (2002); Hammond et al. (2001) Nat. Rev. Gen. 2:110-119 (2001); and Sharp, P. A. (2001). RNA interference. Genes Dev 15, 485-490). Although the mechanism of cleavage remains to be elucidated, research indicates that each RISC contains a single siRNA and an RNase (Hutvagner and Zamore (2002)).

Because of the remarkable potency of RNAi, an amplification step within the RNAi pathway has been suggested. Amplification could occur by copying of the input dsRNAs to generate more siRNAs, or by replication of the siRNAs formed. Alternatively or additionally, amplification could be effected by multiple turnover events of the RISC (Hammond et al. (2001), Sharp (2001); and Hutvagner and Zamore (2002)). For more information on RNAi, see the following reviews: Tuschl, T. (2001). RNA interference and small interfering RNAs. ChemBioChem 2, 239-245; Cullen, B. R. (2002). RNA interference: antiviral defense and genetic tool. Nat Immunol 3, 597-599; and Brantl, S. (2002). Antisense-RNA regulation and RNA interference. Biochim Biophys Acta 1575, 15-25.

Synthesis of RNAi molecules suitable for use with the present invention can be effected as follows. First, the SEL-OB mRNA sequence is scanned downstream of the AUG start codon for AA-dinucleotide sequences. Occurrence of each AA and the 19 3'-adjacent nucleotides is recorded as a potential siRNA target site. Preferably, siRNA target sites are selected from the open reading frame (ORF), as untranslated regions (UTRs) are richer in regulatory protein binding sites. UTR-binding proteins and/or translation initiation complexes may interfere with binding of the siRNA endonuclease complex (Tuschl (2001)). It will be appreciated, however, that siRNAs directed at untranslated regions may also be effective, as demonstrated for GAPDH, wherein siRNA directed at the 5' UTR mediated about a 90% decrease in cellular GAPDH mRNA and completely abolished protein levels (worldwidewebdotambiondotcom/techlib/tn/91/912 dothtml).

Second, potential target sites are compared to an appropriate genomic database (e.g., human, mouse, rat, etc.) using any sequence alignment software, such as the BlastN software available from the NCBI server (worldwidewebdotncbidotnlmdotnihdotgov/BLAST/). Putative target sites that exhibit significant homology to other coding sequences are filtered out.

Qualifying target sequences are selected as templates for siRNA synthesis. Preferred sequences are those including low G/C content, as these have proven to be more effective in mediating gene silencing as compared with sequences including G/C content higher than 55%. Several target sites are preferably selected along the length of the target gene for evaluation. For better evaluation of the selected siRNAs, a negative control is preferably used in conjunction. Negative-control siRNAs preferably include the same nucleotide composition as the siRNAs but lack significant homology to the genome. Thus, a scrambled nucleotide sequence of the siRNA is preferably used, provided it does not display any significant homology to any other gene.

For example, a suitable SEL-OB siRNA target sequence can be the sequences set forth in SEQ ID NOs: 18-22 (Dharmacon, Inc., Lafayette, Colo.).

Another agent capable of downregulating SEL-OB is a DNAzyme molecule, which is capable of specifically cleaving an mRNA transcript or a DNA sequence of the SEL-OB. DNAzymes are single-stranded polynucleotides that are capable of cleaving both single- and double-stranded target sequences (Breaker, R. R. and Joyce, G. F. (1995). A DNA enzyme with $Mg^{2+}$-dependent RNA phosphoesterase activity. Curr Biol 2, 655-660; Santoro, S. W. and Joyce, G. F. (1997). A general purpose RNA-cleaving DNA enzyme. Proc Natl Acad Sci USA 94, 4262-4266). A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine: pyrimidine junctions (Santoro and Joyce (1997)); for review of DNAzymes, see: Khachigian, L. M. (2002). DNAzymes: cutting a path to a new class of therapeutics. Curr Opin Mol Ther 4, 119-121.

Examples of construction and amplification of synthetic, engineered DNAzymes recognizing single- and double-stranded target cleavage sites are disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh, T. et al., Abstract 409, American Society of Gene Therapy 5th Annual Meeting (worldwidewebdotasgtdotorg), Jun. 5-9, 2002, Boston, Mass. USA.). In another application, DNAzymes complementary to bcr-abl oncogenes were successful in inhibiting the oncogene's expression in leukemia cells, and in reducing relapse rates in autologous bone marrow transplants in cases of Chronic Myelogenous Leukemia (CML) and Acute Lymphoblastic Leukemia (ALL).

Downregulation of a SEL-OB can also be effected by using an antisense polynucleotide capable of specifically hybridizing with an mRNA transcript encoding the SEL-OB protein.

Design of antisense molecules that can be used to efficiently downregulate a SEL-OB must be effected while considering two aspects important to the antisense approach. The first aspect is delivery of the oligonucleotide into the cytoplasm of the appropriate cells, while the second aspect is design of an oligonucleotide that specifically binds the designated mRNA within cells in a manner inhibiting the translation thereof.

The prior art teaches of a number of delivery strategies which can be used to efficiently deliver oligonucleotides into a wide variety of cell types (see, for example: Luft, F. C. (1998). Making sense out of antisense oligodeoxynucleotide delivery: getting there is half the fun. J Mol Med 76(2), 75-76 (1998); Kronenwett et al. (1998). Oligodeoxyribonucleotide uptake in primary human hematopoietic cells is enhanced by cationic lipids and depends on the hematopoietic cell subset. Blood 91, 852-862; Rajur, S. B. et al. (1997). Covalent protein-oligonucleotide conjugates for efficient delivery of antisense molecules. Bioconjug Chem 8, 935-940; Lavigne et al. Biochem Biophys Res Commun 237: 566-71 (1997); and Aoki, M. et al. (1997). In vivo transfer efficiency of antisense oligonucleotides into the myocardium using HVJ-liposome method. Biochem Biophys Res Commun 231, 540-545).

In addition, also available are algorithms for identifying those sequences with the highest predicted binding affinity for their target mRNA based on a thermodynamic cycle that accounts for the energetics of structural alterations in both the target mRNA and the oligonucleotide (see, for example, Walton, S. P. et al. (1999). Prediction of antisense oligonucleotide binding affinity to a structured RNA target. Biotechnol Bioeng 65, 1-9).

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF-alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiencies of specific oligonucleotides using an in vitro system were also published (Matveeva, O. et al. (1998). Prediction of antisense oligonucleotide efficacy by in vitro methods. Nature Biotechnology 16, 1374-1375).

Several clinical trials have demonstrated the safety, feasibility, and activity of antisense oligonucleotides. For example, antisense oligonucleotides suitable for the treatment of cancer have been successfully utilized (Holmund, B. P. et al. (1999). Toward antisense oligonucleotide therapy for cancer: ISIS compounds in clinical development. Curr Opin Mol Ther 1, 372-385), while treatment of hematological malignancies via antisense oligonucleotides targeting c-myb gene, p53, and Bcl-2 entered clinical trials and was shown to be tolerated by patients (Gewirtz, A. M. (1999). Oligonucleotide therapeutics: clothing the emperor. Curr Opin Mol Ther 1, 297-306).

More recently, antisense-mediated suppression of human heparanase gene expression was reported to inhibit pleural dissemination of human cancer cells in a mouse model (Uno, F. et al. (2001). Antisense-mediated suppression of human heparanase gene expression inhibits pleural dissemination of human cancer cells. Cancer Res 61, 7855-7860).

Thus, the current consensus is that recent developments in the field of antisense technology, which, as described above, have led to the generation of highly accurate antisense design algorithms and a wide variety of oligonucleotide delivery systems, enable an ordinarily skilled artisan to design and implement antisense approaches suitable for downregulating expression of known sequences without having to resort to undue trial and error experimentation.

Another agent capable of downregulating SEL-OB is a ribozyme molecule capable of specifically cleaving an mRNA transcript encoding a SEL-OB polypeptide. Ribozymes increasingly are being used for the sequence-specific inhibition of gene expression by the cleavage of mRNAs encoding proteins of interest (Welch, P. J. et al. (1998). Expression of ribozymes in gene transfer systems to modulate target RNA levels. Curr Opin Biotechnol 9, 486-496). The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers, and specific somatic mutations in genetic disorders (Welch, P. J. et al. (1998). Ribozyme gene therapy for hepatitis C virus infection. Clin Diagn Virol 10, 163-171). Most notably, several ribozyme gene therapy protocols for HIV patients are already in Phase 1 trials. More recently, ribozymes have been used for transgenic animal research, gene target validation, and pathway elucidation. Several ribozymes are in various stages of clinical trials. ANGIOZYME™ was the first chemically synthesized ribozyme to be studied in human clinical trials. ANGIOZYME specifically inhibits formation of the VEGFR (Vascular Endothelial Growth Factor receptor), a key component in the angiogenesis pathway. Ribozyme Pharmaceuticals, Inc., as well as other firms, has demonstrated the importance of anti-angiogenesis therapeutics in animal models. HEPTAZYME™, a ribozyme designed to selectively destroy Hepatitis C Virus (HCV) RNA, was found effective in decreasing Hepatitis C viral RNA in cell culture assays (Ribozyme Pharmaceuticals, Inc., Boulder, Colo., USA (worldwidewebdotrpidotcom)).

An additional method of regulating the expression of a SEL-OB gene in cells is via triplex-forming oligonucleotides (TFOs). Recent studies show that TFOs can be designed to recognize and bind to polypurine or polypirimidine regions in double-stranded helical DNA in a sequence-specific manner. These recognition rules are outlined in: Maher III, L. J., et al. (1989). Inhibition of DNA binding proteins by oligonucleotide-directed triple helix formation. Science 245, 725-730; Moser, H. E., et al. (1987). Sequence-specific cleavage of double helical DNA by triple helix formation. Science 238, 645-650; Beal, P. A. and Dervan, P. B. (1991). Second structural motif for recognition of DNA by oligonucleotide-directed triple-helix formation. Science 251, 1360-1363; Cooney, M., et al. (1988). Science 241, 456-459; and Hogan, M. E., et al., EP Publication 375408. Modifications of the oligonucleotides, such as the introduction of intercalators and backbone substitutions, and optimization of binding conditions (e.g., pH and cation concentration) have aided in overcoming inherent obstacles to TFO activity such as charge repulsion and instability, and it was recently shown that synthetic oligonucleotides can be targeted to specific sequences (for a recent review, see Seidman, M. M. and Glazer, P. M. (2003). The potential for gene repair via triple helix formation J Clin Invest 112, 487-494).

In general, the triplex-forming oligonucleotide has the sequence correspondence:

| oligo  | 3'--A | G | G | T |
| duplex | 5'--A | G | C | T |
| duplex | 3'--T | C | G | A |

However, it has been shown that the A-AT and G-GC triplets have the greatest triple-helical stability (Reither, S. and Jeltsch, A. (2002). Specificity of DNA triple helix formation analyzed by a FRET assay. BMC Biochem 3(1), 27, Epub). The same authors have demonstrated that TFOs designed according to the A-AT and G-GC rule do not form nonspecific triplexes, indicating that triplex formation is indeed sequence-specific.

Thus, a triplex-forming sequence may be devised for any given sequence in the SEL-OB regulatory region (SEQ ID NO: 16). Triplex-forming oligonucleotides preferably are at least 15, more preferably 25, still more preferably 30 or more, nucleotides in length, up to 50 or 100 bp.

Transfection of cells with TFOs (for example, via cationic liposomes) and formation of the triple-helical structure with the target DNA induces steric and functional changes, blocking transcription initiation and elongation, allowing the introduction of desired sequence changes in the endogenous DNA, and resulting in the specific downregulation of gene expression. Examples of suppression of gene expression in cells treated with TFOs include: knockout of episomal supFG1 and endogenous HPRT genes in mammalian cells (Vasquez, K. M. et al. (1999). Chromosomal mutations induced by triplex-forning oligonucleotides in mammalian cells. Nucl Acids Res 27, 1176-1181; and Puri, N. et al. (2001). Targeted Gene Knockout by 2'-O-Aminoethyl Modified Triplex Forming Oligonucleotides. J Biol Chem 276, 28991-28998); the sequence- and target-specific downregulation of expression of the Ets2 transcription factor, important in prostate cancer etiology (Carbone, G. M. et al., Selective inhibition of transcription of the Ets2 gene in prostate cancer cells by a triplex-forming oligonucleotide. Nucl Acids Res 31, 833-843); and regulation of the pro-inflammatory ICAM-1 gene (Besch, R. et al. (2003). Specific inhibition of ICAM-1 expression mediated by gene targeting with Triplex-forming oligonucleotides. J Biol Chem 277, 32473-32479). In addition, Vuyisich and Beal have recently shown that sequence-specific TFOs can bind to dsRNA, inhibiting activity of dsRNA-dependent enzymes such as RNA-dependent kinases (Vuyisich, M. and Beal, P. A. (2000). Regulation of the RNA-dependent protein kinase by triple helix formation. Nucl Acids Res 28, 2369-2374).

Additionally, TFOs designed according to the abovementioned principles can induce directed mutagenesis capable of effecting DNA repair, thus providing both downregulation and upregulation of expression of endogenous genes (Seidman and Glazer (2003)). Detailed description of the design, synthesis, and administration of effective TFOs can be found in U.S. patent application Ser. Nos. 03/017,068 and 03/0096980 to Froehler et al. and Ser. Nos. 02/012,8218 and 02/012,3476 to Emanuele et al., and U.S. Pat. No. 5,721,138 to Lawn.

Aside from therapeutic applications, SEL-OB can be used as a diagnostic marker for diseases associated with bone resorption. As shown in Example 3 of the Examples section which follows, SEL-OB expression is regulated by estrogen and thus low levels thereof may be indicative of low estrogen levels which are directly correlated with loss of bone mass.

Thus, according to still another aspect of the present invention there is provided a method of diagnosing a presence of, or a predisposition to a disease associated with bone resorption in a subject.

The method comprising detecting in a tissue and/or a cell of the subject an absence, a presence and/or a level of a polypeptide as set forth in SEQ ID NO: 15 (SEL-OB) or a polynucleotide encoding the polypeptide, wherein the absence, presence and/or the level of the polypeptide or the polynucleotide in the tissue or cell of the subject is indicative of a presence of, or a predisposition to the skeletal disorder in the subject.

Detecting absence presence and/or level of SEL-OB may be effected in a biological sample obtained from the subject (ex-vivo) such as by bone biopsy described hereinabove, or directly in the subject. Determination of SEL-OB expression is preferably effected also in normal cells (or normal healthy subjects), to normalize gene expression.

As mentioned above, determination of the level of SEL-OB can be effected at the transcriptional level (i.e., mRNA) using an oligonucleotide probe, which is capable of specifically hybridizing to the sequence (e.g., SEQ ID Nos: 3 or 4). Hybridization of oligonucleotide probes can be detected using a variety of methods known to those of skill in the art (e.g., calorimetric assays, amplification assays and the like).

The term "oligonucleotide" refers to a single stranded or double stranded oligomer or polymer of ribonucleic acid (RNA) or deoxyribonucleic acid (DNA) or mimetics thereof. This term includes oligonucleotides composed of naturally-occurring bases, sugars and covalent internucleoside linkages (e.g., backbone) as well as oligonucleotides having non-naturally-occurring portions which function similarly.

Oligonucleotides designed according to the teachings of the present invention can be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988) and "Oligonucleotide Synthesis" Gait, M. J., ed. (1984) utilizing solid phase chemistry, e.g. cyanoethyl phosphorarnidite followed by deprotection, desalting and purification by for example, an automated trityl-on method or HPLC.

The oligonucleotides of the present invention may comprise heterocylic nucleosides consisting of purines and the pyrimidines bases, bonded in a 3' to 5' phosphodiester linkage.

Preferably used oligonucleotides are those modified in either backbone, internucleoside linkages or bases, as is broadly described hereinunder. Such modifications can oftentimes facilitate oligonucleotide uptake and resistivity to intracellular conditions.

Specific examples of preferred oligonucleotides useful according to this aspect of the present invention include oligonucleotides containing modified backbones or non-natural internucleoside linkages. Oligonucleotides having modified backbones include those that retain a phosphorus atom in the backbone, as disclosed in U.S. Pat. Nos. 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Preferred modified oligonucleotide backbones include, for example, phosphorothioates, chiral phosphorothioates, phosphorodithioates, phosphotriesters, aminoalkyl phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms can also be used.

Alternatively, modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts, as disclosed in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

Other oligonucleotides which can be used according to the present invention, are those modified in both sugar and the internucleoside linkage, i.e., the backbone, of the nucleotide units are replaced with novel groups. The base units are maintained for complementation with the appropriate polynucleotide target. An example for such an oligonucleotide mimetic, includes peptide nucleic acid (PNA). A PNA oligonucleotide refers to an oligonucleotide where the sugar-backbone is replaced with an amide containing backbone, in particular an aminoethylglycine backbone. The bases are retained and are bound directly or indirectly to aza nitrogen atoms of the amide portion of the backbone. United States patents that teach the preparation of PNA compounds include, but are not limited to, U.S. Pat. Nos. 5,539,082; 5,714,331; and 5,719,262, each of which is herein incorporated by reference. Other backbone modifications, which can be used in the present invention are disclosed in U.S. Pat. No. 6,303,374.

Oligonucleotides of the present invention may also include base modifications or substitutions. As used herein, "unmodified" or "natural" bases include the purine bases adenine (A) and guanine (G), and the pyrimidine bases thymine (T), cytosine (C) and uracil (U). Modified bases include but are not limited to other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further bases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Such bases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. [Sanghvi Y S et al. (1993) Antisense Research and Applications, CRC Press, Boca Raton 276-278] and are presently preferred base substitutions, even more particularly when combined with 2'-O-methoxyethyl sugar modifications.

Hybridization of short nucleic acids (below 200 bp in length, e.g. 17-40 bp in length) can be effected by the following hybridization protocols depending on the desired stringency; (i) hybridization solution of 6×SSC and 1% SDS or 3 M TMACl, 0.01 M sodium phosphate (pH 6.8), 1 mM EDTA (pH 7.6), 0.5% SDS, 100 μg/ml denatured salmon sperm DNA and 0.1% nonfat dried milk, hybridization temperature of 1-1.5° C. below the $T_m$, final wash solution of 3 M TMACl, 0.01 M sodium phosphate (pH 6.8), 1 mM EDTA (pH 7.6), 0.5% SDS at 1-1.5° C. below the $T_m$; (ii) hybridization solution of 6×SSC and 0.1% SDS or 3 M TMACl, 0.01 M sodium phosphate (pH 6.8), 1 mM EDTA (pH 7.6), 0.5% SDS, 100 μg/ml denatured salmon sperm DNA and 0.1% nonfat dried milk, hybridization temperature of 2-2.5° C. below the $T_m$, final wash solution of 3 M TMACl, 0.01 M sodium phosphate (pH 6.8), 1 mM EDTA (pH 7.6), 0.5% SDS at 1-1.5° C. below the $T_m$, final wash solution of 6×SSC, and final wash at 22° C.; (iii) hybridization solution of 6×SSC and 1% SDS or 3 M TMACl, 0.01 M sodium phosphate (pH 6.8), 1 mM EDTA (pH 7.6), 0.5% SDS, 100 μg/ml denatured salmon sperm DNA and 0.1% nonfat dried milk, hybridization temperature of 37° C., final wash solution of 6×SSC and final wash at 22° C.

Determination of hybridization complexes is well known in the art and may be achieved by any one of several approaches. These approaches are generally based on the detection of a label or marker, such as any radioactive, fluorescent, biological or enzymatic tags or labels of standard use in the art (i.e., detectable moiety). A label can be conjugated to either the oligonucleotide probes or the nucleic acids derived from the biological sample (target).

For example, oligonucleotides of the present invention can be labeled subsequent to synthesis, by incorporating biotinylated dNTPs or rNTP, or some similar means (e.g., photocross-linking a psoralen derivative of biotin to RNAs), followed by addition of labeled streptavidin (e.g., phycoerythrin-conjugated streptavidin) or the equivalent. Alternatively, when fluorescently-labeled oligonucleotide probes are used, fluorescein, lissamine, phycoerythrin, rhodamine (Perkin Elmer Cetus), Cy2, Cy3, Cy3.5, Cy5, Cy5.5, Cy7, FluorX (Amersham) and others [e.g., Kricka et al. (1992), Academic Press San Diego, Calif.] can be attached to the oligonucleotides.

It will be appreciated that a variety of controls may be usefully employed to improve accuracy of hybridization assays. For instance, samples may be hybridized to an irrelevant probe and treated with RNAse A prior to hybridization, to assess false hybridization.

Polymerase chain reaction (PCR)-based methods (e.g., RT-PCR) may also be used to identify SEL-OB. For PCR-based methods a pair of oligonucleotides is used, which is specifically hybridizable with the SEL-OB polynucleotide sequences described hereinabove in an opposite orientation so as to direct exponential amplification of a portion thereof (including the hereinabove described sequence alteration) in a nucleic acid amplification reaction. For example, an oligonucleotide pair of primers which can hybridize with SEL-OB is zset forth in SEQ ID NOs: 3 and 4 (see Example 1 of the Examples section).

The polymerase chain reaction and other nucleic acid amplification reactions are well known in the art and require no further description herein. The pair of oligonucleotides according to this aspect of the present invention are preferably selected to have compatible melting temperatures (Tm), e.g., melting temperatures which differ by less than that 7° C., preferably less than 5° C., more preferably less than 4° C., most preferably less than 3° C., ideally between 3° C. and 0° C.

Detection of SEL-OB can also be effected at the protein level. A number of protein detection methods are known in the art. Examples include, but are not limited to, electrophoretic methods which are preferably used to detect polypeptides mainly based on molecular weight variation and immunodetection assays such as ELISA and western blot analysis, immunohistochemistry, FACS (see Example 5 of the Examples section) and the like, which may be effected using antibodies specific to SEL-OB of the present invention.

Since SEL-OB expression varies a lot between different tissues and cells, SEL-OB can be used as a very important marker for the identification and isolation of cells of interest. As shown in FIGS. 11a-d SEL-OB is expressed at a detectable level on non-differentiated hematopoietic cells (CD34 positive cells and HL-60 cells), however its differentiation is markedly reduced or absent from differentiated cells (JURKAT and Raji cells). Hence the present invention envisages the use of SEL-OB detecting reagents for the detection of hematopoietic cells of a differentiation level of interest [at least partially un-differentiated or differentiated cells).

SEL-OB may also be used as a marker of bone and periosteum cells as well as of satellite cells, myoblasts and myocytes (see FIG. 16) which are present at the muscle tissue and contribute to muscle regeneration (see FIG. 2 and Example 7, respectively). SEL-OB may also be used as a marker for mesenchymal stem cells either alone or in combination with other markers directed thereto [e.g., Bone morphogenetic protein receptor (BMPR) and CD44].

Cell detection can be effected in vivo or in vitro (e.g., ex-vivo). Methods of isolating cell populations of interest are well known in the art. Thus, for example a hematopietic cell sample may be a peripheral blood cell sample or a bone marrow sample which has undergone none or at least some stages of cell enrichment. SEL-OB detecting reagents as well as of methods of using same are described in length above.

The use of double selection markers or more may be advantisiouly used for better characterization and/or enrichment of the cells of interest.

The present invention further envisages a method of modulating an interaction of a first cell (e.g., an osteoblast) with a second cell (e.g., hematopoietic cell) and/or a microenvironment, the method comprising regulating (i.e., upregulating or downregulating) a level and/or an activity of a SEL-OB polypeptide as described above, in the first cell, the second cell, and/or the microenvironment, thereby modulating the interaction of the first cell with the second cell and/or the microenvironment.

As used herein the term "microenvironment" refers to the surrounding of a cell, such as a bone marrow, a periosteum and a tumor.

Methods of upregulating or downregulating expression or activity of SEL-OB polypeptides are described in details hereinabove.

Thus, the present invention provides novel polynucleotides and polypeptide sequences which can be used for the diagnosis, treatment or prevention of skeletal disorders, cancer and inflammatory diseases.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

SEL-OB mRNA Expression Analysis in Skeletal Cells by RT-PCR

To determine whether and which cells in humans, mice, and rats express SEL-OB, the gene was isolated and cloned, and cultured marrow stromal cells, microdissected tissues from mice, and bone marrow cells from rats were analyzed for expression using PCR and X-ChIP.

Materials and Experimental Procedures

Gene Isolation, Cloning, and Sequencing:

The sequence of the full-length SEL-OB cDNA was predicted from the sequence of RNA extracted from human marrow stromal cells (hMSCs) using analysis software available from NCBI to analyze the genomic region. Table 4, below, lists the bioinformatics analyses used for all of the examples and the websites at which they can be found, and should be referred to throughout all of the examples. BlastN alignment against human NR (non-redundant sequences) and EST (expressed sequence tag) databases was used to create virtual cDNA. Primer3 software and the predicted sequence were then used to design primers for cDNA cloning.

The SEL-OB gene was cloned from RNA extracted from hMSCs, amplified with primers F-GGATTGTGTCTGTC-CCCAGT and R-GGCACTACCGAGGAGAGATG (SEQ ID NOs: 1 and 2, respectively) using Platinum® Taq DNA Polymerase (Invitrogen, USA). The amplified cDNA was purified (DNA IQ™, Promega, USA) and sequenced with gene-specific primers at the Sequencing Unit of Tel Aviv University (Applied Biosystems Sequencing Unit, Department of Life Sciences, Tel Aviv University).

Culturing of Mouse, Rat, and Human MSCs:

Primary cultured marrow stromal cells (MSCs) of mouse, rat, and human origin were used. Human bone marrow stromal cells (MSC) were collected from surgical aspirates of bone marrow from normal donors to prepare ex vivo culture plated at low-density ($1.5 \times 10^4$ cells/$cm^2$). Cells were cultured in Dulbecco's Modified Essential Medium (DMEM) with the addition of 10% heat-inactivated fetal calf serum (FCS). Rat and mouse MSCs were retrieved from the bone marrow plug flashed from femurs and adjusted to $10^6$ cells/ml.

All the experiments were performed using cells from the first passage (Shur et al., 2001), the mouse stromal cell line MBA-15 (described in Benayahu et al., 1989), and the mouse myoblast line C2C12 (ATCC Accession No. CRL 1772) were cultured in the growth medium Dulbecco's Modified Essential Medium (DMEM), supplemented with 10% heat-inactivated fetal calf serum (FCS), 1% glutamine, and 1% antibiotics, and maintained in 10% $CO_2$ at 37° C.

Laser Capture Microdissection (LCM) of Skeletal Tissue Preparations:

Newborn mice were frozen in liquid nitrogen and embedded in Tissue-Tek OCT (optimal cutting temperature) embedding medium (Ames, USA). 5 µm-thick tissue sections were cut at −20° C. using a cryostat (Microtome Cryostat, Jung Frigocut 2800 N, Reichert Jung/Leica). Sections were placed onto glass slides, fixed in 70% ethanol for 30 seconds, dehydrated in an increasing series of ethanol, and cleared in xylene. Air-dried sections were microdissected with PALM® MicroLaser System laser capture microscope (PALM Microlaser Technologies AG, Germany).

Differential Gene Expression Analysis by RT-PCR with Species-Specific Primers:

Differential gene expression analysis was performed using RNA reverse-transcribed to cDNA from: (A) cultured Homo sapiens (human), Mus musculus (mouse), and Rattus norvegicus (rat) MSCs; (B) newborn mouse skeletal tissues collected by LCM; and (C) bone marrow cells extracted from 6- and 14-month-old sham and OVX female rats, as described above.

RNA was extracted using the EZ-RNA isolation kit (Biological Industries, Beth Haemek, Israel), and reverse-transcribed to cDNA using avian myeloblastosis virus reverse transcriptase (AMV-RT) (Takara Shuzo Co., Ltd., Japan) and oligo-dT. RNA was isolated and reverse-transcribed from LCM samples using the RNeasy® Kit and Sensiscript® RT Kit (Qiagen, Germany).

Gene expression analysis applied SEL-OB-specific primers (Table 5, below). The integrity of the RNA, the efficiency of the reverse-transcription (RT) reaction, and the quality of cDNA subjected to the RT-PCR amplification were normalized by the level of the house-keeping gene Glyceraldehyde-3-Phosphate Dehydrogenase [G3PDH, GenBank Accession No. NM_002046 (Clontech, Palo Alto, Calif.)].

TABLE 4

Websites and software used for bioinformatics analyses

| URL | Analysis Performed |
| --- | --- |
| http://worldwidewebdotncbidotnlmdotnihdotgov | NCBI (BLAST, CD-search, UniGene, OMIM, LocusLink) |
| http://bioinformaticsdotweizmanndotacdotil/cgi-bin/primer/primer3dotcgi/results_from_primer3 | Primer3 software: PCR primer design |
| http://worldwidewebdotsoftberrydotcom/berrydotphtml?topic=promoter | Promoter prediction and characterization |
| worldwidewebdotexpasydotorg/tools/dnadothtml | Translate: DNA/RNA-Protein Translation, Open reading frame (ORF) prediction |
| worldwidewebdotexpasydotorg/tools/protparamdothtml | Protein parameters |
| http://smartdotembl-heidelbergdotde/ | SMART (Simple Modular Architecture Research Tool): functional and structural domains |
| http://proteindottoulousedotinradotfr/multalin/ | Multalin: hierarchical clustering and multiple-sequence alignment |

TABLE 5

Specific primers used for SEL-OB mRNA expression analysis

| PrimeR name | Forward oriented | Reverse oriented | Product Expected Size |
|---|---|---|---|
| SEL-OB Human | TTCTCTTACACGGAGCTACACTAT (SEQ ID NO: 3) | TGGGATGGAACTTGACCAT (SEQ ID NO: 4) | 295 bp |
| SEL-OB Mouse | AAACCAATGTGCAAACCCAT (SEQ ID NO: 5) | GGATCCATATCCCAGTCACC (SEQ ID NO: 6) | 180 bp |
| SEL-OB Rat | TCTCTTCCGTGAGCTTTCAG (SEQ ID NO: 7) | GCTGGAGCTTGACCACCC (SEQ ID NO: 8) | 300 bp |
| G3PDH | ACCACAGTCCATGCCATCAC (SEQ ID NO: 9) | TCCACCACCCTGTTGCTGTA (SEQ ID NO: 10) | 450 bp |

Semi-Quantitative Analysis of Amplified RT-PCR Products:

Semi-quantitative PCR was performed with SP6 RNA polymerase (Fermentas, USA), and PCR products were separated by electrophoresis in 1% agarose gels (SeaKem® GTG®, BioWhittaker Molecular Applications (BMA), Maine, USA) in Tris Borate EDTA (TBE) buffer. The amplified DNA fragments were stained by ethidium bromide, and their optical density was measured using the BIS 202D (Bio Imaging System, Pharmacia Biotech, Japan and FujiFilm, Japan), and analyzed using TINA software (Raytest, Strauhenhardt, Germany). PCR amplification was performed at least twice and subjected to semi-quantitative analysis by comparison of the OD of the SEL-OB PCR products normalized to the OD of co-amplified G3PDH PCR products. Real-time PCR was performed with LightCycler® FastStart DNA Master SYBR® Green kit (Roche Applied Science, Roche Diagnostics, USA) according to the manufacturer's standard protocols. The specificity of the amplification reaction was confirmed by melting curve analysis (results not shown).

Results

Cloning—The SEL-OB gene was cloned from human marrow stromal cells as described in the Material and Experimental Procedures section above. The cDNA comprise 11139 bp (SEQ ID NO: 17, GenBank Accession No. AY243503, see FIG. 1a). BLAST analysis of the nucleotide sequence showed that it is homologous to the polydom genes. The overall identity between the mouse, rat and human genes was above 80% (FIG. 1b). Sequence of SEL-OB and exon structure is described in FIGS. 13a-b and in Table 6 below.

TABLE 6

| Exon | Start | End | Length (nt) |
|---|---|---|---|
| 1 | 1 | 694 | 693 |
| 2 | 694 | 950 | 256 |
| 3 | 951 | 1127 | 176 |
| 4 | 1128 | 1286 | 158 |
| 5 | 1287 | 1466 | 179 |
| 6 | 1467 | 1646 | 179 |
| 7 | 1647 | 1844 | 197 |
| 8 | 1845 | 1965 | 120 |
| 9 | 1966 | 2093 | 127 |
| 10 | 2094 | 2202 | 108 |
| 11 | 2203 | 2335 | 132 |
| 12 | 2336 | 2528 | 192 |
| 13 | 2529 | 2652 | 123 |
| 14 | 2653 | 2763 | 110 |
| 15 | 2764 | 2927 | 163 |
| 16 | 2928 | 3161 | 233 |
| 17 | 3162 | 3323 | 161 |
| 18 | 3324 | 3485 | 161 |

TABLE 6-continued

| Exon | Start | End | Length (nt) |
|---|---|---|---|
| 19 | 3486 | 3649 | 163 |
| 20 | 3650 | 3740 | 90 |
| 21 | 3741 | 3837 | 96 |
| 22 | 3838 | 3952 | 114 |
| 23 | 3953 | 4065 | 112 |
| 24 | 4066 | 4266 | 200 |
| 25 | 4267 | 4424 | 157 |
| 26 | 4425 | 4626 | 201 |
| 27 | 4627 | 4810 | 183 |
| 28 | 4811 | 4938 | 127 |
| 29 | 4939 | 5060 | 121 |
| 30 | 5061 | 5232 | 171 |
| 31 | 5233 | 5405 | 172 |
| 32 | 5406 | 5525 | 119 |
| 33 | 5526 | 5702 | 176 |
| 34 | 5703 | 5789 | 86 |
| 35 | 5790 | 5979 | 189 |
| 36 | 5980 | 6147 | 167 |
| 37 | 6148 | 6820 | 672 |
| 38 | 6821 | 9612 | 2791 |
| 39 | 9613 | 9838 | 225 |
| 40 | 9839 | 9995 | 156 |
| 41 | 9996 | 10058 | 62 |
| 42 | 10059 | 10232 | 173 |
| 43 | 10233 | 10409 | 176 |
| 44 | 10410 | 10580 | 170 |
| 45 | 10581 | 10676 | 95 |
| 46 | 10677 | 10772 | 95 |
| 47 | 10773 | 10867 | 94 |
| 48 | 10868 | 11137 | 269 |

Mouse, rat, and human marrow stromal cells express SEL-OB mRNA—Multiple alignment of partial cDNAs was then used to create human-, mouse-, and rat-specific PCR primers (Table 4 above) for analysis of SEL-OB mRNA expression in primary cultured MSCs and skeletal tissues. In vitro SEL-OB expression in MSCs was detected in all three species by RT-PCR (FIG. 1c).

SEL-OB is expressed in mouse skeletal tissues—In vivo SEL-OB expression in the skeletal system was analyzed in newborn mouse tissues. Periosteum, bone, cartilage, and skeletal muscle were retrieved from frozen sections, schematically illustrated in FIG. 2a using the LCM technique. SEL-OB expression was detected by PCR amplification in bone and periosteum, but not in cartilage and skeletal muscle (FIG. 2b).

Example 2

The Promoter Region of SEL-OB Contains Three ERE Half-Sites and an AP-1 Element Bioinformatic analysis was applied to predict the promoter sequence in the 5'-flanking region of the human SEL-OB gene.

Bioinformatics analyses—Bioinformatics analyses at the DNA level included genomic analysis, analysis of the translation initiation site, and promoter prediction and characterization (see Table 3, above). A 3000-bp genomic region upstream of the 5'-flanking sequence of the SEL-OB translation start site was used for promoter prediction. The identified region was further analyzed for possible transcription factor binding sites and used to create promoter-specific primers for X-ChIP analysis (see Example 2, below).

Results

The region contains several spaced, consensus half-palindromic estrogen response elements (EREs) [at −1121-(−1117) bp, −1082-(−1078) bp, and −1036-(−1032) bp] and an AP-1 binding site at −862 bp-(−856) (see FIGS. 14a-14b). Both elements (ERE and AP-1) were identified on promoters of estrogen-responsive genes, and they mediate two pathways involved in estrogen transcription regulation (Jakacka et al., 2001). The classical estrogen signaling pathway is based on direct estrogen receptor (ER) binding to DNA at an ERE, and the non-classical pathway involves a protein-protein interaction between ER and pcJun, the transcription factor that binds to the AP-1 site of the promoter region.

Example 3

Expression of SEL-OB is Regulated by Estrogen

It is well established that estrogen affects skeletal metabolism [reviewed in Manolagos et. al., (2002) Recent Prog. Horm. Res. 57:385-409]. X-ChIP and PCR techniques were used to determine whether SEL-OB expression in osteoblasts is regulated by estrogen. Additionally, estrogen regulation of SEL-OB expression in bone skeletal cells was analyzed in a rat model of ovariectomized (OVX) animals and animals subjected to a sham ovariectomy (sham), previously described for their changes in skeletal structure (Ke et al., 1993).

Materials and Experimental Procedures

Isolation of bone marrow cells from ovariectomized and sham-operated rats—Young rats (6- and 14 months-old) were subjected to a sham-ovariectomy operation (sham) or were ovariectomized (OVX). Bone marrow cells were collected from both sham and OVX rats of both ages 3 months following the operations.

SEL-OB expression modulation experiments—For modulation of SEL-OB mRNA expression, primary cultured hMSCs were cultured in 3% serum-stripped medium for 48 hours prior to their treatment with either $10^{-8}$ M 17 β-estradiol, the most potent and abundant estrogenic hormone in mammals, or $10^{-6}$ M estrogen inhibitor 182,780 (ICI 182, 780) (Zeneca Pharmaceuticals), a selective inhibitor of the intracellular estrogen receptors.

Chromatin immunoprecipitation (X-ChIP)—The technique of cross-linked chromatin immunoprecipation (X-ChIP) is based on formaldehyde fixation of DNA-protein complexes followed by isolation of the chromatin fraction (Chromatin Immunoprecipitation (ChIP) Assay Kit, Upstate Biotech, USA). X-ChIP was performed using monoclonal antibodies to the estrogen receptor (anti-ER) (Upstate, USA) and to phosphorylated cJUN (anti-pcJUN) (Santa Cruz Biotechnology, Santa Cruz, Calif., USA). pcJun is a transcription factor that binds to some promoter sequences, including that of SEL-OB (as predicted) at the AP-1 site. DNA isolated from immunoprecipitated DNA-protein complexes was amplified by PCR with primers specific to SEL-OB promoter (F-ATTACTGTGGCACTCTCGGT (SEQ ID NO: 11) and R-ATTCCATGACACCAGAACCC (SEQ ID NO: 12). The amount of amplified, immunoprecipitated DNA was normalized to the amount of amplified DNA in the corresponding input chromatin fraction. Each PCR reaction was performed at least twice.

RT-PCR—see Example 1 above.

Results

Sham and OVX rats of 6 and 14 months of age were compared for SEL-OB expression in bone marrow. Expression was detected by RT-PCR in sham, but not OVX rats of both age groups (FIG. 3a).

In addition, cultured osteoblasts were treated with 17 β-estradiol to analyze its effect on the expression of SEL-OB mRNA. The cells were challenged for 15 minutes to 48 hours and analyzed at each time point for the mRNA level of expression by real-time kinetic PCR. A 2.2-fold increase was shown in the SEL-OB message after a 60 minute treatment with 17 beta-estradiol, as compared with control levels; extended treatment revealed a decline in SEL-OB expression to control levels after 48 hours. At each time, the level of SEL-OB expression was normalized to the expression of G3PDH (FIG. 3b). These results indicate that SEL-OB expression is induced by estrogen in vitro, confirming the results of in vivo estrogen experiments, above.

X-ChIP analysis was performed with antibodies to ER and pcJun to study the binding of estrogen receptor (ER), directly and indirectly, to the SEL-OB promoter in MSCs. SEL-OB promoter DNA was isolated from immunoprecipitated complexes and PCR-amplified, demonstrating the interaction of the ER and pcJun with the analyzed promoter region (FIG. 4, lanes 1-4). The binding of pcJun at the SEL-OB AP-1 site was analyzed also in the presence of either 17 β-estradiol or ICI 182,780 (estrogen inhibitor), revealing pcJun binding in control and estrogen-treated cells; however, the interaction was abolished in the presence of estrogen inhibitor (FIG. 4, lanes 2-4).

The results presented in Examples 1-3 indicate that the expression of human SEL-OB is regulated by estrogen and is confined to skeletal cells.

Example 4

Structural and Expression Analysis of SEL-OB Protein

The 3574-amino acid (aa) SEL-OB polypeptide sequence (SEQ ID NO: 15) was used to create anti-SEL-OB antibody.

Materials and Experimental Procedures

SEL-OB protein sequence by bioinformatics—The SEL-OB polypeptide sequence (SEQ ID NO: 15) was predicted from the full-length cDNA sequence using the Translate tool from ExPASy (see Table 3).

Antibody production—Based on the SEL-OB protein sequence, a 17-aa peptide [DVDAPSCNAIHCDSPQP (SEQ ID NO: 13)] was synthesized by the thioester method, conjugated to Keyhole limpet Hemocyanin (KLH), and injected into rabbits for immunization. Subsequent boosts and bleeds were finalized at a final bleed serum purified for IgG on a G affinity column (Pharmacia/LKB Corp., Piscataway, N.J., USA).

Cell lysate preparation—Human MSC lysate was produced by the following lysis procedure: Cells were harvested from cultures, washed twice with ice-cold PBS and collected in presence of protease inhibitors (Phenylmethylsulfonyl fluoride PMSF, 1 mM; 1-Chloro-3-tosylamido-4-phenyl-2-butanone, TPCK, 10 g/ml; Aprotinin, 10 g/ml (Sigma, USA) and phosphatase inhibitors cocktails I and II (Sigma, USA). Samples were spin down at 1500 rpm for 4 min, lyses buffer consisting of 50 mM Tris pH 7.5, 150 mM NaCl, 1% NP-40, protease and phosphatase inhibitors was added, incubation for 20 min at 4° C. and samples were centrifuged at 16,000 g for 5 min. Lysates were then subjected to immunoprecipitation as further described hereinbelow.

Immunoprecipitation, SDS-PAGE, and Western blot—anti-SEL-OB antibodies (described above) were incubated with Sepharose CL-4B-conjugated Protein A (Pfizer-Pharmacia Diagnostics, USA). The immobilized antibodies were then added to the above described hMSC lysates. Immunocomplexes were allowed to form for overnight at 4° C. while shaking. The precipitated immuno-protein complex was then subjected to 6.5% SDS-PAGE for 2 hours, resolving the SEL-OB protein in the gel. Proteins were then electro-transferred for 30 minutes to a nitrocellulose membrane. The membrane was then blotted with anti-SEL-OB in PBS with 0.05% Tween-20 for 1 hour, followed by wash steps with PBS-Tween-20, then briefly incubated with the secondary antibody goat anti-rabbit biotin IgG (Dako Corporation, Denmark) and ExtrAvidin®-peroxidase (Sigma-Aldrich Co., USA) in PBS-Tween 20 for detection of the chemiluminescent substrate (Pierce Biotech, USA), exposed to X-OMAT AR film (Kodak, USA), and developed.

Immunohistochemistry—$1\times10^4$ cells were plated on cover slips, and after 48 hours were fixed in 0.4% formalin in phosphate buffered saline (PBS). Immune detection was effected using anti-SEL-OB purified antibodies. The signal was amplified with a secondary antibody, goat anti-rabbit-biotin-conjugated IgG (Dako), visualized with ExtrAvidin®-peroxidase, and detected with: for light microscopy (400× and 630×) (Zeiss, Germany), the chromagen 3-3'-Diaminobenzidine tetrahydrochloride (DAB) (Sigma), which creates a hard dissolving salt sedimentation after reacting with the peroxidase; and for LSM 410 confocal microscopy (630×) (Zeiss), ExtrAvidin®-FITC (Sigma).

Fluorescence-activated cell sorter (FACS)—Cell surface expression of SEL-OB on cultured MBA-15 cells was analyzed by FACS as described in technical protocols available from BD Biosciences-Pharmingen (see http://worldwidewebdotbdbiosciencesdotcom/protocols/pharmingen). Briefly, cells were first released using 0.5 mM EDTA in PBS, and single-cell suspensions ($10^6$ cells per sample) were resuspended in PBS containing 1% FCS (blocking buffer). Cells were incubated for 30 minutes on ice with primary antibody against SEL-OB and stained with goat anti-rabbit-biotin-conjugated IgG and ExtrAvidin®-FITC. Labeled cells ($10^4$ per sample) were collected by FACS, and statistical analysis was performed using CellQuest™ software (BD Biosciences, Becton, Dickinson and Company).

Bioinformatics analyses—see Example 2 and Table 3, above.

Results

SEL-OB Protein Shows a Novel Domain Structure:

SEL-OB cDNA encodes a 3574-aa protein with a predicted molecular weight of approximately 370 kDa. Bioinformatics analysis of SEL-OB protein revealed multiple domains, schematically illustrated in FIG. 5a and in Table 7 below. The domain structure of SEL-OB is similar to that of mouse Polydom protein. However, mouse polydom lacks the RGD attachment aite and has 36 CCP domains while SEL-OB has 34 CCP domains.

SEL-OB contains a von Willebrand factor type A (vWFA) domain, 2 Hyalin Repeat (HYR) domains probably involved in cell adhesion, a tumor necrosis factor receptor (TNFR) Cysteine-rich domain, a pentraxin (PTX) domain, an RGD cell attachment site, 2 epidermal growth factor (EGF) domains, 7 EGF-like $Ca^{2+}$-binding domains, and 34 complement control protein (CCP) repeats.

TABLE 7

SMART analysis of SEL-OB functional domains

| Name | Begin on SEQ ID NO: 15 | End on SEQ ID NO: 15 |
| --- | --- | --- |
| VWA | 81 | 260 |
| CCP | 378 | 433 |
| CCP | 438 | 493 |
| CCP | 498 | 559 |
| CCP | 727 | 787 |
| EGF_CA | 1196 | 1229 |
| EGF_CA | 1231 | 1267 |
| EGF_CA | 1269 | 1305 |
| EGF_CA | 1307 | 1343 |
| EGF_CA | 1345 | 1381 |
| EGF_CA | 1383 | 1419 |
| PTX | 1420 | 1630 |
| CCP | 1634 | 1688 |
| CCP | 1693 | 1746 |
| EGF_CA | 1748 | 1787 |
| CCP | 1792 | 1845 |
| CCP | 1850 | 1903 |
| CCP | 1908 | 1961 |
| CCP | 1966 | 2019 |
| CCP | 2024 | 2081 |
| CCP | 2086 | 2144 |
| CCP | 2149 | 2202 |
| CCP | 2207 | 2262 |
| CCP | 2267 | 2321 |
| CCP | 2326 | 2379 |
| CCP | 2384 | 2438 |
| CCP | 2443 | 2496 |
| CCP | 2501 | 2554 |
| CCP | 2559 | 2611 |
| CCP | 2657 | 2715 |
| CCP | 2720 | 2773 |
| CCP | 2778 | 2831 |
| CCP | 2836 | 2889 |
| CCP | 2894 | 2947 |
| CCP | 2952 | 3005 |
| CCP | 3010 | 3062 |
| CCP | 3067 | 3120 |
| CCP | 3125 | 3179 |
| CCP | 3184 | 3239 |
| CCP | 3244 | 3297 |
| CCP | 3302 | 3355 |
| CCP | 3360 | 3414 |
| CCP | 3419 | 3471 |
| EGF | 3474 | 3503 |
| EGF CA | 3507 | 3535 |
| ZnF NFX | 3523 | 3545 |
| EGF | 3538 | 3567 |

The presence of the EGF and CCP domains makes SEL-OB similar to the selectin cell adhesion proteins; however, SEL-OB does not include a lectin domain, suggesting that SEL-OB belongs to a discrete group of membrane proteins.

Cell Staining Shows that SEL-OB is Heterogeneously Expressed in the Cell Membrane and Cytoplasm of Mouse and Human Marrow Cells:

Anti SEL-OB antibody was used to study the protein and to sub-cellularly analyze expression thereof. Immunoprecipitation and Western blot identified a high-molecular-weight protein (~370 kDa) from the cell lysates (FIG. 6). Immunohistochemistry analysis (IMH) of SEL-OB expression by mMSCs, hMSCs, and mouse MBA-15 cells localized the protein to the cell membrane and cytoplasm, as demonstrated by confocal microscopy (FIGS. 7a-c) and light microscopy (FIGS. 7d-e). Cells expressing SEL-OB demonstrated a heterogeneous pattern of protein staining, with a small population that were strongly stained and most cells expressing SEL-OB at lower levels (FIG. 7d). Notably, populations of cells of small dimensions are correlated with higher proliferative capacity indicating the use of SEL-OB as a marker of proliferative cell populations.

FACS Analysis Confirms Heterogeneous Expression of SEL-OB in hMSCs and Mouse MBA-15 Cells:

FACS analysis was used to quantify the SEL-OB expression identified by IMH. Two sub-populations of cells were classified; most cells expressed low levels of the surface protein and a smaller population expressed a higher level of SEL-OB (FIG. 8a), which is consistent with the results of the IMH staining. SEL-OB expression in hMSCs and MBA-15 cells was 31%±2.1 and 26%±4.9, respectively (FIG. 8b). The FACS analysis also identified a correlation between SEL-OB expression and cell size: 85% of SEL-OB-positive cells were small cells (FIG. 8b).

Example 5

SEL-OB is a Cell Adhesion Protein, with Adhesion Activity Reduced upon Addition of Anti-SEL-OB Materials and Experimental Procedures
Antibody Blockade of SEL-OB Adhesion Properties:
Single-cell suspensions were incubated with either anti-SEL-OB or IgG-rabbit (control) and plated in DMEM supplemented with 3% charcoal-stripped serum. After 15 minutes, the unbound cells were collected in fractions, and the bound cells were released with 0.5 mM EDTA in PBS and collected. Both unbound and bound cell fractions were counted by hemocytometer, stained with FITC-labeled goat anti-rabbit antibody, and subjected to the FACS analysis described above.

Results

The role of SEL-OB in adhesion processes was studied using released and resuspended MBA-15 cells, followed by their treatment with SEL-OB antibody, re-plating for 15 minutes, and FACS. Quantitative analysis of SEL-OB expression in these cells revealed that there were 50% more unbound cells in the anti-SEL-OB-treated fraction than in those incubated with nonspecific IgG (results not shown). These results suggest that SEL-OB antibody delays the time of initial cell attachment, as compared with the control. FIGS. 9a-b summarizes FACS analyses of SEL-OB expression in the bound and unbound cells and shows 3.4-fold more SEL-OB-positive cells in unbound versus bound cell populations. Interference of anti-SEL-OB with cell adhesion was thus demonstrated, indicating the role of SEL-OB protein in the process of cell adhesion.

Example 6

SEL-OB Expression Analysis in Human Carcinoma and Hematopoietic Cell Lines

To determine whether human carcinoma and hematopoietic cells express SEL-OB in vitro, RT-PCR and FACS analyses were performed on various cell lines.

Materials and Experimental Procedures
Culturing of Human Cell Lines:
Culturing of human cell lines was as described in Example 1 for mouse, rat, and human MSCs. The carcinoma and hematopoietic cell lines used included: MCF7 breast adenocarcinoma (ATCC Accession No. HTB-22); MDA-231 breast adenocarcinoma (ATCC Accession No. HTB-26); T-47D breast carcinoma (ATCC Accession No. HTB-133); MDA-435 breast carcinoma (ATCC Accession No. HTB-129); HCC1937 breast carcinoma (ATCC Accession No. CRL-2327); expanded human CD34+hematopoietic stem/progenitor cells [Obtained from cord blood of full-term normal deliveries. The mononuclear cell fraction was separated by Ficoll gradient (Ficoll-PaqueÔ, Amersham Pharmacia Biotech AB) by density centrifugation. CD34+ cells were isolated using Dynal® CD34 Progenitor Cell Selection System according to manufacturer instructions]; HL-60 myeloid leukemia cells (ATCC Accession No. CCL-240); Raji B cell lymphoma (B lymphocyte, Burkitt's lymphoma, ATCC Accession No. CCL-86); and Jurkat T cells (T lymphocyte, acute T cell leukemia, ATCC Accession No. CCL-243).

Differential Gene Expression Analysis by RT-PCR:
Gene expression analysis was performed as described in Example 1 with MCF7, MDA-231, MDA-435, and T-47D cell lines.

Immunohistochemistry:
Immunohistochemical analysis with anti-SEL-OB (produced as described in Example 4 above) was performed as described in Example 4 on MDA-231, MCF7, and T-47D cell lines, and visualized by confocal microscopy (630×) only.

Fluorescence-Activated Cell-Sorter (FACS):
FACS analysis was performed as described in Example 4 with CD34+, HL-60, Raji, Jurkat, MCF7, T-47D, HCC1937, MDA-231, and MDA-435 cell lines.

Results

FIG. 10a shows mRNA expression of SEL-OB in the MCF7, MDA-231, MDA-435, and T-47D cells lines as determined by RT-PCT (FIG. 10a, lanes 1-4, respectively).

SEL-OB is Expressed in Carcinoma and Hematopoietic Cells, as Determined by FACS and IMH Analyses:

SEL-OB protein was also shown to be expressed in MDA-231, MCF7, and T-47D (FIGS. 10b-d, respectively) by immunohistochemical analysis. FACS analysis shows expression of SEL-OB in the CD34+, HL-60, Raji B lymphoma, and Jurkat T cell leukemia cell lines (FIGS. 11a-d, respectively); and in MCF7, T-47D, HCC1937, MDA-231, and MDA-435 cell lines (FIG. 12b, lanes 1-5, respectively). In summary, SEL-OB is both a marker and an immunogenic target for certain carcinoma and hematopoietic cell types (i.e., identifies non-differentiated hematopoietic cell populations).

Example 7

Muscle Derived Stem Cells Express SEL-OB

Isolated fibers from Skeletal muscle were immunofluorescently (IF) stained. Dapi staining was perform to label all cell nuclei in the fiber. The positive IF cells are satellite cells (SC) in accordance with the positive staining with Pax7.

Example 8

Anti SEL-OB Antibody Inhibits Cell Homing

Human hematopoietic cell migration and homing relies on a wide variety of cell adhesion molecules (CAMs), including cadherins, integrins and selectins that target the homing cells towards a specific location within the hematopoietic compartment; in the spleen or bone marrow.

NOD/ltSz-scid mice were used to substantiate the role of SEL-OB in the homing process in vivo.

5×10⁶ G2 cells Human Pre-B acute lymphoblastic leukemia cells (G2 Kamel-Reid S, Letarte M, Sirard C, Doedens M, Grunberger T, Fulop G, Freedman M H, Phillips R A, Dick J E A model of human acute lymphoblastic leukemia in immune-deficient SCID mice. Science 246:1597, 1989) expressing high level of SEL-OB were tail injected into NOD/ltSz-scid mice (n=3). These mice have multiple defects in intrinsic immunity which render them excellent recipients for human hematopietic cells.

To distinguish the human cells within the mice, mouse-anti-human-CD45R antibody was used (IQP-124R, IQ Products). As shown in FIG. 15, more than 95% of cells were positively stained as analyzed by FACS.

To test whether SEL-OB plays a role in cell homing, human G2 cells were incubated with the anti SEL-OB antibody described above or with unspecific rabbit IgG (control) for 30 minutes followed by an i.v injection to the tail vein of NOD/ltSz-scid mice. Sixteen hours following injection cells were isolated from spleen of recipient mice and analyzed by FACS for the presence of human cells using mouse anti-human CD45R Phycoerythrin (PE) labelled.

The percent of G2 positively stained cells in the tested spleen of recipient mice were 9.7% and 5.3% for cells treated with anti-SEL-OB antibody and 13.7% in the control IgG injected mouse. This experiment resulted in the overall reduction of homing of G2 cells treated with anti-SEL-OB antibody by 30% (A) and 60% (B) as compared to the control (C, Table 10).

TABLE 10

|  | Pre-incubation with an antibody | % of G2 positively stained cells | % of inhibition |
|---|---|---|---|
| Mouse A | Anti SEL-OB | 9.7 | 30 |
| Mouse B | Anti SEL-OB | 5.3 | 60 |
| Mouse C | Rabbit IgG | 13.7 |  |

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

REFERENCES CITED

Additional References are Cited in the Text

Ansell, S. M., Tardi, P. G., and Buchkowsky, S. S. (1996). 3-(2-pyridyldithio)-propionic acid hydrazide as a cross-linker in the formation of liposome-antibody conjugates. Bioconjug Chem 7(4), 490-496.

Arai, S., Amizuka, N., Azuma, Y., Takeshita, S., and Kudo, A. (2003). Osteoclastogenesis-related antigen, a novel molecule on mouse stromal cells, regulates osteoclastogenesis. J Bone Miner Res 18(4), 686-695.

Askenasy, N., Zorina, T., Farkas, D. L., and Shalit, I. (2002). Transplanted hematopoietic cells seed in clusters in recipient bone marrow in vivo. Stem Cells 20, 301-310.

Aziz, K. E. and Wakefield, D. (1996). Modulation of endothelial cell expression of ICAM-1, E-selectin, and VCAM-1 by beta-estradiol, progesterone, and dexamethasone. Cell Immunol 167, 79-85.

Benayahu, D. (1997). Estrogen effects on protein expressed by marrow stromal osteoblasts. Biochem Biophys Res Commun 233(1), 30-35.

Benayahu, D., Efrati, M., and Wientroub, S. (1995). Monoclonal antibodies recognize antigen expressed by osteoblasts. J Bone Miner Res 10(10), 1496-1503.

Benayahu, D., Kletter, Y., Zipori, D., and Wientroub, S. (1989). Bone marrow-derived stromal cell line expressing osteoblastic phenotype in vitro and osteogenic capacity in vivo. J Cell Physiol 140, 1-7.

Benayahu, D., Shur, I., and Ben-Eliyahu, S. (2000). Hormonal changes affect the bone and bone marrow cells in a rat model. J Cell Biochem 79, 407-415.

Bork, P., Downing, A. K., Kieffer, B., and Campbell, I. D. (1996). Structure and distribution of modules in extracellular proteins. Q Rev Biophys 29, 119-167.

Brigstock, D. R. (2003). The CCN family: a new stimulus package. J Endocrinol 178(2), 169-175.

Bush, T. L. and Whiteman, M. K. (1999). Hormone replacement therapy and risk of breast cancer. JAMA 281(22), 2140-2141.

Callebaut, I., Gilgès, D., Vigon, I., and Momon, J. P. (2000). HYR, an extracellular module involved in cellular adhesion and related to the immunoglobulin-like fold. Protein Sci 9(7), 1382-1390.

Calvi, L. M., Adams, G. B., Weibrecht, K. W., Weber, J. M., Olson, D. P., Knight, M. C., Martin, R. P., Schipani, E., Divieti, P., Bringhurst, F. R., Milner, L. A., Kronenberg, H. M., and Scadden, D. T. (2003). Osteoblastic cells regulate the haematopoietic stem cell niche. Nature 425, 841-846.

Caulin-Glaser, T., Watson, C. A., Pardi, R., and Bender, J. R. (1996). Effects of 17beta-estradiol on cytokine-induced endothelial cell adhesion molecule expression. J Clin Invest 98, 36-42.

Cenci, S., Toraldo, G., Weitzmann, M. N., Roggia, C., Gao, Y., Qian, W. P., Sierra, O., and Pacifici, R. (2003). Estrogen deficiency induces bone loss by increasing T cell proliferation and lifespan through IFN-gamma-induced class II transactivator. Proc Natl Acad Sci USA 100, 10405-10410.

Cid, M. C., Kleinman, H. K., Grant, D. S., Schnaper, H. W., Fauci, A. S., and Hoffman, G. S. (1994). Estradiol enhances leukocyte binding to tumor necrosis factor (TNF)-stimulated endothelial cells via an increase in TNF-induced adhesion molecules E-selectin, intercellular adhesion molecule type 1, vascular cell adhesion molecule type. J Clin Invest 93, 17-25.

Colombatti, A., Bonaldo, P., and Doliana, R. (1993). Type A modules: interacting domains found in several non-fibrillar collagens and in other extracellular matrix proteins. Matrix 13, 297-306.

Dai-Do, D., Espinosa, E., Liu, G., Rabelink, T. J., Julmy, F., Yang, Z., Mahler, F., and Luscher, T. F. (1996). 17 beta-estradiol inhibits proliferation and migration of human vascular smooth muscle cells: similar effects in cells from postmenopausal females and in males. Cardiovasc Res 32(5), 980-985.

Davis, C. G. (1990). The many faces of epidermal growth factor repeats. New Biol 2, 410-419.

DeGroot, H., III (2004). www.bonetumor.org: "Metastatic Tumors in Bone." http://www.bonetumor.org/tumors/pages/page60.html, visited December 2004.

Duong, L. T. and Rodan, G. A. (1998). Integrin-mediated signaling in the regulation of osteoclast adhesion and activation. Front Biosci 3, d757-768.

Erlandsson, M. C., Jonsson, C. A., Lindberg, M. K., Ohlsson, C., and Carlsten, H. (2002). Raloxifene- and estradiol-mediated effects on uterus, bone and B lymphocytes in mice. J Endocrinol 175, 319-327.

Ferguson, C. M., Miclau, T., Hu, D., Alpern, E., and Helms, J. A. (1998). Common molecular pathways in skeletal morphogenesis and repair. Ann N Y Acad Sci 857, 33-42.

Gapstur, S. M., Morrow, M., and Sellers, T. A. (1999). Hormone replacement therapy and risk of breast cancer with a favorable histology: results of the Iowa Women's Health Study. JAMA 281(22), 2091-2097.

Gilgès, D., Vinit, M. A., Callebaut, I., Coulombel, L., Cacheux, V., Romeo, P. H., and Vigon, I. (2000). Polydom: a secreted protein with pentraxin, complement control protein, epidermal growth factor and von Willebrand factor A domains. Biochem J 352(1), 49-59.

Goltzman, D. (2002). Discoveries, drugs and skeletal disorders. Nat Rev Drug Discov 1(10), 784-796.

Gourdy, P., Mallat, Z., Castano, C., Garmy-Susini, B., Mac Gregor, J. L., Tedgui, A., Amal, J. F., and Bayard, F. (2003). The atheroprotective effect of 17 beta-estradiol is not altered in P-selectin- or ICAM-1-deficient hypercholesterolemic mice. Atherosclerosis. 166(1), 41-8.

Harrington, K. J., Syrigos, K. N., Uster, P. S., Zetter, A., Lewanski, C. R., Gullick, W. J., Vile, R. G., and Stewart, J. S. W. (2004). Targeted radiosensitisation by pegylated liposome-encapsulated 3',5'-O-dipalmitoyl 5-iodo-2'-deoxyuridine in a head and neck cancer xenograft model. British J Cancer 91, 366-373.

Ishihara, A., Sasaki, T., Debari, K., Furuya, R., Kawawa, T., Ramamurthy, N. S., and Golub, L. M. (1999). Effects of ovariectomy on bone morphology in maxillae of mature rats. J Electron Microsc 48, 465-469.

Isogai, T. and Otsuki, T. (2002). Direct submission (NEDO human cDNA sequencing project: "unnamed protein product"). Unpub. GenBank Accession AK075235. http://www.ncbi.nlm.nih.gov/entrez/viewer.fcgi?db=nucleotide&val=22761191

Jakacka, M., Ito, M., Weiss, J., Chien, P. Y., Gehm, B. D., and Jameson, J. L. (2001). Estrogen receptor binding to DNA is not required for its activity through the nonclassical AP1 pathway. J Biol Chem 276(17), 13615-13621.

Jaiswal, R. K., Jaiswal, N., Bruder, S. P., Mbalaviele, G., Marshak, D. R., and Pittenger, M. F. (2000). Adult human mesenchymal stem cell differentiation to the osteogenic or adipogenic lineage is regulated by mitogen-activated protein kinase. J Biol Chem 275(13), 9645-9652.

Kansas, G. S. (1996). Selectins and their ligands: current concepts and controversies. Blood 88(9), 3259-87.

Ke, H., Jee, W. S., Zeng, Q. Q., Li, M., and Lin, B. Y. (1993). Prostaglandin E2 increased rat cortical bone mass when administered immediately following ovariectomy. Bone Miner 21(3), 189-201.

Kushner, P. J., Agard, D. A., Greene, G. L., Scanlan, T. S., Shiau, A. K., Uht, R. M., and Webb, P. (2000). Estrogen receptor pathways to AP-1. J Steroid Biochem Mol Biol 74, 311-317.

Labrador, J. P., Brambilla, R., and Klein, R. (1997). The N-terminal globular domain of Eph receptors is sufficient for ligand binding and receptor signaling. Embo J 16, 3889-3897.

Lieberherr, M., Grosse, B., Kachkache, M., and Balsan, S. (1993). Cell signaling and estrogens in female rat osteoblasts: a possible involvement of unconventional non-nuclear receptors J Bone Miner Res 8(11), 1365-1376.

Liu, Z., Graff, E., and Benayahu, D. (2000). Effect of raloxifene-analog (LY 117018-Hcl) on the bone marrow of ovariectomized mice. J Cell Biochem 76, 509-517.

Manolagas, S. C., Kousteni, S., and Jilka, R. L. (2002). Sex steroids and bone. Recent Prog Horm Res 57, 385-409.

Massas, R., Korenstein, R., and Benayahu, D. (1998). Estrogen modulation of osteoblastic cell-to-cell communication. J Cell Biochem 69, 282-290.

Mendelsohn, M. E. and Karas, R. H. (1999). The protective effects of estrogen on the cardiovascular system. N Engl J Med 340, 1801-1811.

Moggs, J. G. and Orphanides, G. (2001). Estrogen receptors: orchestrators of pleiotropic cellular responses. EMBO Rep 2, 775-781.

Moggs, J. G., Deavall, D. G., and Orphanides, G. (2003). Sex steroids, ANGELS and osteoporosis. Bioessays 25, 195-199.

Monroe, D. G. and Spelsberg, T. C. (2003). A case for estrogen receptors on cell membranes and nongenomic actions of estrogen. Calcif Tissue Int 72, 183-184.

Olsen, B. R., Reginato, A. M., and Wang, W. (2000). Bone development. Annu Rev Cell Dev Biol 16, 191-220.

Onoe, Y., Miyaura, C., Ito, M., Ohta, H., Nozawa, S., and Suda, T. (2000). Comparative effects of estrogen and raloxifene on B lymphopoiesis and bone loss induced by sex steroid deficiency in mice. J Bone Miner Res 15, 541-549.

Parker, M. G. (1998). Transcriptional activation by oestrogen receptors. Biochem Soc Symp 63, 45-50.

Patel, K. D., Cuvelier, S. L., and Wiehler P. (2002). selectins: critical mediators of leukocyte recruitment. Immunology 14, 73-81.

Plant, A. and Tobias, J. H. (2001). Characterisation of the temporal sequence of osteoblast gene expression during estrogen-induced osteogenesis in female mice. J Cell Biochem 82, 683-691.

Plant, A., Samuels, A., Perry, M. J., Colley, S., Gibson, R., and Tobias, J. H. (2002). Estrogen-induced osteogenesis in mice is associated with the appearance of Cbfa1-expressing bone marrow cells. J Cell Biochem 84, 285-294.

Plotkin, L. I., Manolagas, S. C., and Bellido, T. (2002). Transduction of cell survival signals by connexin-43 hemichannels. J Biol Chem 277, 8648-8657.

Rickard, D. J., Subramaniam, M., Spelsberg, T. C. (1999). Molecular and cellular mechanisms of estrogen action on the skeleton. J Cell Biochem Suppl 32-33, 123-32.

Roche-Nagle, G., Connolly, E. M., Eng, M., Bouchier-Hayes, D. J., and Harmey, J. H. (2004). Antimetastatic activity of a cyclooxygenase-2 inhibitor. British J Cancer 91, 359-365.

Roggia, C., Gao, Y., Cenci, S., Weitzmann, M. N., Toraldo, G., Isaia, G., and Pacifici, R. (2001). Up-regulation of TNF-producing T cells in the bone marrow: a key mechanism by which estrogen deficiency induces bone loss in vivo. Proc Natl Acad Sci USA 98, 13960-13965.

Safe, S. (2001). Transcriptional activation of genes by 17 beta-estradiol through estrogen receptor-Sp1 interactions. Vitam Horm 62, 231-252.

Saintier, D., Burde, M. A., Rey, J. M., Maudelonde, T., De Vernejoul, M. C., and Cohen-Solal, M. E. (2004). 17β-Estradiol Downregulates β3-Integrin Expression in Differentiating and Mature Human Osteoclasts. J Cell Physiol 198, 269-276.

Sanchez, R., Nguyen, D., Rocha, W., White, J. H., and Mader, S. (2002). Diversity in the mechanisms of gene regulation by estrogen receptors. Bioessays 24, 244-254.

Scanlan, M. J., Gout, I., Gordon, C. M., Williamson, B., Stockert, E., Gure, A. O., Jager, D., Chen, Y. T., Mackay, A., O'Hare, M. J., Old, L. J. (2001a). Humoral immunity to human breast cancer: antigen definition and quantitative analysis of MRNA expression. Cancer Immun 1, 4.

Scanlan, M. J., Gout, I., Gordon, C. M., Williamson, B., Stockert, E., Gure, A. O., Jager, D., Chen, Y. T., Mackay, A., O'Hare, M. J., Old, L. J. (2001b). Unpub. "Serologically defined breast cancer antigen ny-br-38." TREMBL Accession No. Q9H284, EMBL-EBI Accession No. AF308289.

Shi, S., and Gronthos, S. (2003). Perivascular niche of postnatal mesenchymal stem cells in human bone marrow and dental pulp. J Bone Miner Res 18, 696-704.

Shur, I., Marom, R., Lokiec, F., Socher, R., and Benayahu, D. (2002). Identification of cultured progenitor cells from human marrow stroma. J Cell Biochem 87(1), 51-57.

Shur, I., Lokiec, F., Bleiberg, I., and Benayahu, D. (2001). Differential gene expression of cultured human osteoblasts. J Cell Biochem. 83, 547-553.

Stoll, B. and Parbhoo, S. (1983). Bone Metastasis. Raven Press Books, Ltd., New York, p. 14.

Stork, S., von Schacky, C., and Angerer P. (2002). The effect of 17beta-estradiol on endothelial and inflammatory markers in postmenopausal women: a randomized, controlled trial. Atherosclerosis. 165(2), 301-7

Tepass, U., Godt, D., and Winklbauer, R. (2002). Cell sorting in animal development: signalling and adhesive mechanisms in the formation of tissue boundaries. Curr Opin Genet Dev. 12(5), 572-582.

Tobias, J. H. (1999). The effects of SERMs on the skeleton. J Endocrinol Invest 22, 604-608.

Triffitt, J. T., Joyner, C. J., Oreffo, R. O., and Virdi, A. S. (1998). Osteogenesis: bone development from primitive progenitors. Biochem Soc Trans. 26(1), 21-27.

Vinholes, J. et al. (1996). Effects of Bone Metastases on Bone Metabolism: Implications for Diagnosis, Imaging and Assessment of Response to Cancer Treatment. Cancer Treatment Rev 22, 289-331.

Watts, N. B. (2000). Focus on primary care postmenopausal osteoporosis: an update. Obstet Gynecol Surv 55, S49-55.

Wessel, G. M., Berg, L., Adelson, D. L., Cannon, G., and McClay, D. R. (1998). A molecular analysis of hyalin—a substrate for cell adhesion in the hyaline layer of the sea urchin embryo. Dev Biol 193, 115-126.

Whittaker, C. A. and Hynes, R. O. (2002). Distribution and Evolution of von Willebrand/Integrin A Domains: Widely Dispersed Domains with Roles in Cell Adhesion and Elsewhere. Mol Biol Cell 13(10), 3369-3387.

Wren, B. G. (1992). The effect of oestrogen on the female cardiovascular system. Med J Aust 157, 204-208.

Zhang, J., Niu, C., Ye, L., Huang, H., He, X., Tong, W. G., Ross, J., Haug, J., Johnson, T., Feng, J. Q., Harris, S., Wiedemann, L. M., Mishina, Y., and Li, L. (2003). Identification of the haematopoietic stem cell niche and control of the niche size. Nature 425, 836-841.

Ke, H. et al. (2002). U.S. Pat. No. 6,352,970.

Love, S. et al. (2003). U.S. Pat. No. 6,642,010.

Welcher, A. A. et al. (2003). U.S. Pat No. 6,656,707.

Welcher, A. A. et al. (2002). WO0210388.

---

What is claimed is:

1. A method of isolating a stem cell, wherein the method comprises:
    (a) identifying the stem cell by detecting a presence of the polypeptide set forth in SEQ ID NO: 15 in an ex vivo human peripheral blood cell sample or an ex vivo human bone marrow cell sample, wherein the presence of said polypeptide set forth in SEQ ID NO: 15 is indicative of a stem cell; and
    (b) isolating the stem cell that expresses the polypeptide set forth in SEQ ID NO: 15 from said ex vivo human peripheral blood cell sample or said ex vivo human bone marrow cell sample.

2. The method of claim 1, wherein the stem cell is a mesenchymal stem cell or a hematopoietic stem cell.

3. A method of isolating a stem cell, wherein the method comprises:
    (a) identifying the stem cell by detecting a presence of the polypeptide set forth in SEQ ID NO: 15 in an ex vivo human skeletal muscle sample, wherein the presence of said polypeptide set forth in SEQ ID NO: 15 is indicative of a stem cell; and
    (b) isolating the stem cell that expresses the polypeptide set forth in SEQ ID NO: 15 from said ex vivo human skeletal muscle sample.

4. The method of claim 3, wherein the stem cell is a satellite stem cell or myoblast stem cell.

* * * * *